(12) United States Patent
Hanaoka et al.

(10) Patent No.: US 8,383,848 B2
(45) Date of Patent: Feb. 26, 2013

(54) TRANSITION METAL COMPOUND AND CATALYST FOR OLEFIN POLYMERIZATION

(75) Inventors: Hidenori Hanaoka, Chuo-ku (JP); Masato Takano, Ichihara (JP); Naoko Ochi, Ichihara (JP); Kazuo Takaoki, Ichihara (JP); Kazuyuki Ito, Ichihara (JP); Masayuki Hasegawa, Ichihara (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/171,581

(22) Filed: Jun. 29, 2011

(65) Prior Publication Data

US 2011/0319578 A1 Dec. 29, 2011

(30) Foreign Application Priority Data

Jun. 29, 2010 (JP) ................ 2010-147335
Jun. 29, 2010 (JP) ................ 2010-147338

(51) Int. Cl.
*C07F 17/00* (2006.01)
*C08F 4/6192* (2006.01)
*C08F 4/6592* (2006.01)
*B01J 31/22* (2006.01)

(52) U.S. Cl. .......... 556/53; 502/103; 502/152; 526/131; 526/133; 526/160; 526/165; 526/348; 526/943

(58) Field of Classification Search ........... 556/53; 502/103, 152; 526/131, 133, 160, 165, 348, 526/943

See application file for complete search history.

(56) References Cited

U.S. PATENT DOCUMENTS

| | | | |
|---|---|---|---|
| 5,883,275 A * | 3/1999 | Bingel et al. ............... 556/9 |
| 5,916,982 A | 6/1999 | Nakazawa et al. | |
| 7,141,639 B2 | 11/2006 | Iseki et al. | |
| 2006/0009595 A1 | 1/2006 | Rix et al. | |
| 2006/0293474 A1 * | 12/2006 | Brant et al. ............... 526/134 |

FOREIGN PATENT DOCUMENTS

| | | |
|---|---|---|
| JP | 9-151210 A | 6/1997 |
| JP | 2004-149761 A | 5/2004 |
| JP | 2008-505932 T | 2/2008 |

OTHER PUBLICATIONS

Lee et al., "Electronic Effects in Ziegler-Natta Polymerization of Propylene and ethylene using Soluble Metallocene Catalysts," Organometallics, vol. 11, pp. 2115-2122, (1992).

* cited by examiner

*Primary Examiner* — Caixia Lu
(74) *Attorney, Agent, or Firm* — Panitch Schwarze Belisario & Nadel LLP

(57) ABSTRACT

A transition metal compound represented by the formula (1-1) or the formula (1-2) (M is a transition metal atom) and a process for producing a catalyst for olefin polymerization comprising a step of bringing the transition metal compound into contact with a co-catalytic component for activation.

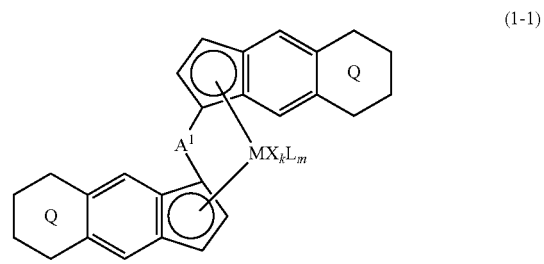

(1-1)

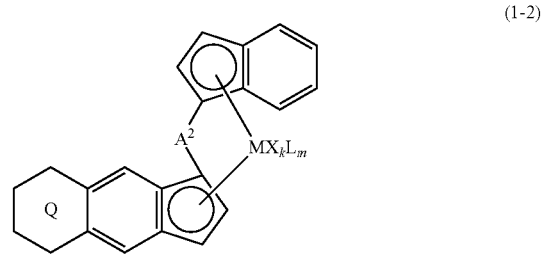

(1-2)

10 Claims, No Drawings

TRANSITION METAL COMPOUND AND CATALYST FOR OLEFIN POLYMERIZATION

BACKGROUND OF THE INVENTION

1. Field of the Invention

The present application claims the Paris Convention priority based on Japanese Patent Application Nos. 2010-147335 and 2010-147338 filed on Jun. 29, 2010, the entire content of which is incorporated herein by reference The present invention relates to a transition metal compound, a process for producing a catalyst for olefin polymerization, and a process for producing an olefin polymer.

2. Description of the Related Art

As an olefin polymer which is polymerized using a metallocene catalyst, an ethylene-α-olefin copolymer polymerized using a metallocene catalyst comprising racemic-ethylenebis(1-indenyl)zirconium dichloride (JP-A-9-151210, corresponding to U.S. Pat. No. 5,916,982); an ethylene-α-olefin copolymer polymerized using a metallocene catalyst comprising racemic-ethylenebis(1-indenyl)zirconium diphenoxide (JP-A-2004-149761, corresponding to U.S. Pat. No. 7,141,639); and an ethylene-α-olefin copolymer polymerized using a metallocene catalyst comprising crosslinked bisindenyl complex in which a particular site of an indenyl ring is modified (JP-T-2008-505932, corresponding to US Patent Application Publication 2006/0009595, and Organometallics 1992, Vol. 11, No. 6, 2115-2122) can be exemplified.

SUMMARY OF THE INVENTION

However, there is room for improving the olefin polymer obtained using a metallocene catalyst in respect of molding processability. An object of the present invention is to provide a process for producing a catalyst for olefin polymerization comprising a metallocene catalyst, which can produce an olefin polymer excellent in molding processability, a transition metal compound used in the production process, and a process for producing an olefin polymer.

The present invention is a transition metal compound represented by the formula (1-1):

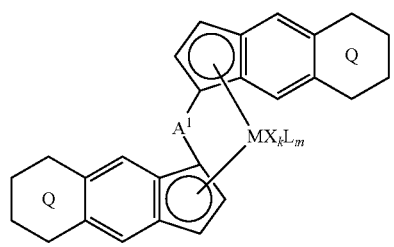

(1-1)

wherein M represents a transition metal atom of the Group 3, 4, 5, Group lanthanide or Group actinide of the periodic table;

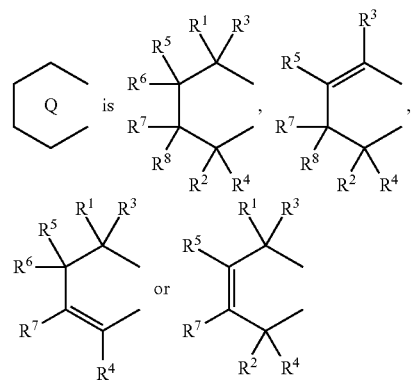

(i) $R^1$ and $R^2$ are the same as, or different from each other, and are an alkyl group having 1 to 20 carbon atoms and optionally having a halogen atom as a substituent,
a cycloalkyl group having 3 to 10 carbon atoms and optionally having a halogen atom as a substituent,
an alkenyl group having 2 to 20 carbon atoms and optionally having a halogen atom as a substituent,
an alkynyl group having 2 to 20 carbon atoms and optionally having a halogen atom as a substituent,
an aralkyl group having 7 to 20 carbon atoms and optionally having a halogen atom as a substituent, or
an aryl group having 6 to 20 carbon atoms and optionally having a halogen atom as a substituent, (ii) $R^3$ and $R^4$ are the same as, or different from each other, and are a hydrogen atom,
an alkyl group having 1 to 20 carbon atoms and optionally having a halogen atom as a substituent,
a cycloalkyl group having 3 to 10 carbon atoms and optionally having a halogen atom as a substituent,
an alkenyl group having 2 to 20 carbon atoms and optionally having a halogen atom as a substituent,
an alkynyl group having 2 to 20 carbon atoms and optionally having a halogen atom as a substituent,
an aralkyl group having 7 to 20 carbon atoms and optionally having a halogen atom as a substituent, or
an aryl group having 6 to 20 carbon atoms and optionally having a halogen atom as a substituent, (iii) $R^5$ to $R^8$ are the same as, or different from one another, and are a hydrogen atom,
an alkyl group having 1 to 20 carbon atoms and optionally having a halogen atom as a substituent,
a cycloalkyl group having 3 to 10 carbon atoms and optionally having a halogen atom as a substituent,
an alkenyl group having 2 to 20 carbon atoms and optionally having a halogen atom as a substituent,
an alkynyl group having 2 to 20 carbon atoms and optionally having a halogen atom as a substituent,
an aralkyl group having 7 to 20 carbon atoms and optionally having a halogen atom as a substituent,
an aryl group having 6 to 20 carbon atoms and optionally having a halogen atom as a substituent,
an alkoxy group having 1 to 20 carbon atoms and optionally having a halogen atom as a substituent,
an aralkyloxy group having 7 to 20 carbon atoms and optionally having a halogen atom as a substituent,
an aryloxy group having 6 to 20 carbon atoms and optionally having a halogen atom as a substituent,
a silyl group optionally having, as a substituent, a hydrocarbyl group or a halogenated hydrocarbyl group having 1 to 20 carbon atoms, an amino group optionally having, as a substituent, a hydrocarbyl group or a halogenated hydrocarbyl group having 1 to 20 carbon atoms, or a heterocyclic compound residue, (iv) $R^1$ and $R^3$, $R^2$ and $R^4$, $R^5$ and $R^6$, $R^5$ and $R^7$, or $R^7$ and $R^8$ may be taken together with each other to form a ring, wherein the ring may have a substituent;

$A^1$ represents a $-[C(R^9)(R^{10})]_n-$group, $R^9$ and $R^{10}$ are the same as, or different from each other, and are a hydrogen atom, a halogen atom, an alkyl group having 1 to 20 carbon atoms and optionally having a halogen atom as a substituent, a cycloalkyl group having 3 to 10 carbon atoms and optionally having a halogen atom as a substituent, an aryl group having 6 to 20 carbon atoms and optionally having a halogen atom as a substituent, or a silyl group optionally having, as a substituent, a hydrocarbyl group or a halogenated hydrocarbyl group having 1 to 20 carbon atoms, when plural $R^9$s or $R^{10}$s exist, respectively, they are the same as, or different from each other, and n is 1, 2, 3 or 4;

X is a hydrogen atom, a halogen atom, an alkyl group having 1 to 20 carbon atoms and optionally having a halogen atom as a substituent, a cycloalkyl group having 3 to 10 carbon atoms and optionally having a halogen atom as a substituent, an aralkyl group having 7 to 20 carbon atoms and optionally having a halogen atom as a substituent, an aryl group having 6 to 20 carbon atoms and optionally having a halogen atom as a substituent, an alkoxy group having 1 to 20 carbon atoms and optionally having a halogen atom as a substituent, an aralkyloxy group having 7 to 20 carbon atoms and optionally having a halogen atom as a substituent, an aryloxy group having 6 to 20 carbon atoms and optionally having a halogen atom as a substituent, a silyl group optionally having, as a substituent, a hydrocarbyl group or a halogenated hydrocarbyl group having 1 to 20 carbon atoms, an amino group optionally having, as a substituent, a hydrocarbyl group or a halogenated hydrocarbyl group having 1 to 20 carbon atoms, a thiolate group optionally having, as a substituent, a hydrocarbyl group or a halogenated hydrocarbyl group having 1 to 20 atoms, or a carboxyl group optionally having, as a substituent, a hydrocarbyl group or a halogenated hydrocarbyl group having 1 to 20 carbon atoms, when plural Xs exist, they are the same as, or different from each other, and Xs may be taken together to form a ring;

k is 1, 2, 3 or 4; Y is a neutral Lewis base; m is 0, 1, 2, 3 or 4, and when plural Ys exist, they are the same as, or different from each other; the sum of k and m is 2, 3 or 4.

The present invention is also a compound represented by the formula (2-1):

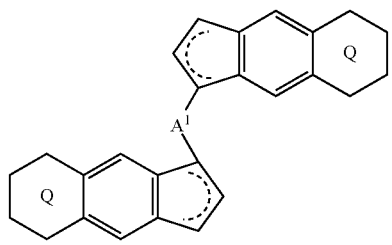

(2-1)

wherein

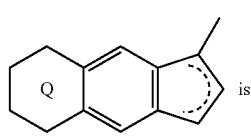 is

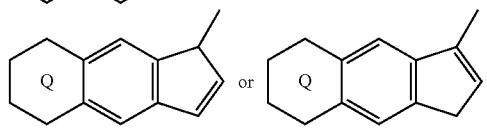

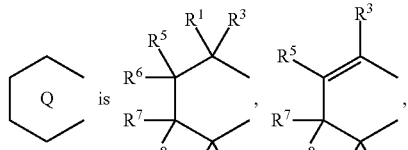

Q is

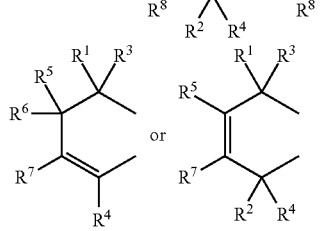

(i) $R^1$ and $R^2$ are the same as, or different from each other, and represent an alkyl group having 1 to 20 carbon atoms and optionally having a halogen atom as a substituent, a cycloalkyl group having 3 to 10 carbon atoms and optionally having a halogen atom as a substituent, an alkenyl group having 2 to 20 carbon atoms and optionally having a halogen atom as a substituent, an alkynyl group having 2 to 20 carbon atoms and optionally having a halogen atom as a substituent, an aralkyl group having 7 to 20 carbon atoms and optionally having a halogen atom as a substituent, or an aryl group having 6 to 20 carbon atoms and optionally having a halogen atom as a substituent, (ii) $R^3$ and $R^4$ are the same as, or different from each other, and are a hydrogen atom, an alkyl group having 1 to 20 carbon atoms and optionally having a halogen atom as a substituent, a cycloalkyl group having 3 to 10 carbon atoms and optionally having a halogen atom as a substituent, an alkenyl group having 2 to 20 carbon atoms and optionally having a halogen atom as a substituent, an alkynyl group having 2 to 20 carbon atoms and optionally having a halogen atom as a substituent, an aralkyl group having 7 to 20 carbon atoms and optionally having a halogen atom as a substituent, or an aryl group having 6 to 20 carbon atoms and optionally having a halogen atom as a substituent, (iii) $R^5$ to $R^8$ are the same as, or different from one another, and represent a hydrogen atom, an alkyl group having 1 to 20 carbon atoms and optionally having a halogen atom as a substituent, a cycloalkyl group having 3 to 10 carbon atoms and optionally having a halogen atom as a substituent, an alkenyl group having 2 to 20 carbon atoms and optionally having a halogen atom as a substituent, an alkynyl group having 2 to 20 carbon atoms and optionally having a halogen atom as a substituent, an aralkyl group having 7 to 20 carbon atoms and optionally having a halogen atom as a substituent, an aryl group having 6 to 20 carbon atoms and optionally having a halogen atom as a substituent, an alkoxy group having 1 to 20 carbon atoms and optionally having a halogen atom as a substituent, an aralkyloxy group having 7 to 20 carbon atoms and optionally having a halogen atom as a substituent, an aryloxy group having 6 to 20 carbon atoms and optionally having a halogen atom as a substituent, a silyl group optionally having, as a substituent, a hydrocarbyl group or a halogenated hydrocarbyl group having 1 to 20 carbon atoms, an amino group optionally having, as a substituent, a hydrocarbyl group or a halogenated hydrocarbyl group having 1 to 20 carbon atoms, or a heterocyclic compound residue, (iv) $R^1$ and $R^3$, $R^2$ and $R^4$, $R^5$ and $R^6$, $R^5$ and $R^7$, or $R^7$ and $R^8$ may be taken together with each other to form a ring, wherein the ring may have a substituent;

$A^1$ represents a $-[C(R^9)(R^{10})]_n$-group, $R^9$ and $R^{10}$ are the same as, or different from each other, and are a hydrogen atom, a halogen atom, an alkyl group having 1 to 20 carbon atoms and optionally having a halogen atom as a substituent, a cycloalkyl group having 3 to 10 carbon atoms and optionally having a halogen atom as a substituent, an aryl group having 6 to 20 carbon atoms and optionally having a halogen atom as a substituent, or a silyl group optionally having, as a substituent, a hydrocarbyl group or a halogenated hydrocarbyl group having 1 to 20 carbon atoms, when plural $R^9$s or $R^{10}$s exist, they are the same as, or different from each other, and n is 1, 2, 3 or 4.

The present invention is further a process for producing a catalyst for olefin polymerization comprising a step of bringing a transition metal compound represented by the formula (1-1) into contact with a co-catalytic component for activation. This production process is referred to as "a production process 1 of a catalyst for olefin polymerization".

The present invention is also further a process for producing an olefin polymer comprising a step of polymerizing an olefin in the presence of a catalyst for olefin polymerization produced by the production process 1 of a catalyst for olefin polymerization.

The present invention is also a transition metal compound represented by the formula (1-2):

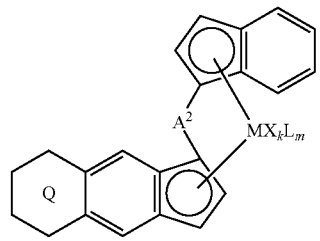

(1-2)

wherein M represents a transition metal atom of the Group 3, 4, 5, Group lanthanide or Group actinide of the periodic table,

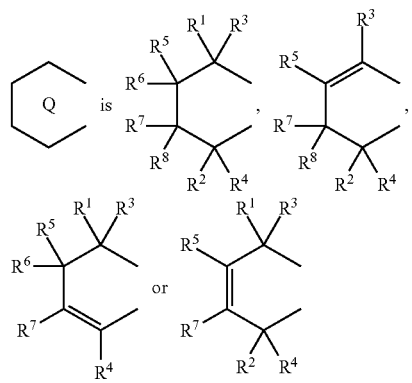

(i) $R^1$ and $R^2$ are the same as, or different from each other, and represent an alkyl group having 1 to 20 carbon atoms and optionally having a halogen atom as a substituent, a cycloalkyl group having 3 to 10 carbon atoms and optionally having a halogen atom as a substituent, an alkenyl group having 2 to 20 carbon atoms and optionally having a halogen atom as a substituent, an alkynyl group having 2 to 20 carbon atoms and optionally having a halogen atom as a substituent, an aralkyl group having 7 to 20 carbon atoms and optionally having a halogen atom as a substituent, or an aryl group having 6 to 20 carbon atoms and optionally having a halogen atom as a substituent, (ii) $R^3$ and $R^4$ are the same as, or different from each other, and represent a hydrogen atom, an alkyl group having 1 to 20 carbon atoms and optionally having a halogen atom as a substituent, a cycloalkyl group having 3 to 10 carbon atoms and optionally having a halogen atom as a substituent, an alkenyl group having 2 to 20 carbon atoms and optionally having a halogen atom as a substituent, an alkynyl group having 2 to 20 carbon atoms and optionally having a halogen atom as a substituent, an aralkyl group having 7 to 20 carbon atoms and optionally having a halogen atom as a substituent, or an aryl group having 6 to 20 carbon atoms and optionally having a halogen atom as a substituent, (iii) $R^5$ to $R^8$ are the same as, or different from one another, and represent a hydrogen atom, an alkyl group having 1 to 20 carbon atoms and optionally having a halogen atom as a substituent, a cycloalkyl group having 3 to 10 carbon atoms and optionally having a halogen atom as a substituent, an alkenyl group having 2 to 20 carbon atoms and optionally having a halogen atom as a substituent,
an alkynyl group having 2 to 20 carbon atoms and optionally having a halogen atom as a substituent,
an aralkyl group having 7 to 20 carbon atoms and optionally having a halogen atom as a substituent,
an aryl group having 6 to 20 carbon atoms and optionally having a halogen atom as a substituent,
an alkoxy group having 1 to 20 carbon atoms and optionally having a halogen atom as a substituent,
an aralkyloxy group having 7 to 20 carbon atoms and optionally having a halogen atom as a substituent,
an aryloxy group having 6 to 20 carbon atoms and optionally having a halogen atom as a substituent,
a silyl group optionally having, as a substituent, a hydrocarbyl group or a halogenated hydrocarbyl group having 1 to 20 carbon atoms,
an amino group optionally having, as a substituent, a hydrocarbyl group or a halogenated hydrocarbyl group having 1 to 20 carbon atoms, or
a heterocyclic compound residue,
(iv) $R^1$ and $R^3$, $R^2$ and $R^4$, $R^5$ and $R^6$, $R^5$ and $R^7$, or $R^7$ and $R^8$ may be taken together with each other to form a ring, wherein the ring may have a substituent;
$A^2$ represents a —$[Z(R^{11},R^{12})]_n$-group, wherein Z represents a silicon atom, a germanium atom, a tin atom or a carbon atom, $R^{11}$ and $R^{12}$ are the same as,
or different from each other, and represent a hydrogen atom, an alkyl group having 1 to 20 carbon atoms and optionally having a halogen atom as a substituent,
a cycloalkyl group having 3 to 10 carbon atoms and optionally having a halogen atom as a substituent,
an aryl group having 6 to 20 carbon atoms and optionally having a halogen atom as a substituent, or
a silyl group optionally having, as a substituent, a hydrocarbyl group or a halogenated hydrocarbyl group having 1 to 20 carbon atoms, and
n represents 1, 2, 3 or 4, and when plural Zs, $R^{11}$Zs or $R^{11}$s or $R^{12}$s exist, they may be the same as, or different from one another,
X represents a hydrogen atom, a fluorine atom, a chlorine atom, a bromine atom, an iodine atom,
an alkyl group having 1 to 20 carbon atoms and optionally having a halogen atom as a substituent,
a cycloalkyl group having 3 to 10 carbon atoms and optionally having a halogen atom as a substituent,
an aralkyl group having 7 to 20 carbon atoms and optionally having a halogen atom as a substituent,
an aryl group having 6 to 20 carbon atoms and optionally having a halogen atom as a substituent,
an alkoxy group having 1 to 20 carbon atoms and optionally having a halogen atom as a substituent,
an aralkyloxy group having 7 to 20 carbon atoms and optionally having a halogen atom as a substituent,
an aryloxy group having 6 to 20 carbon atoms and optionally having a halogen atom as a substituent,
a silyl group optionally having, as a substituent, a hydrocarbyl group or a halogenated hydrocarbyl group having 1 to 20 carbon atoms,
an amino group optionally having, as a substituent, a hydrocarbyl group or a halogenated hydrocarbyl group having 1 to 20 carbon atoms,
a thiolate group optionally having, as a substituent, a hydrocarbyl group or a halogenated hydrocarbyl group having 1 to 20 carbon atoms, or
a carboxylate group optionally having, as a substituent, a hydrocarbyl group or a halogenated hydrocarbyl group having 1 to 20 carbon atoms, and when plural Xs exist, they are the same as, or different from each other, and adjacent Xs may be taken together with each other to form a ring;
k represents 1, 2 or 3; L represents a neutral Lewis base, and when plural Ls exist, plural Ls are the same as, or different from each other; m represents 0, 1, 2, 3 or 4; the sum of k and m is 2, 3 or 4.

The present invention is also a compound represented by the formula (2-2):

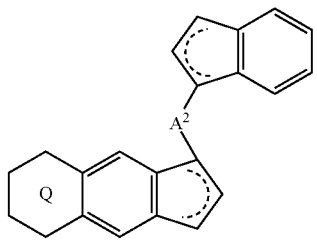

(2-2)

wherein

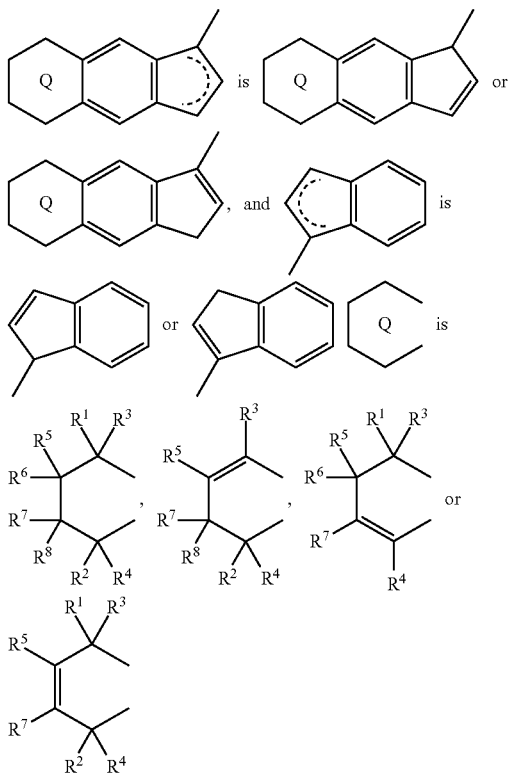

(i) $R^1$ and $R^2$ are the same as, or different from each other, and represent
an alkyl group having 1 to 20 carbon atoms and optionally having a halogen atom as a substituent,
a cycloalkyl group having 3 to 10 carbon atoms and optionally having a halogen atom as a substituent,
an alkenyl group having 2 to 20 carbon atoms and optionally having a halogen atom as a substituent,
an alkynyl group having 2 to 20 carbon atoms and optionally having a halogen atom as a substituent,
an aralkyl group having 7 to 20 carbon atoms and optionally having a halogen atom as a substituent, or an aryl group having 6 to 20 carbon atoms and optionally having a halogen atom as a substituent, (ii) $R^3$ and $R^4$ are the same as, or different from each other, and represent a hydrogen atom, an alkyl group having 1 to 20 carbon atoms and optionally having a halogen atom as a substituent, a cycloalkyl group having 3 to 10 carbon atoms and optionally having a halogen atom as a substituent, an alkenyl group having 2 to 20 carbon atoms and optionally having a halogen atom as a substituent, an alkynyl group having 2 to 20 carbon atoms and optionally having a halogen atom as a substituent, an aralkyl group having 7 to 20 carbon atoms and optionally having a halogen atom as a substituent, or an aryl group having 6 to 20 carbon atoms and optionally having a halogen atom as a substituent, (iii) $R^5$ to $R^8$ are the same as, or different from each other, and represent a hydrogen atom, an alkyl group having 1 to 20 carbon atoms and optionally having a halogen atom as a substituent, a cycloalkyl group having 3 to 10 carbon atoms and optionally having a halogen atom as a substituent, an alkenyl group having 2 to 20 carbon atoms and optionally having a halogen atom as a substituent, an alkynyl group having 2 to 20 carbon atoms and optionally having a halogen atom as a substituent, an aralkyl group having 7 to 20 carbon atoms and optionally having a halogen atom as a substituent, an aryl group having 6 to 20 carbon atoms and optionally having a halogen atom as a substituent, an alkoxy group having 1 to 20 carbon atoms and optionally having a halogen atom as a substituent, an aralkyloxy group having 7 to 20 carbon atoms and optionally having a halogen atom as a substituent, an aryloxy group having 6 to 20 carbon atoms and optionally having a halogen atom as a substituent, a silyl group optionally having, as a substituent, a hydrocarbyl group or a halogenated hydrocarbyl group having 1 to 20 carbon atoms, an amino group optionally having, as a substituent, a hydrocarbyl group or a halogenated hydrocarbyl group having 1 to 20 carbon atoms, or a heterocyclic compound residue, (iv) $R^1$ and $R^3$, $R^2$ and $R^4$, $R^5$ and $R^6$, $R^5$ and $R^7$, or $R^7$ and $R^8$ may be taken together with each other to form a ring, wherein the ring may have a substituent;

$A^2$ represents a $-[Z(R)(R^{11})(R^{12})]_n-$group, wherein Z represents a silicon atom, a germanium atom, a tin atom or a carbon atom, $R^{11}$ and $R^{12}$ are the same as, or different from each other, and represent a hydrogen atom, an alkyl group having 1 to 20 carbon atoms and optionally having a halogen atom as a substituent, a cycloalkyl group having 3 to 10 carbon atoms and optionally having a halogen atom as a substituent, an aryl group having 6 to 20 carbon atoms and optionally having a halogen atom as a substituent, or a silyl group optionally having, as a substituent, a hydrocarbyl group or a halogenated hydrocarbyl group having 1 to 20 carbon atoms, and n represents 1, 2, 3 or 4, and when plural Zs, $R^{11}$s or $R^{12}$s exist, they are the same as, or different from one another.

The present invention is also a process for producing a catalyst for olefin polymerization comprising a step of bringing a transition metal compound represented by the formula (1-2) into contact with a co-catalytic component for activation. This production process is referred to as "a production process 2 of a catalyst for olefin polymerization".

The present invention is also a process for producing an olefin polymer comprising a step of polymerizing an olefin in the presence of a catalyst for olefin polymerization produced by the production process 2 of a catalyst for olefin polymerization.

Hereinafter, the formula (1-1) and the formula (1-2) are collectively referred to as "formula (1)" and the formula (2-1) and the formula (2-2) are collectively referred to as "formula (2)".

That is, the present invention provides the following.

[1] A transition metal compound represented by the formula (1-1):

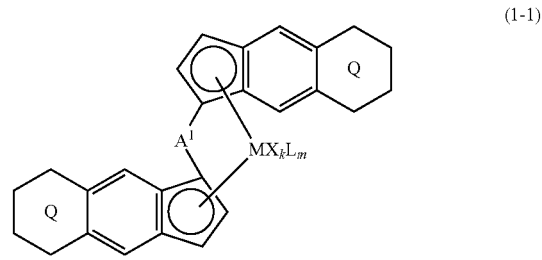

(1-1)

wherein M represents a transition metal atom of the Group 3, 4, 5, Group lanthanide or Group actinide of the periodic table;

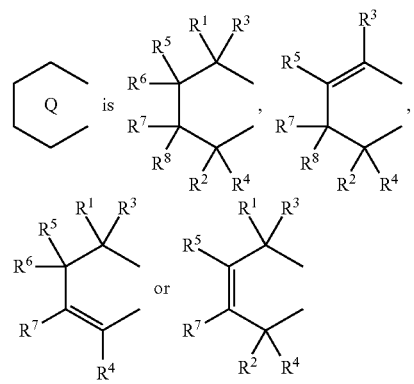

(i) $R^1$ and $R^2$ are the same as, or different from each other, and are an alkyl group having 1 to 20 carbon atoms and optionally having a halogen atom as a substituent, a cycloalkyl group having 3 to 10 carbon atoms and optionally having a halogen atom as a substituent, an alkenyl group having 2 to 20 carbon atoms and optionally having a halogen atom as a substituent, an alkynyl group having 2 to 20 carbon atoms and optionally having a halogen atom as a substituent, an aralkyl group having 7 to 20 carbon atoms and optionally having a halogen atom as a substituent, or an aryl group having 6 to 20 carbon atoms and optionally having a halogen atom as a substituent, (ii) $R^3$ and $R^4$ are the same as, or different from each other, and are a hydrogen atom, an alkyl group having 1 to 20 carbon atoms and optionally having a halogen atom as a substituent, a cycloalkyl group having 3 to 10 carbon atoms and optionally having a halogen atom as a substituent, an alkenyl group having 2 to 20 carbon atoms and optionally having a halogen atom as a substituent, an alkynyl group having 2 to 20 carbon atoms and optionally having a halogen atom as a substituent,
an aralkyl group having 7 to 20 carbon atoms and optionally having a halogen atom as a substituent, or
an aryl group having 6 to 20 carbon atoms and optionally having a halogen atom as a substituent,
(iii) $R^5$ to $R^8$ are the same as, or different from one another, and are a hydrogen atom,
an alkyl group having 1 to 20 carbon atoms and optionally having a halogen atom as a substituent,
a cycloalkyl group having 3 to 10 carbon atoms and optionally having a halogen atom as a substituent,
an alkenyl group having 2 to 20 carbon atoms and optionally having a halogen atom as a substituent,
an alkynyl group having 2 to 20 carbon atoms and optionally having a halogen atom as a substituent,
an aralkyl group having 7 to 20 carbon atoms and optionally having a halogen atom as a substituent,
an aryl group having 6 to 20 carbon atoms and optionally having a halogen atom as a substituent,
an alkoxy group having 1 to 20 carbon atoms and optionally having a halogen atom as a substituent,
an aralkyloxy group having 7 to 20 carbon atoms and optionally having a halogen atom as a substituent,
an aryloxy group having 6 to 20 carbon atoms and optionally having a halogen atom as a substituent,
a silyl group optionally having, as a substituent, a hydrocarbyl group or a halogenated hydrocarbyl group having 1 to 20 carbon atoms,
an amino group optionally having, as a substituent, a hydrocarbyl group or a halogenated hydrocarbyl group having 1 to 20 carbon atoms, or
a heterocyclic compound residue,
(iv) $R^1$ and $R^3$, $R^2$ and $R^4$, $R^5$ and $R^6$, $R^5$ and $R^7$, or $R^7$ and $R^8$ may be taken together with each other to form a ring, wherein the ring may have a substituent;
$A^1$ represents a —$[C(R^9)(R^{10})]_n$-group,
$R^9$ and $R^{10}$ are the same as, or different from each other, and are a hydrogen atom, a halogen atom,
an alkyl group having 1 to 20 carbon atoms and optionally having a halogen atom as a substituent,
a cycloalkyl group having 3 to 10 carbon atoms and optionally having a halogen atom as a substituent,
an aryl group having 6 to 20 carbon atoms and optionally having a halogen atom as a substituent, or
a silyl group optionally having, as a substituent, a hydrocarbyl group or a halogenated hydrocarbyl group having 1 to 20 carbon atoms,
when plural $R^9$s or $R^{10}$s exist, respectively, they are the same as, or different from each other, and n is 1, 2, 3 or 4;
X is a hydrogen atom, a halogen atom,
an alkyl group having 1 to 20 carbon atoms and optionally having a halogen atom as a substituent,
a cycloalkyl group having 3 to 10 carbon atoms and optionally having a halogen atom as a substituent,
an aralkyl group having 7 to 20 carbon atoms and optionally having a halogen atom as a substituent,
an aryl group having 6 to 20 carbon atoms and optionally having a halogen atom as a substituent,
an alkoxy group having 1 to 20 carbon atoms and optionally having a halogen atom as a substituent,
an aralkyloxy group having 7 to 20 carbon atoms and optionally having a halogen atom as a substituent,
an aryloxy group having 6 to 20 carbon atoms and optionally having a halogen atom as a substituent,
a silyl group optionally having, as a substituent, a hydrocarbyl group or a halogenated hydrocarbyl group having 1 to 20 carbon atoms,
an amino group optionally having, as a substituent, a hydrocarbyl group or a halogenated hydrocarbyl group having 1 to 20 carbon atoms,
a thiolate group optionally having, as a substituent, a hydrocarbyl group or a halogenated hydrocarbyl group having 1 to 20 atoms, or
a carboxyl group optionally having, as a substituent, a hydrocarbyl group or a halogenated hydrocarbyl group having 1 to 20 carbon atoms,
when plural Xs exist, they are the same as, or different from each other, and Xs may be taken together to form a ring;
k is 1, 2, 3 or 4; Y is a neutral Lewis base; m is 0, 1, 2, 3 or 4, and when plural Ys exist, they are the same as, or different from each other; the sum of k and m is 2, 3 or 4.

[2] The transition metal compound according to the item [1], wherein $A^1$ is a —$CH_2CH_2$— group.

[3] The transition metal compound according to the item [1], wherein X is a fluorine atom, a chlorine atom, a bromine atom, an iodine atom, an alkyl group having 1 to 20 carbon atoms and optionally having a halogen atom as a substituent, an aryl group having 7 to 20 carbon atoms and optionally having a halogen atom as a substituent, an alkoxy group having 1 to 20 carbon atoms and optionally having a halogen atom as a substituent, an aryloxy group having 6 to 20 carbon atoms and optionally having a halogen atom as a substituent, an amino group optionally having, as a substituent, a hydrocarbyl group or a halogenated hydrocarbyl group having 1 to 20 carbon atoms, and Xs may be taken together with each other to form a ring.

[4] The transition metal compound according to the item [1], wherein M is a titanium atom, a zirconium atom or a hafnium atom.

[5] The transition metal compound according to the item [1], wherein X is an aryloxy group having 6 to 20 carbon atoms and optionally having a halogen atom as a substituent.

[6] A compound represented by the formula (2-1);

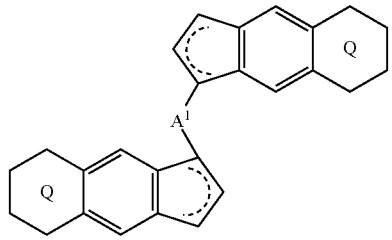

(2-1)

wherein

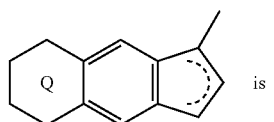 is

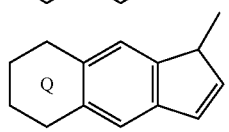 or 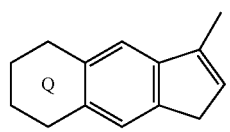

-continued

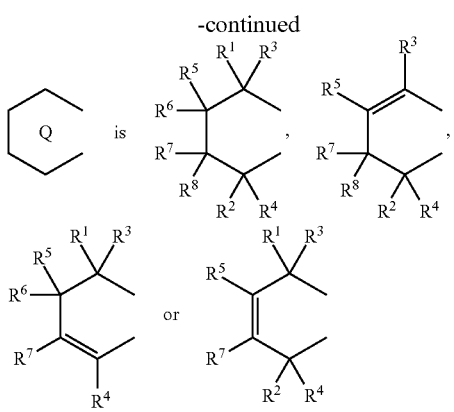

(i) $R^1$ and $R^2$ are the same as, or different from each other, and represent an alkyl group having 1 to 20 carbon atoms and optionally having a halogen atom as a substituent,
a cycloalkyl group having 3 to 10 carbon atoms and optionally having a halogen atom as a substituent,
an alkenyl group having 2 to 20 carbon atoms and optionally having a halogen atom as a substituent,
an alkynyl group having 2 to 20 carbon atoms and optionally having a halogen atom as a substituent,
an aralkyl group having 7 to 20 carbon atoms and optionally having a halogen atom as a substituent, or
an aryl group having 6 to 20 carbon atoms and optionally having a halogen atom as a substituent,
(ii) $R^3$ and $R^4$ are the same as, or different from each other, and are a hydrogen atom,
an alkyl group having 1 to 20 carbon atoms and optionally having a halogen atom as a substituent,
a cycloalkyl group having 3 to 10 carbon atoms and optionally having a halogen atom as a substituent,
an alkenyl group having 2 to 20 carbon atoms and optionally having a halogen atom as a substituent,
an alkynyl group having 2 to 20 carbon atoms and optionally having a halogen atom as a substituent,
an aralkyl group having 7 to 20 carbon atoms and optionally having a halogen atom as a substituent, or
an aryl group having 6 to 20 carbon atoms and optionally having a halogen atom as a substituent,
(iii) $R^5$ to $R^8$ are the same as, or different from one another, and represent a hydrogen atom,
an alkyl group having 1 to 20 carbon atoms and optionally having a halogen atom as a substituent,
a cycloalkyl group having 3 to 10 carbon atoms and optionally having a halogen atom as a substituent,
an alkenyl group having 2 to 20 carbon atoms and optionally having a halogen atom as a substituent,
an alkynyl group having 2 to 20 carbon atoms and optionally having a halogen atom as a substituent,
an aralkyl group having 7 to 20 carbon atoms and optionally having a halogen atom as a substituent,
an aryl group having 6 to 20 carbon atoms and optionally having a halogen atom as a substituent,
an alkoxy group having 1 to 20 carbon atoms and optionally having a halogen atom as a substituent,
an aralkyloxy group having 7 to 20 carbon atoms and optionally having a halogen atom as a substituent,
an aryloxy group having 6 to 20 carbon atoms and optionally having a halogen atom as a substituent,
a silyl group optionally having, as a substituent, a hydrocarbyl group or a halogenated hydrocarbyl group having 1 to 20 carbon atoms,
an amino group optionally having, as a substituent, a hydrocarbyl group or a halogenated hydrocarbyl group having 1 to 20 carbon atoms, or
a heterocyclic compound residue,
(iv) $R^1$ and $R^3$, $R^2$ and $R^4$, $R^5$ and $R^6$, $R^5$ and $R^7$, or $R^7$ and $R^8$ may be taken together with each other to form a ring, wherein the ring may have a substituent;
$A^1$ represents a $—[C(R^9)(R^{10})]_n$-group,
$R^9$ and $R^{19}$ are the same as, or different from each other, and are a hydrogen atom, a halogen atom,
an alkyl group having 1 to 20 carbon atoms and optionally having a halogen atom as a substituent,
a cycloalkyl group having 3 to 10 carbon atoms and optionally having a halogen atom as a substituent,
an aryl group having 6 to 20 carbon atoms and optionally having a halogen atom as a substituent, or
a silyl group optionally having, as a substituent, a hydrocarbyl group or a halogenated hydrocarbyl group having 1 to 20 carbon atoms, when plural $R^9$s or $R^{19}$s exist, they are the same as, or different from each other, and n is 1, 2, 3 or 4.

[7] The compound according to the item [6], wherein $A^1$ is a $—CH_2CH_2—$ group.

[8] A process for producing a catalyst for olefin polymerization comprising a step of bringing the transition metal compound according to the item [1] into contact with a co-catalytic component for activation.

[9] A process for producing an olefin polymer comprising a step of polymerizing an olefin in the presence of the catalyst for olefin polymerization produced by the production process according to the item [8].

[10] The production process according to the item [9], wherein the olefin is a combination of ethylene and α-olefin.

[11] A transition metal compound represented by the formula (1-2):

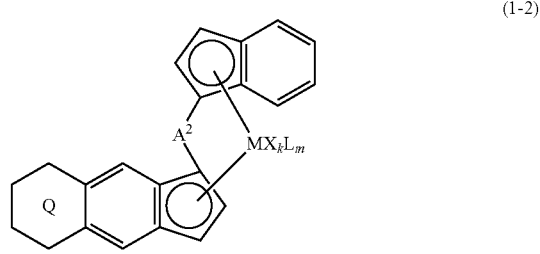

(1-2)

wherein M represents a transition metal atom of the Group 3, 4, 5, Group lanthanide or Group actinide of the periodic table,

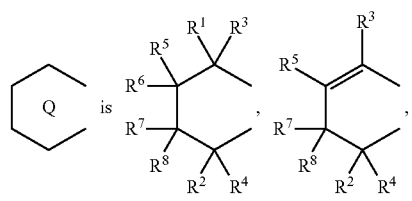

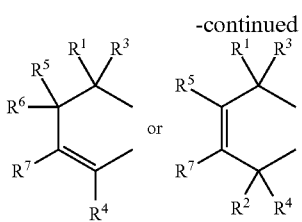

(i) $R^1$ and $R^2$ are the same as, or different from each other, and represent an alkyl group having 1 to 20 carbon atoms and optionally having a halogen atom as a substituent,
a cycloalkyl group having 3 to 10 carbon atoms and optionally having a halogen atom as a substituent,
an alkenyl group having 2 to 20 carbon atoms and optionally having a halogen atom as a substituent,
an alkynyl group having 2 to 20 carbon atoms and optionally having a halogen atom as a substituent,
an aralkyl group having 7 to 20 carbon atoms and optionally having a halogen atom as a substituent, or
an aryl group having 6 to 20 carbon atoms and optionally having a halogen atom as a substituent, (ii) $R^3$ and $R^4$ are the same as, or different from each other, and represent a hydrogen atom,
an alkyl group having 1 to 20 carbon atoms and optionally having a halogen atom as a substituent,
a cycloalkyl group having 3 to 10 carbon atoms and optionally having a halogen atom as a substituent,
an alkenyl group having 2 to 20 carbon atoms and optionally having a halogen atom as a substituent,
an alkynyl group having 2 to 20 carbon atoms and optionally having a halogen atom as a substituent,
an aralkyl group having 7 to 20 carbon atoms and optionally having a halogen atom as a substituent, or
an aryl group having 6 to 20 carbon atoms and optionally having a halogen atom as a substituent, (iii) $R^5$ to $R^8$ are the same as, or different from one another, and represent a hydrogen atom,
an alkyl group having 1 to 20 carbon atoms and optionally having a halogen atom as a substituent,
a cycloalkyl group having 3 to 10 carbon atoms and optionally having a halogen atom as a substituent,
an alkenyl group having 2 to 20 carbon atoms and optionally having a halogen atom as a substituent,
an alkynyl group having 2 to 20 carbon atoms and optionally having a halogen atom as a substituent,
an aralkyl group having 7 to 20 carbon atoms and optionally having a halogen atom as a substituent,
an aryl group having 6 to 20 carbon atoms and optionally having a halogen atom as a substituent,
an alkoxy group having 1 to 20 carbon atoms and optionally having a halogen atom as a substituent,
an aralkyloxy group having 7 to 20 carbon atoms and optionally having a halogen atom as a substituent,
an aryloxy group having 6 to 20 carbon atoms and optionally having a halogen atom as a substituent,
a silyl group optionally having, as a substituent, a hydrocarbyl group or a halogenated hydrocarbyl group having 1 to 20 carbon atoms,
an amino group optionally having, as a substituent, a hydrocarbyl group or a halogenated hydrocarbyl group having 1 to 20 carbon atoms, or
a heterocyclic compound residue, (iv) $R^1$ and $R^3$, $R^2$ and $R^4$, $R^5$ and $R^6$, $R^5$ and $R^7$, or $R^7$ and $R^8$ may be taken together with each other to form a ring, wherein the ring may have a substituent;

$A^2$ represents a $—[Z(R(R^{12})(R^{12})]_n$-group, wherein Z represents a silicon atom, a germanium atom, a tin atom or a carbon atom, $R^{11}$ and $R^{12}$ are the same as, or different from each other, and represent a hydrogen atom,
an alkyl group having 1 to 20 carbon atoms and optionally having a halogen atom as a substituent,
a cycloalkyl group having 3 to 10 carbon atoms and optionally having a halogen atom as a substituent,
an aryl group having 6 to 20 carbon atoms and optionally having a halogen atom as a substituent, or
a silyl group optionally having, as a substituent, a hydrocarbyl group or a halogenated hydrocarbyl group having 1 to 20 carbon atoms, and
n represents 1, 2, 3 or 4, and when plural Zs, $R^{11}$s or $R^{12}$s exist, they may be the same as, or different from one another, X represents a hydrogen atom, a fluorine atom, a chlorine atom, a bromine atom, an iodine atom,
an alkyl group having 1 to 20 carbon atoms and optionally having a halogen atom as a substituent,
a cycloalkyl group having 3 to 10 carbon atoms and optionally having a halogen atom as a substituent,
an aralkyl group having 7 to 20 carbon atoms and optionally having a halogen atom as a substituent,
an aryl group having 6 to 20 carbon atoms and optionally having a halogen atom as a substituent,
an alkoxy group having 1 to 20 carbon atoms and optionally having a halogen atom as a substituent,
an aralkyloxy group having 7 to 20 carbon atoms and optionally having a halogen atom as a substituent,
an aryloxy group having 6 to 20 carbon atoms and optionally having a halogen atom as a substituent,
a silyl group optionally having, as a substituent, a hydrocarbyl group or a halogenated hydrocarbyl group having 1 to 20 carbon atoms,
an amino group optionally having, as a substituent, a hydrocarbyl group or a halogenated hydrocarbyl group having 1 to 20 carbon atoms,
a thiolate group optionally having, as a substituent, a hydrocarbyl group or a halogenated hydrocarbyl group having 1 to 20 carbon atoms, or
a carboxylate group optionally having, as a substituent, a hydrocarbyl group or a halogenated hydrocarbyl group having 1 to 20 carbon atoms, and when plural Xs exist, they are the same as, or different from each other, and adjacent Xs may be taken together with each other to form a ring;

k represents 1, 2 or 3; L represents a neutral Lewis base, and when plural Ls exist, plural Ls are the same as, or different from each other; m represents 0, 1, 2, 3 or 4; the sum of k and m is 2, 3 or 4.

[12] The transition metal compound according to the item [11], wherein Z is a silicon atom or a carbon atom.

[13] The transition metal compound according to the item [11], wherein $A^2$ is a $—CH_2CH_2—$ group.

[14] The transition metal compound according to the item [11], wherein

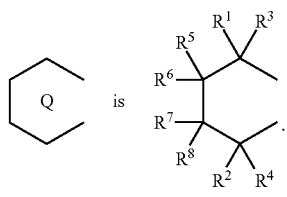

[15] The transition metal compound according to the item [11], wherein X is a fluorine atom, a chlorine atom, a bromine atom, an iodine atom, an alkyl group having 1 to 20 carbon atoms and optionally having a halogen atom as a substituent, an aralkyl group having 7 to 20 carbon atoms and optionally having a halogen atom as a substituent, an alkoxy group having 1 to 20 carbon atoms and optionally having a halogen atom as a substituent, an aryloxy group having 6 to 20 carbon atoms and optionally having a halogen atom as a substituent, or an amino group optionally having, as a substituent, a hydrocarbyl group or a halogenated hydrocarbyl group having 1 to 20 carbon atoms, and adjacent Xs may be taken together with each other to form a ring.

[16] The transition metal compound according to the item [11], wherein X is an aryloxy group having 6 to 20 carbon atoms and optionally having a halogen atom as a substituent.

[17] The transition metal compound according to the item [11], wherein M is a titanium atom, a zirconium atom or a hafnium atom.

[18] A compound represented by the formula (2-2):

(2-2)

wherein (i) $R^1$ and $R^2$ are the same as, or different from each other, and represent an alkyl group having 1 to 20 carbon atoms and optionally having a halogen atom as a substituent, a cycloalkyl group having 3 to 10 carbon atoms and optionally having a halogen atom as a substituent, an alkenyl group having 2 to 20 carbon atoms and optionally having a halogen atom as a substituent, an alkynyl group having 2 to 20 carbon atoms and optionally having a halogen atom as a substituent, an aralkyl group having 7 to 20 carbon atoms and optionally having a halogen atom as a substituent, or an aryl group having 6 to 20 carbon atoms and optionally having a halogen atom as a substituent, (ii) $R^3$ and $R^4$ are the same as, or different from each other, and represent a hydrogen atom, an alkyl group having 1 to 20 carbon atoms and optionally having a halogen atom as a substituent, a cycloalkyl group having 3 to 10 carbon atoms and optionally having a halogen atom as a substituent, an alkenyl group having 2 to 20 carbon atoms and optionally having a halogen atom as a substituent, an alkynyl group having 2 to 20 carbon atoms and optionally having a halogen atom as a substituent, an aralkyl group having 7 to 20 carbon atoms and optionally having a halogen atom as a substituent, or an aryl group having 6 to 20 carbon atoms and optionally having a halogen atom as a substituent, (iii) $R^5$ to $R^8$ are the same as, or different from one another, and represent a hydrogen atom, an alkyl group having 1 to 20 carbon atoms and optionally having a halogen atom as a substituent, a cycloalkyl group having 3 to 10 carbon atoms and optionally having a halogen atom as a substituent, an alkenyl group having 2 to 20 carbon atoms and optionally having a halogen atom as a substituent, an alkynyl group having 2 to 20 carbon atoms and optionally having a halogen atom as a substituent, an aralkyl group having 7 to 20 carbon atoms and optionally having a halogen atom as a substituent, an aryl group having 6 to 20 carbon atoms and optionally having a halogen atom as a substituent, an alkoxy group having 1 to 20 carbon atoms and optionally having a halogen atom as a substituent, an aralkyloxy group having 7 to 20 carbon atoms and optionally having a halogen atom as a substituent, an aryloxy group having 6 to 20 carbon atoms and optionally having a halogen atom as a substituent, a silyl group optionally having, as a substituent, a hydrocarbyl group or a halogenated hydrocarbyl group having 1 to 20 carbon atoms, an amino group optionally having, as a substituent, a hydrocarbyl group or a halogenated hydrocarbyl group having 1 to 20 carbon atoms, or a heterocyclic compound residue, (iv) $R^1$ and $R^3$, $R^2$ and $R^4$, W and $R^6$, $R^5$ and $R^7$, or $R^7$ and $R^8$ may be taken together with each other to form a ring, wherein the ring may have a substituent;

A² represents a —[Z(R¹¹)(R¹²)]ₙ-group, wherein Z represents a silicon atom, a germanium atom, a tin atom or a carbon atom, R¹¹ and R¹² are the same as, or different from each other, and represent a hydrogen atom,
an alkyl group having 1 to 20 carbon atoms and optionally having a halogen atom as a substituent,
a cycloalkyl group having 3 to 10 carbon atoms and optionally having a halogen atom as a substituent,
an aryl group having 6 to 20 carbon atoms and optionally having a halogen atom as a substituent, or
a silyl group optionally having, as a substituent, a hydrocarbyl group or a halogenated hydrocarbyl group having 1 to 20 carbon atoms; and
n represents 1, 2, 3 or 4, and when plural Zs, R¹¹s or R¹²s exist, they are the same as, or different from one another.

[19] The compound according to the item [18], wherein Z is a silicon atom or a carbon atom.

[20] The compound according to the item [18], wherein A² is a —CH₂CH₂— group.

[21] The compound according to the item [18], wherein

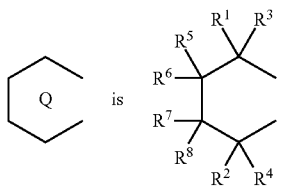

[22] A process for producing a catalyst for olefin polymerization comprising a step of bringing the transition metal compound according to the item [11] into contact with a co-catalytic component for activation.

[23] A process for producing an olefin polymer comprising a step of polymerizing an olefin in the presence of a catalyst for olefin polymerization produced by the production process according to the item [22].

[24] The production process according to the item [23], wherein the olefin is a combination of ethylene and α-olefin.

DETAILED DESCRIPTION OF THE INVENTION

A transition metal atom represented by M in the formula (1) is preferably a transition metal atom of the Group 3, 4, or the Group lanthanide, more preferably a titanium atom, a zirconium atom or a hafnium atom.

R¹ and R² are preferably an alkyl group having 1 to 20 carbon atoms and optionally having a halogen atom as a substituent, a cycloalkyl group having 3 to 10 carbon atoms and optionally having a halogen atom as a substituent, an aralkyl group having 7 to 20 carbon atoms and optionally having a halogen atom as a substituent, an aryl group having 6 to 20 carbon atoms and optionally having a halogen atom as a substituent, more preferably an alkyl group having 1 to 20 carbon atoms and optionally having a halogen atom as a substituent, or an aralkyl group having 7 to 20 carbon atoms and optionally having a halogen atom as a substituent.

R³ and R⁴ are preferably a hydrogen atom, an alkyl group having 1 to 20 carbon atoms and optionally having a halogen atom as a substituent, a cycloalkyl group having 3 to 10 carbon atoms and optionally having a halogen atom as a substituent, an aralkyl group having 7 to 20 carbon atoms and optionally having a halogen atom as a substituent, or an aryl group having 6 to 20 carbon atoms and optionally having a halogen atom as a substituent, more preferably a hydrogen atom, an alkyl group having 1 to 20 carbon atoms and optionally having a halogen atom as a substituent, or an aralkyl group having 7 to 20 carbon atoms and optionally having a halogen atom as a substituent.

R⁵ to R⁸ are preferably a hydrogen atom, an alkyl group having 1 to 20 carbon atoms and optionally having a halogen atom as a substituent, a cycloalkyl group having 3 to 10 carbon atoms and optionally having a halogen atom as a substituent, an alkenyl group having 2 to 20 carbon atoms and optionally having a halogen atom as a substituent, an alkynyl group having 2 to 20 carbon atoms and optionally having a halogen atom as a substituent, an aralkyl group having 7 to 20 carbon atoms and optionally having a halogen atom as a substituent, or an aryl group having 6 to 20 carbon atoms and optionally having a halogen atom as a substituent, more preferably an alkyl group having 1 to 20 carbon atoms and optionally having a halogen atom as a substituent, a cycloalkyl group having 3 to 10 carbon atoms and optionally having a halogen atom as a substituent, an aralkyl group having 7 to 20 carbon atoms and optionally having a halogen atom as a substituent, or an aryl group having 6 to 20 carbon atoms and optionally having a halogen atom as a substituent.

A¹ represents a —[C(R⁹)(R¹⁰)]ₙ-group, R⁹ and R¹⁰ are the same as, or different from each other, and are a hydrogen atom, a halogen atom, an alkyl group having 1 to 20 carbon atoms and optionally having a halogen atom as a substituent, a cycloalkyl group having 3 to 10 carbon atoms and optionally having a halogen atom as a substituent, an aryl group having 6 to 20 carbon atoms and optionally having a halogen atom as a substituent, or a silyl group optionally having, as a substituent, a hydrocarbyl group or a halogenated hydrocarbyl group having 1 to 20 carbon atoms, and when plural R⁹s or R¹⁰s exist, respectively, they are the same as, or different from each other, and n is 1, 2, 3 or 4.

Z in a —[Z(R¹¹)(R¹²)]ₙ-group of A² represents a silicon atom, a germanium atom, a tin atom or a carbon atom, preferably a silicon atom or a carbon atom.

R¹¹ and R¹² are preferably a hydrogen atom, an alkyl group having 1 to 20 carbon atoms and optionally having a halogen atom as a substituent, an aryl group having 6 to 20 carbon atoms and optionally having a halogen atom as a substituent, or a silyl group optionally having, as a substituent, a hydrocarbyl group or a halogenated hydrocarbyl group having 1 to 20 carbon atoms, more preferably a hydrogen atom, or an alkyl group having 1 to 20 carbon atoms and optionally having a halogen atom as a substituent.

n represents 1, 2, 3 or 4, preferably 1 or 2.

X is preferably a fluorine atom, a chlorine atom, a bromine atom, an iodine atom, an alkyl group having 1 to 20 carbon atoms and optionally having a halogen atom as a substituent, a cycloalkyl group having 3 to 10 carbon atoms and optionally having a halogen atom as a substituent, an aralkyl group having 7 to 20 carbon atoms and optionally having a halogen atom as a substituent, an aryl group having 6 to 20 carbon atoms and optionally having a halogen atom as a substituent, an alkoxy group having 1 to 20 carbon atoms and optionally having a halogen atom as a substituent, an aralkyloxy group having 7 to 20 carbon atoms and optionally having a halogen atom as a substituent, an aryloxy group having 6 to 20 carbon atoms and optionally having a halogen atom as a substituent, a silyl group optionally having, as a substituent, a hydrocarbyl group or a halogenated hydrocarbyl group having 1 to 20 carbon atoms, or an amino group optionally having, as a substituent, a hydrocarbyl group or a halogenated hydrocarbyl group having 1 to 20 carbon atoms, more preferably a chlorine atom, a bromine atom, an iodide atom, an alkyl group having 1 to 20 carbon atoms and optionally having a halogen atom as a substituent, an aralkyl group having 7 to 20 carbon atoms and optionally having a halogen atom as a substituent, an aryl group having 6 to 20 carbon atoms and optionally having a halogen atom as a substituent, an alkoxy group having 1 to 20 carbon atoms and optionally having a halogen atom as a substituent, an aralkyloxy group having 7 to 20 carbon atoms and optionally having a halogen atom as a substituent, an aryloxy group having 6 to 20 carbon atoms and optionally having a halogen atom as a substituent, an amino group optionally having, as a substituent, a hydrocarbyl group or a halogenated hydrocarbyl group having 1 to 20 carbon atoms, particularly preferably a chlorine atom, an alkyl group having 1 to 20 carbon atoms and optionally having a halogen atom as a substituent, an aralkyl group having 7 to 20 carbon atoms and optionally having a halogen atom as a substituent, an alkoxy group having 1 to 20 carbon atoms and optionally having a halogen atom as a substituent, an aryloxy group having 6 to 20 carbon atoms and optionally having a halogen atom as a substituent, or an amino group optionally having, as a substituent, a hydrocarbyl group or a halogenated hydrocarbyl group having 1 to 20 carbon atoms.

k represents 1, 2, 3 or 4, preferably 1 or 2.

Examples of L may include ethers, amines and thioethers, and specific examples thereof may include tetrahydrofuran, diethyl ether, 1,4-dioxane and pyridine.

The sum of k and m is 2, 3, or 4, preferably 2 or 4.

Examples of the alkyl group having 1 to 20 carbon atoms and optionally having a halogen atom as a substituent may include a perfluoromethyl group, a perfluoroethyl group, a perfluoropropyl group, a perfluorobutyl group, a perfluoropentyl group, a perfluorohexyl group, a perfluorooctyl group, a perfluorododecyl group, a perfluoropentadecyl group, a perfluoroeicosyl group, a methyl group, an ethyl group, a n-propyl group, an isopropyl group, a n-butyl group, a sec-butyl group, an isobutyl group, a n-pentyl group, a neopentyl group, a n-hexyl group, a n-heptyl group, a n-octyl group, a n-decyl group, a n-dodecyl group, a n-pentadecyl group, and a n-eicosyl group. Among them, preferable is an alkyl group having 1 to 4 carbon atoms, and more preferable is a methyl group, an ethyl group, a n-propyl group, an isopropyl group, or a n-butyl group.

Examples of the cycloalkyl group having 3 to 10 carbon atoms and optionally having a halogen atom as a substituent may include a cyclopropyl group, a cyclobutyl group, a cyclopentyl group, a cyclohexyl group, a cyclohepyl group and a cyclooctyl group. Among them, preferable is a cycloalkyl group having 3 to 8 carbon atoms, and more preferable is a cyclopropyl group, a cyclopentyl group, or a cyclohexyl group.

Examples of the aryl group having 6 to 20 carbon atoms and optionally having a halogen atom as a substituent may include a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, an isobutylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group, an anthracenyl group, a 2-fluorophenyl group, a 3-fluorophenyl group, a 4-fluorophenyl group, a pentafluorophenyl group, a 2-trifluoromethanephenyl group, a 3-triflulorometanephenyl group, a 4-trifluoromethanephenyl group, a 2,3-difluorophenyl group, a 2,4-fluorophenyl group, a 2,5-difluorophenyl group, a 2-chlorophenyl group, a 2,3-dichlorophenyl group, a 2,4-dichlorophenyl group, a 2,5-dichlorophenyl group, a 2-bromophenyl group, a 3-bromophenyl group, a 4-bromophenyl group, a 2,3-dibromophenyl group, a 2,4-dibromophenyl group, and a 2,5-dibromophenyl group. Among them, preferable is an aryl group having 6 to 10 carbon atoms, and more preferable is a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, or a pentafluorophenyl group.

Examples of the silyl group optionally having, as a substituent, a hydrocarbyl group or a halogenated hydrocarbyl group having 1 to 20 may include a trimethylsilyl group, a triethylsilyl group, a tri-n-propyl group, a tri-iso-propylsilyl group, a tri-n-butylsilyl group, a tri-iso-butylsilyl group, a tert-butyldimethylsilyl group, a tert-butyldiphenylsilyl group, and a triphenylsilyl group. Among them, preferable is a hydrocarbyl group having 3 to 6 carbon atoms, and more preferable is a trimethylsilyl group, a triethyl group or a tert-butyldimethylsilyl group.

Examples of the alkoxy group having 1 to 20 carbon atoms and optionally having a halogen atom as a substituent may include a perfluoromethoxy group, a perfluoroethoxy group, a perfluoropropoxy group, a perfluorobutoxy group, a perfluoropentyloxy group, a perfluorohexyloxy group, a perfluorooctyloxy group, a perfluorododecyloxy group, a perfluoropentadecyloxy group, a perfluoroeicosyloxy group, a methoxy group, an ethoxy group, a n-propoxy group, an isopropoxy group, a n-butoxy group, a sec-butoxy group, an isobutoxy group, a n-pentyloxy group, a neopentyloxy group, a n-hexyloxy group, a n-heptyloxy group, a n-octyloxy group, a n-decyloxy group, a n-dodecyloxy group, a n-pentadecyloxy group, and a n-eicosyloxy group. Among them, preferable is an alkoxy group having 1 to 4 carbon atoms, and more preferable is a methoxy group, an ethoxy group, a n-propoxy group, an isopropoxy group, or a n-butoxy group.

Examples of the aryloxy group having 6 to 20 carbon atoms and optionally having a halogen atom as a substituent may include a phenoxy group, a 2,3,4-trimethylphenoxy group, a 2,3,5-trimethylphenoxy group, a 2,3,6-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, a 2-fluorophenoxy group, a 3-fluorophenoxy group, a 4-fluorophenoxy group, a pentafluorophenoxy group, a 2-trifluoromethylphenoxy group, a 3-trifluoromethylphenoxy group, a 4-trifluoromethylphenoxy group, a 2,3-difluorophenoxy group, a 2,4-fluorophenoxy group, a 2,5-difluorophenoxy group, a 2-chlorophenoxy group, a 2,3-dichlorophenoxy group, a 2,4-dichlorophenoxy group, a 2,5-dichlorophenoxy group, a 2-bromophenoxy group, a 3-bromophenoxy group, a 4-bromophenoxy group, a 2,3-dibromophenoxy group, a 2,4-dibromophenoxy group, and a 2,5-dibromophenoxy group. Among them, preferable is an aryloxy group having 6 to 10 carbon atoms, and more preferable is a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, or a pentafluorophenoxy group.

Examples of the heterocyclic compound residue may include a pyridinyl group, a 4,6-dimethylpyridinyl group, a 2,6-dimethylpyridinyl group, a furanyl group, a 5-methylfuranyl group, 2,5-dimethylfuranyl group, a thiophenyl group, a 5-methylthiophenyl group, and a 2,5-dimethylthiophenyl group. Among them, preferable is a 4,6-dimethylpyridinyl group, a 2,6-dimethylpyridinyl group, a 5-methylfuranyl group, a 2,5-dimethylfuranyl group, a 5-methylthiophenyl group or a 2,5-dimethylthiophenyl group.

Examples of the alkenyl group having 2 to 20 carbon atoms and optionally having a halogen atom as a substituent may include a vinyl group, an allyl group, a propenyl group, a 2-methyl-2-propenyl group, a homoallyl group, a pentenyl group, a hexenyl group, a heptenyl group, an octenyl group, a nonenyl group, and a decenyl group. Among them, preferable is an alkenyl group having 3 to 6 carbon atoms, and more preferable is an allyl group, or a homoallyl group.

Examples of the alkynyl group having 2 to 20 carbon atoms and optionally having a halogen atom as a substituent may include an ethynyl group, a phenylacetyl group, a methylacetyl group, an ethylacetyl group, a n-propylacetyl group, a sec-propylacetyl group, a tert-butylacetyl group, a n-butylacetyl group and an iso-butylacetyl group. Among them, preferable is an alkynyl group having 3 to 8 carbon atoms, and more preferable is a phenylacetyl group or a tert-butylacetyl group.

Examples of the aralkyl group having 7 to 20 carbon atoms and optionally having a halogen atom as a substituent may include a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (3,5-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl) methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl) methyl group, a (tert-butylphenyl)methyl group, an (isobutylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, a naphthylmethyl group, and an anthracenylmethyl group. Among them, preferable is an aralkyl group having 7 to 12 carbon atoms, and more preferable is a benzyl group.

Examples of the aralkyloxy group having 7 to 20 carbon atoms and optionally having a halogen atom as a substituent may include a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl) methoxy group, a (2,6-dimethylphenyl)methoxy group, a (3,4-dimethylphenyl)methoxy group, a (3,5-dimethylphenyl) methoxy group, a (2,3,4-trimethylphenyl)methoxy group, a (2,3,5-trimethylphenyl)methoxy group, a (2,3,6-trimethylphenyl)methoxy group, a (2,4,5-trimethylphenyl)methoxy group, a (2,4,6-trimethylphenyl)methoxy group, a (3,4,5-trimethylphenyl)methoxy group, a (2,3,4,5-tetramethylphenyl) methoxy group, a (2,3,4,6-tetramethylphenyl)methoxy group, a (2,3,5,6-tetramethylphenyl)methoxy group, a (pentamethylphenyl)methoxy group, an (ethylphenyl)methoxy group, a (n-propylphenyl)methoxy group, an (isopropylphenyl)methoxy group, a (n-butylphenyl)methoxy group, a (sec-butylphenyl)methoxy group, a (tert-butylphenyl)methoxy group, a (n-hexylphenyl)methoxy group, a (n-octylphenyl)methoxy group, a (n-decylphenyl)methoxy group, a (n-tetradecylphenyl)methoxy group, a naphthylmethoxy group, and an anthracenylmethoxy group. Among them, preferable is an aralkyloxy group having 7 to 12 carbon atoms, and more preferable is a benzyloxy group.

Examples of the amino group optionally having, as a substituent, a hydrocarbyl group or a halogenated hydrocarbyl group having 1 to 20 carbon atoms may include a dimethylamino group, a diethylamino group, a di-n-butylamino group, a di-n-propylamino group, a diisopropylamino group, a dibenzylamino group and a diphenylamino group. Among them, preferable is an amino group optionally having, as a substituent, a hydrocarbyl group having 2 to 14 carbon atoms, and more preferable is a dimethylamino group, a diethylamino group, a di-n-propylamino group, a diisopropylamino group or a dibenzylamino group.

Examples of the thiolate group optionally having, as a substituent, a hydrocarbyl group or a halogenated hydrocarbyl group having 1 to 20 carbon atoms may include a thiophenoxy group, a 2,3,4-trimethylthiophenoxy group, a 2,3,5-trimethylthiophenoxy group, a 2,3,6-trimethylthiophenoxy group, a 2,4,6-trimethylthiophenoxy group, a 3,4,5-trimethylthiophenoxy group, a 2,3,4,5-tetramethylthiophenoxy group, a 2,3,4,6-tetramethylthiophenoxy group, a 2,3,5,6-tetramethylphenoxy group, a pentamethylphenoxy group, a 2-fluorothiophenoxy group, a 3-fluorothiophenoxy group, a 4-fluorophenoxy group, a pentafluorothiophenoxy group, a 2-trifluoromethylthiophenoxy group, a 3-trifluoromethylthiophenoxy group, a 4-trifluoromethylthiophenoxy group, a 2,3-difluorothiophenoxy group, a 2,4-fluorothiophenoxy group, a 2,5-difluorothiophenoxy group, a 2-chlorothiophenoxy group, a 2,3-dichlorothiophenoxy group, a 2,4-dichlorothiophenoxy group, a 2,5-dichlorothiophenoxy group, a 2-bromothiophenoxy group, a 3-bromothiophenoxy group, a 4-bromothiophenoxy group, a 2,3-dibromothiophenoxy group, a 2,4-dibromothiophenoxy group, and a 2,5-dibromothiophenoxy group. Among them, preferable is a thiolate group optionally having, as a substituent, a hydrocarbyl group having 6 to 12 carbon atoms, and more preferable is a thiophenoxy group, a 2,4,6-trimethylthiophenoxy group, a 3,4,5-trimethylthiophenoxy group, a 2,3,4,5-tetramethylthiophenoxy group, a 2,3,4,6-tetramethylthiophenoxy group, a 2,3,5,6-tetramethylthiophenoxy group, a pentamethylthiophenoxy group, or a pentafluorothiophenoxy group.

Examples of the carboxylate group optionally having, as a substituent, a hydrocarbyl group or a halogenated hydrocarbyl group having 1 to 20 carbon atoms may include an acetate group, a propionate group, a butyrate group, a pentanate group, a hexanoate group, a 2-ethylhexanoate group and a trifluoroacetate group. Among them, preferable is a carboxylate group optionally having, as a substituent, a hydrocarbyl group having 2 to 10 carbon atoms, and more preferable is an acetate group, a propionate group, 2-ethylhexanoate group or a trifluoroacetate group.

$R^1$ and $R^3$, or $R^2$ and $R^4$ in the formula (1) may be taken together, respectively, to form a 3- to 10-membered hydrocarbyl ring, and the ring may have a substituent. Examples of the ring may include a cyclopropane ring, a cyclobutane group, a cyclopentane ring, a cyclohexane ring, a cycloheptane ring and a cyclooctane ring. Among them, preferable is a cyclopropane ring, a cyclopentane ring, or a cyclohexane ring.

$R^5$ and $R^6$, $R^5$ and $R^7$, or $R^7$ and $R^8$ in the formula (1) may be taken together, respectively, to form a 3- to 10-membered hydrocarbyl ring or a 3- to 10-membered heterocyclic ring. The ring may have a substituent. Examples of the hydrocarbyl ring may include a cyclopropane ring, a cyclobutane ring, a cyclopentane ring, a cyclohexane ring, a cycloheptane ring, a cyclooctane ring, a benzene ring and a naphthalene ring. Among them, preferable is a cyclopropane ring, a cyclopentane ring, a cyclohexane ring, a benzene ring or a naphthalene ring. Examples of the heterocyclic ring may include a furan ring, a 2,5-dimethylfuran ring, a thiophene ring, a 2,5-dimethylthiophene ring, and a pyridine ring. Among them, preferable is a 2,5-dimethylfuran ring, a 2,5-dimethylthiophene ring, or a pyridine ring.

Examples of the transition metal compound represented by the formula (1-1) may include the following compounds, and compounds in which the zirconium atom of the following compounds is changed to a titanium atom or a hafnium atom, and compounds in which the phenoxy group of the following compounds is changed to a methyl group, an ethyl group, a dimethylamino group, a methoxy group, an ethoxy group, or a chlorine atom.

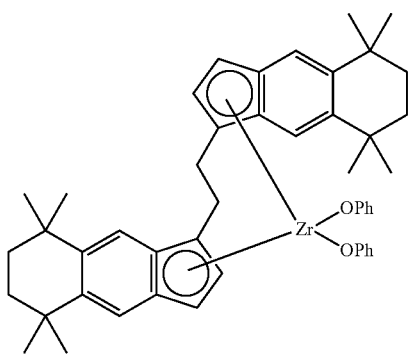

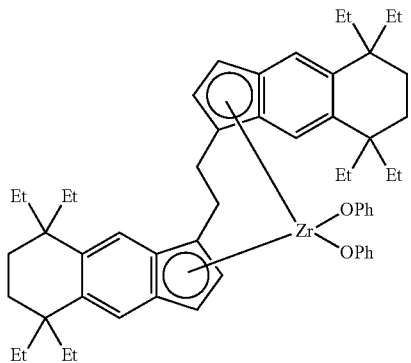

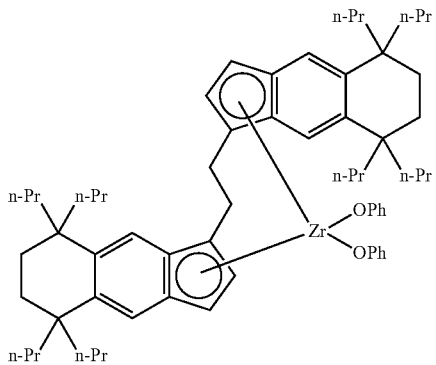

-continued

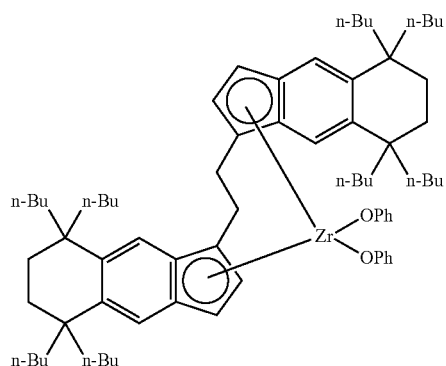

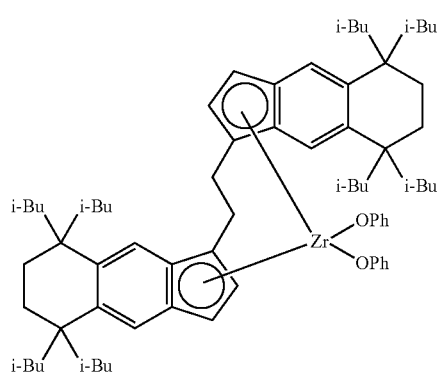

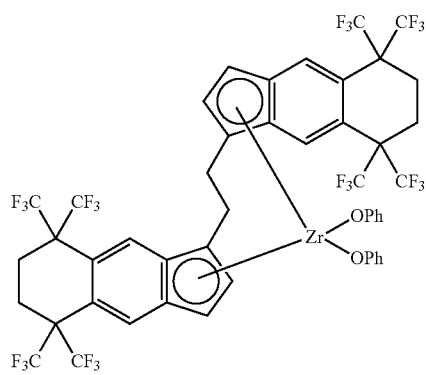

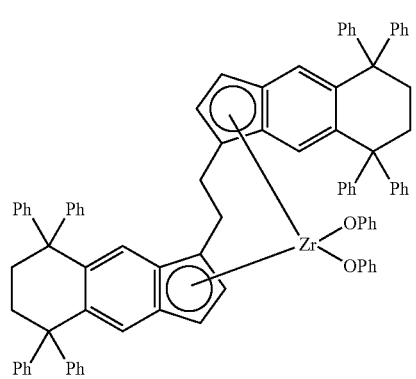

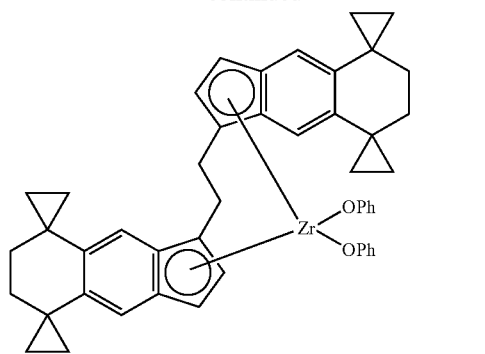
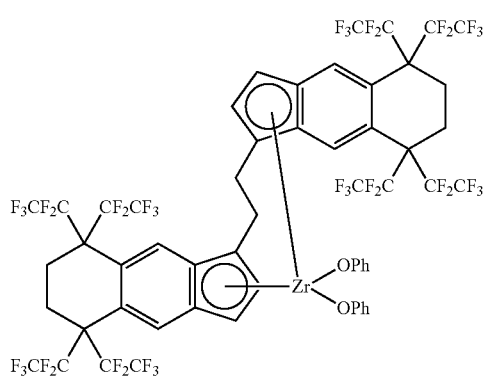
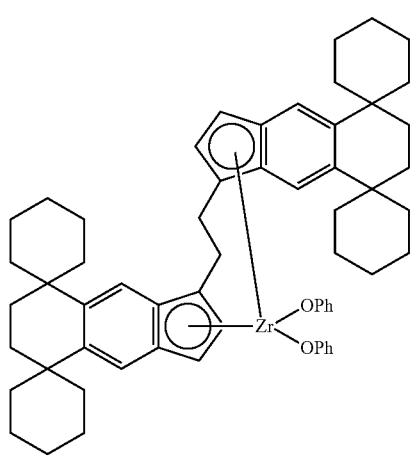
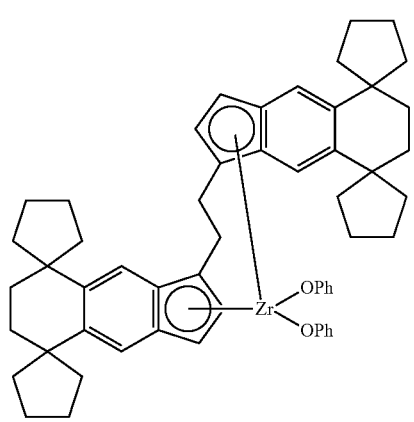
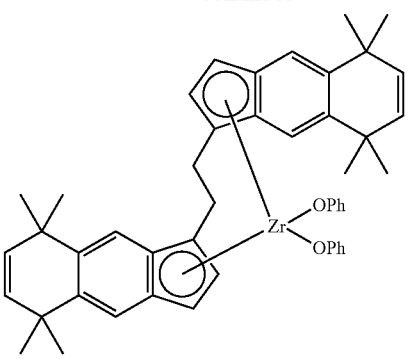
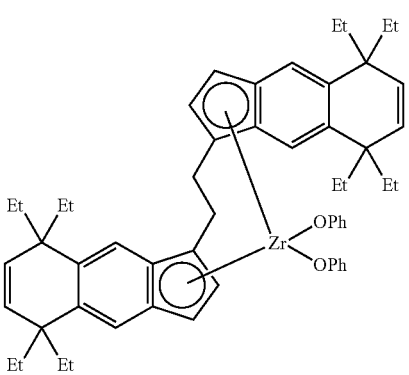
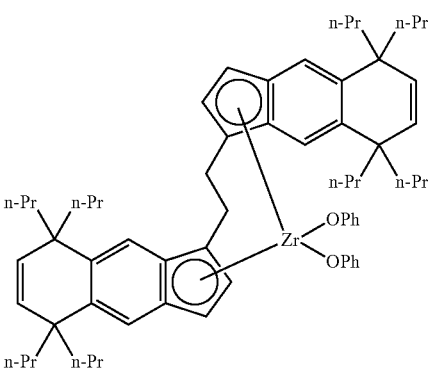
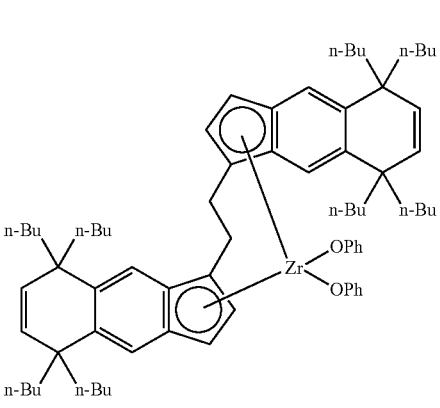

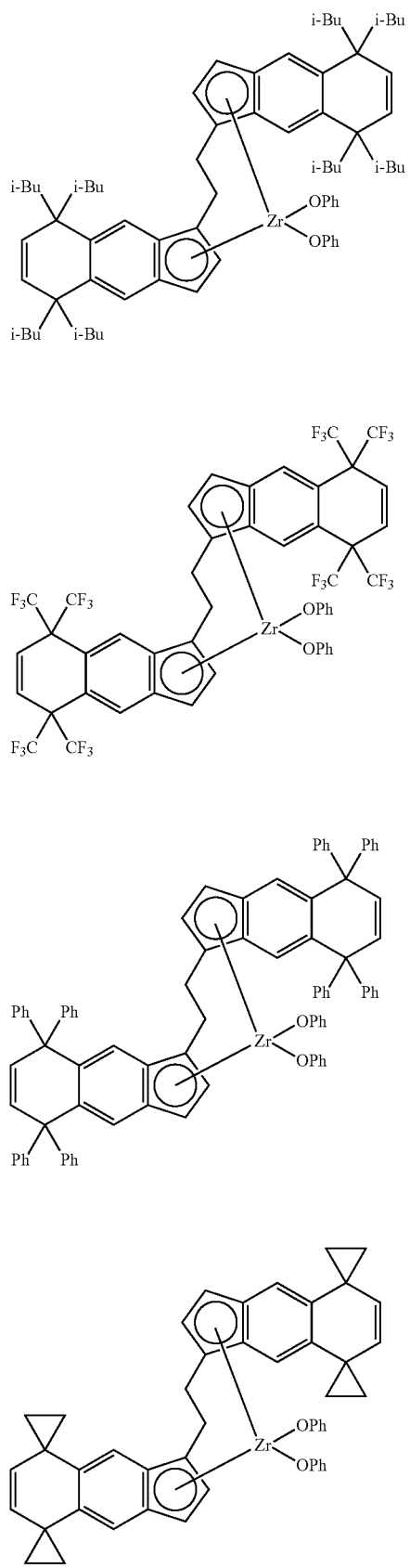
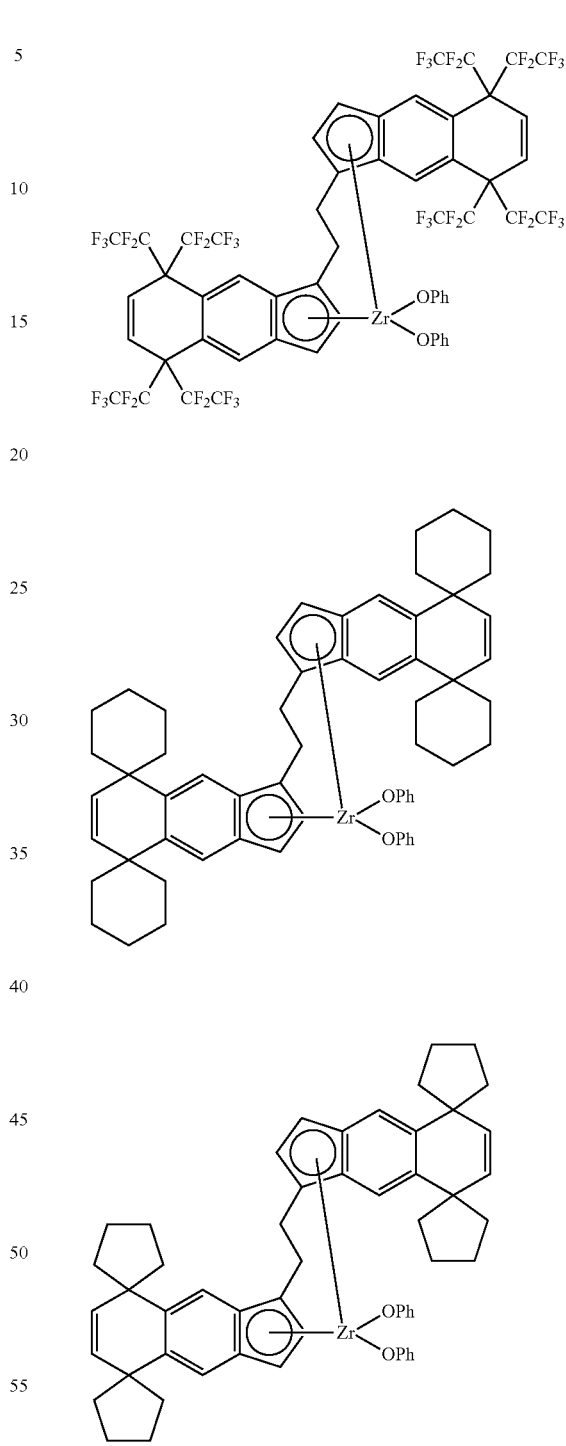

Examples of the transition metal compound represented by the formula (1-2) may include the following compounds, compounds in which the zirconium atom of the following compounds is changed to a titanium atom or a hafnium atom, and compounds in which the phenoxy group of the following compounds is changed to a methyl group, an ethyl group, a dimethylamino group, a methoxy group, an ethoxy group, or a chlorine atom.

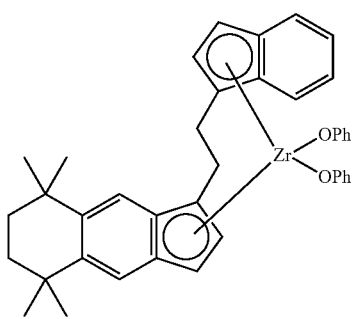
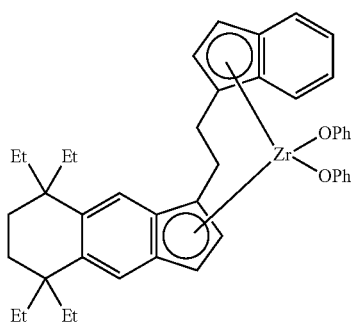
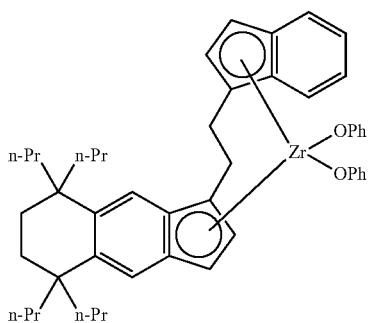
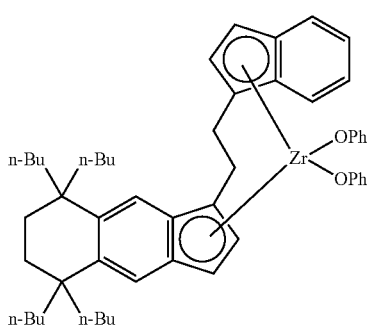
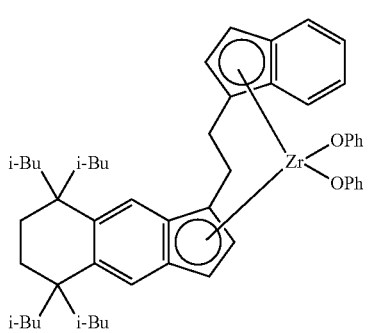
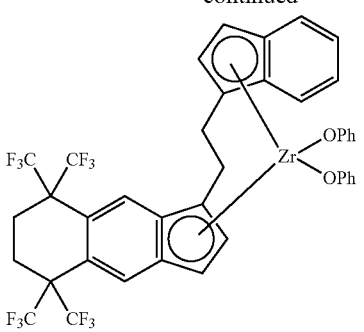
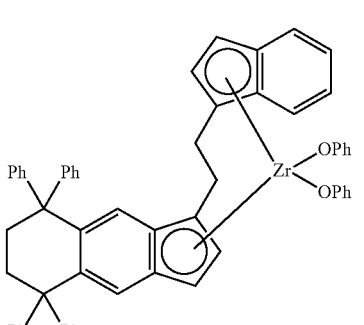
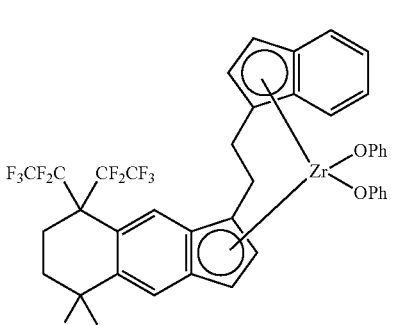
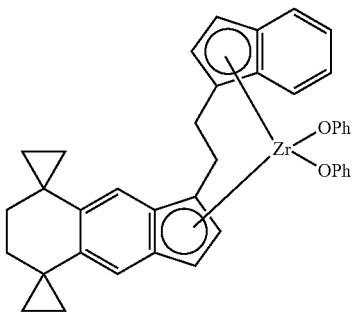
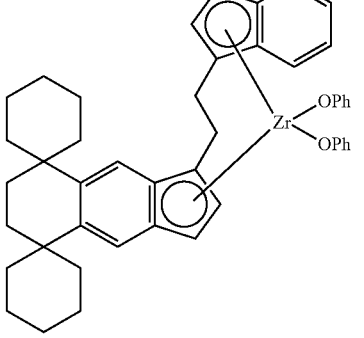

-continued
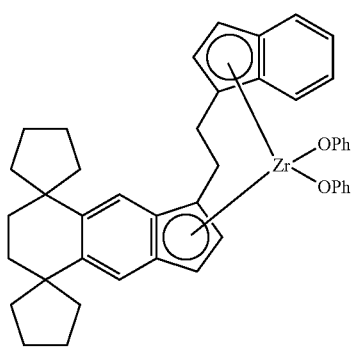
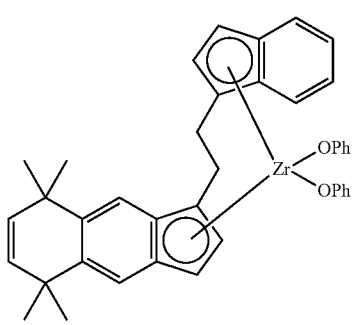
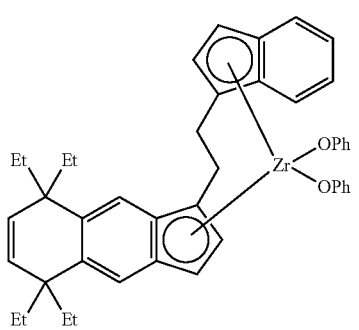
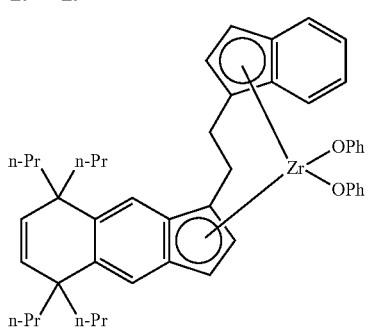
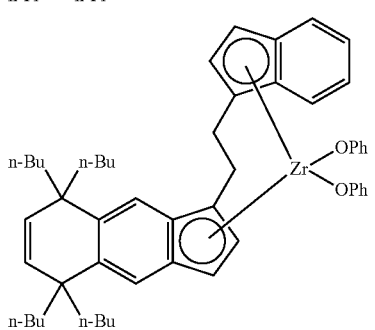
-continued
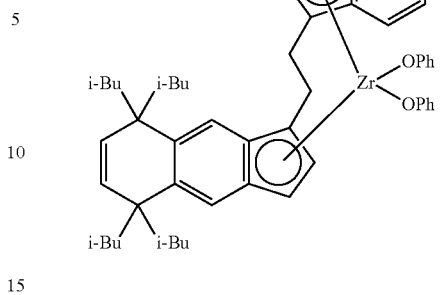
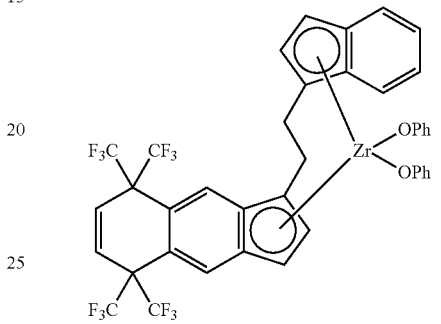
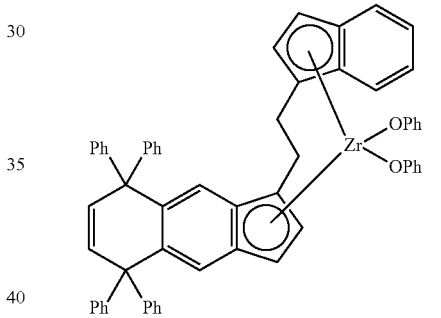
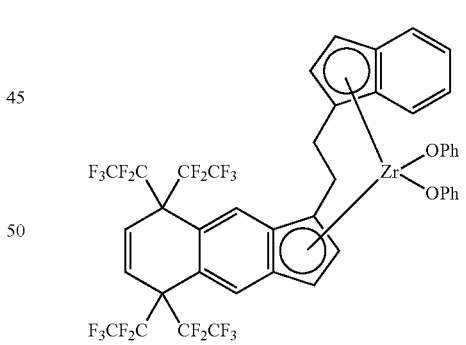
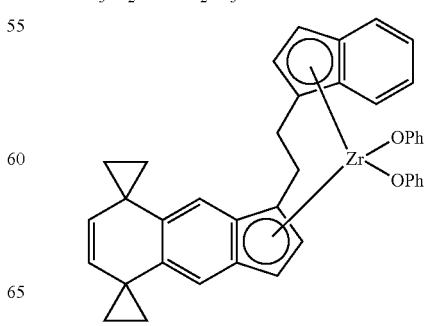

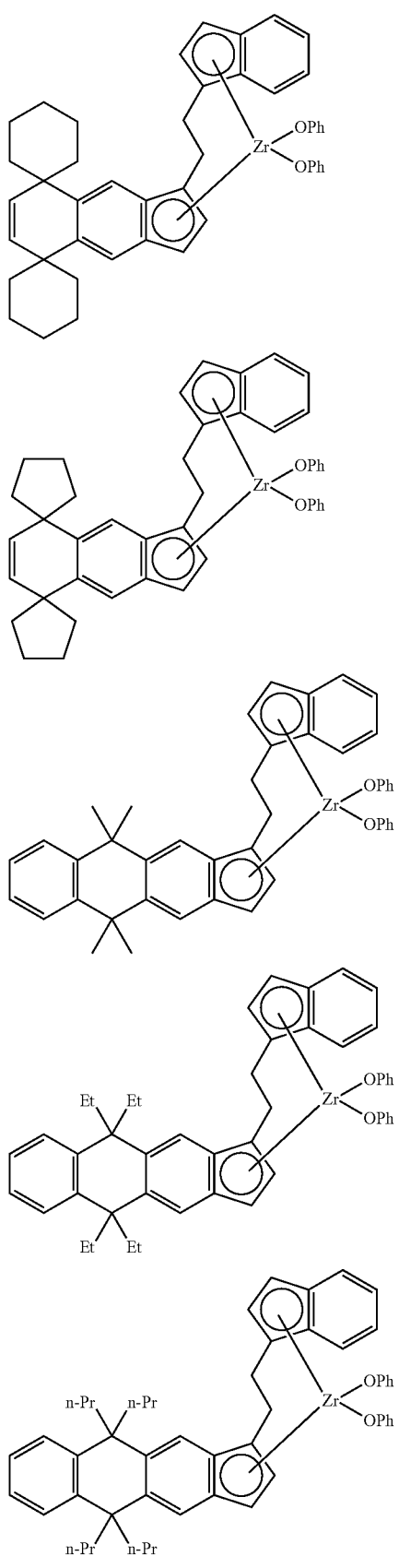
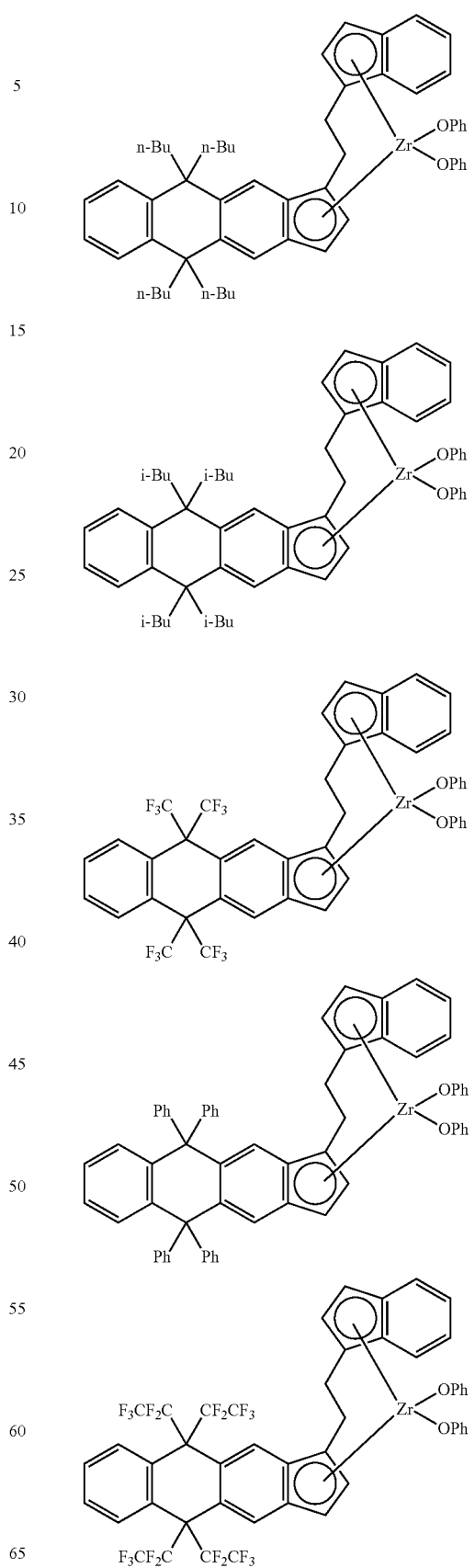

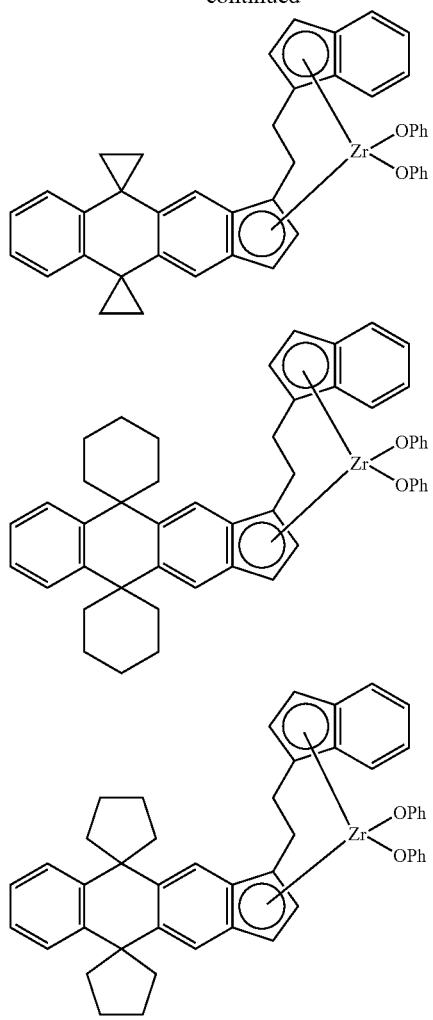
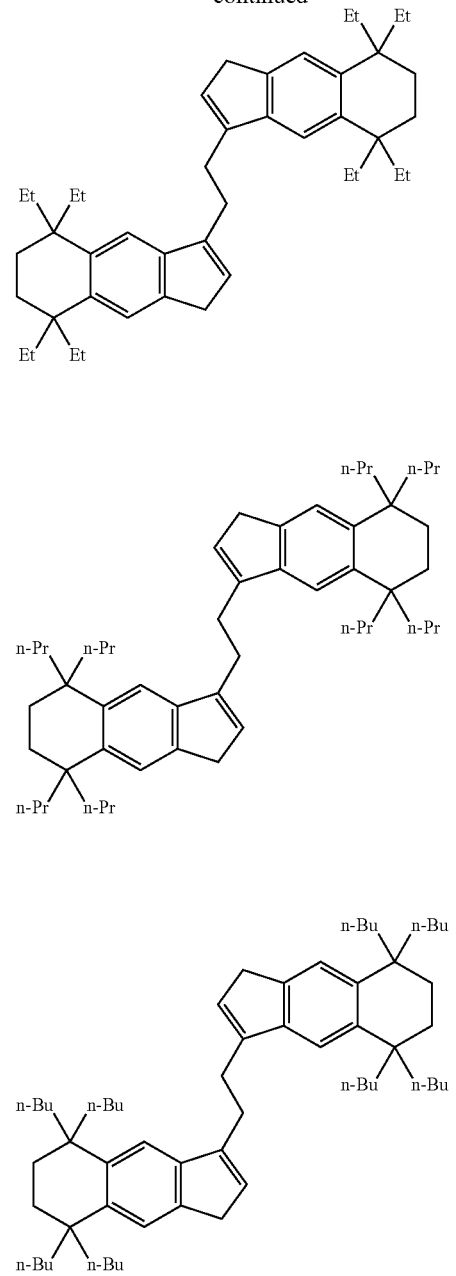
Among the transition metal compounds represented by the formulas (1-1) and (1-2), the transition metal compound represented by the formula (1-2) is preferable.
All symbols in the formula (2) have the same meanings as those of symbols in the formula (1), and examples of the compound represented by the formula (2-1) may include the following compounds.
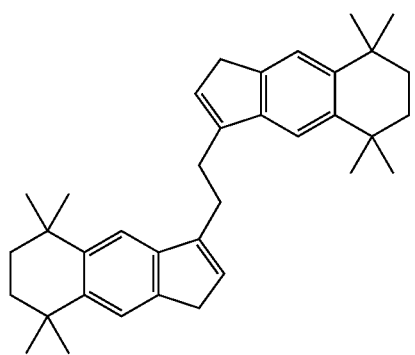
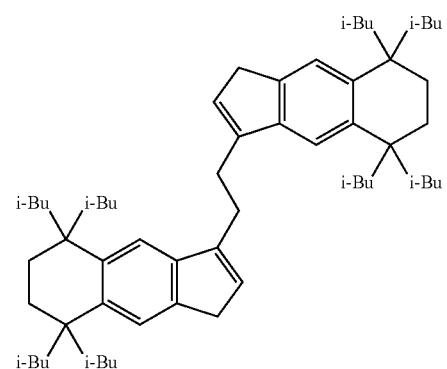

39
-continued
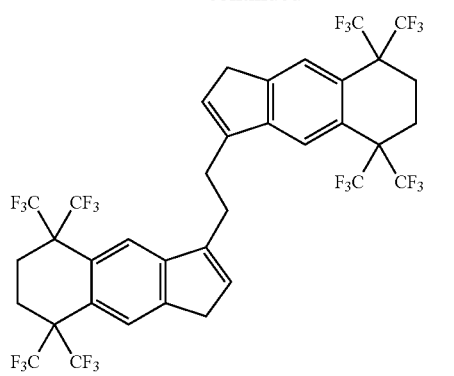
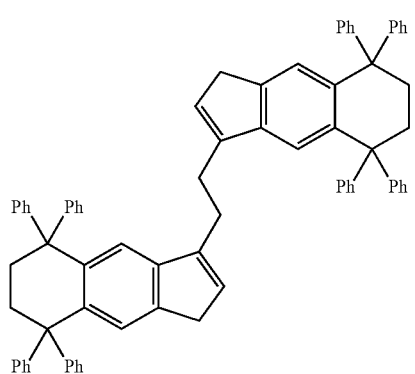
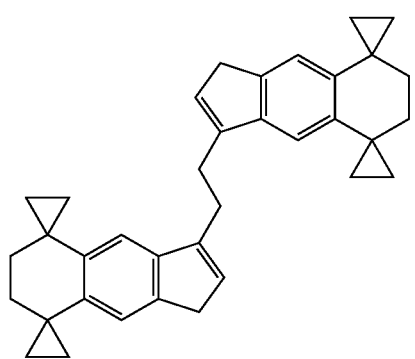
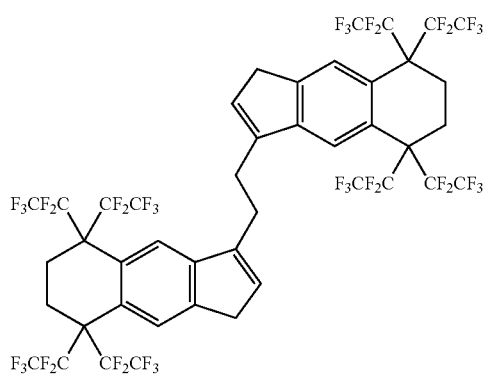
40
-continued
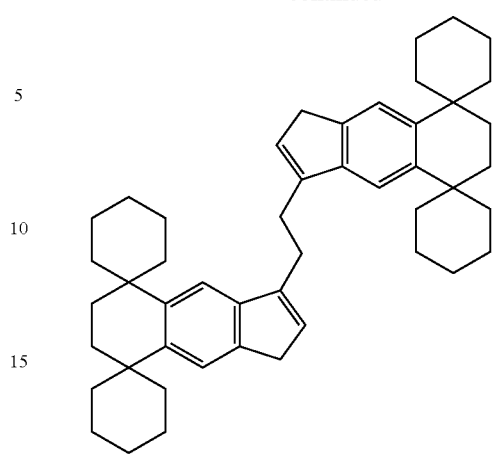
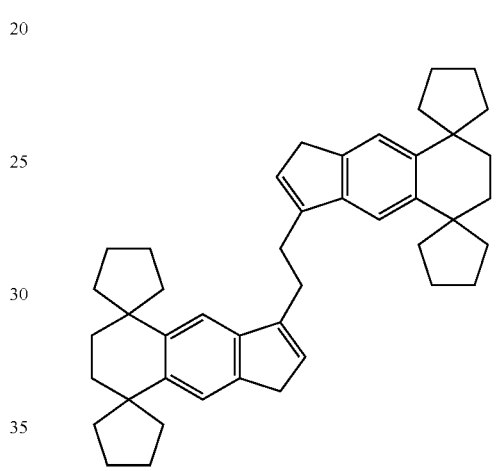
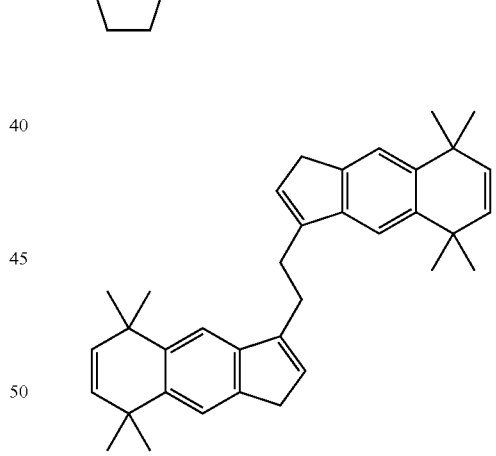
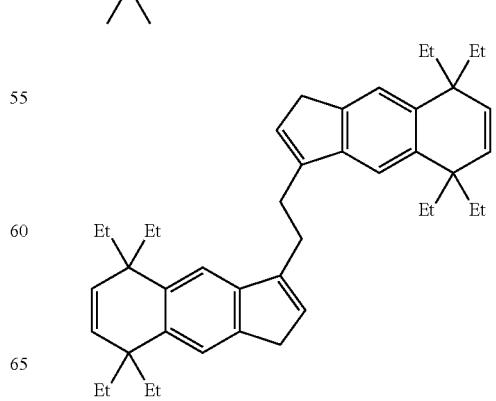

41
-continued
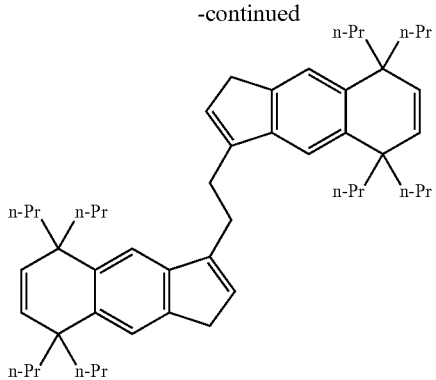
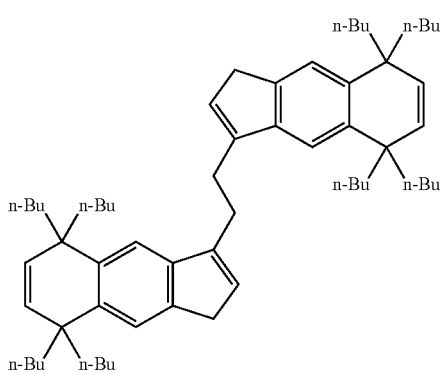
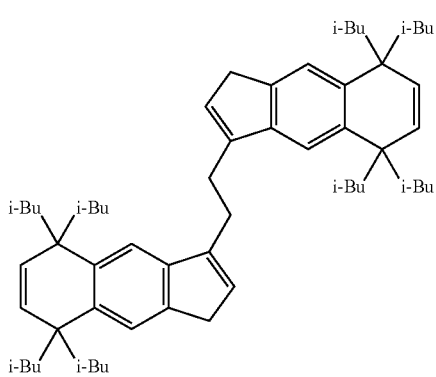
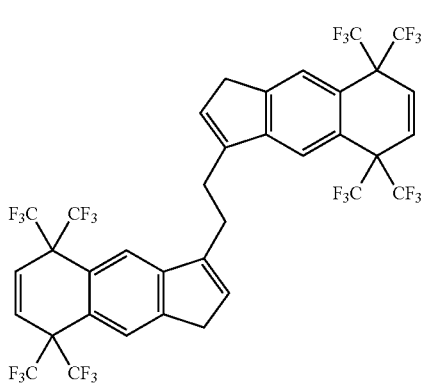
42
-continued
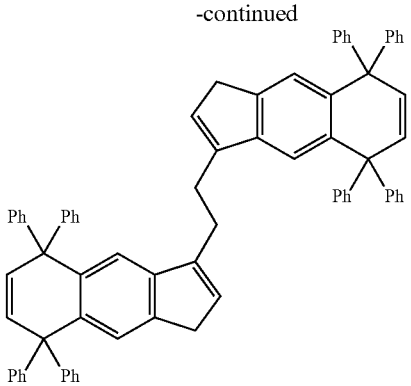
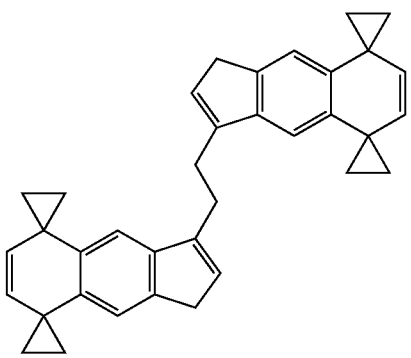
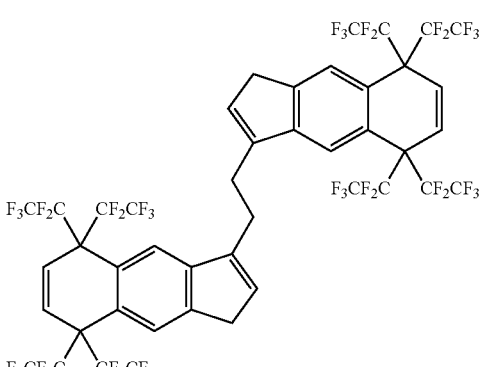
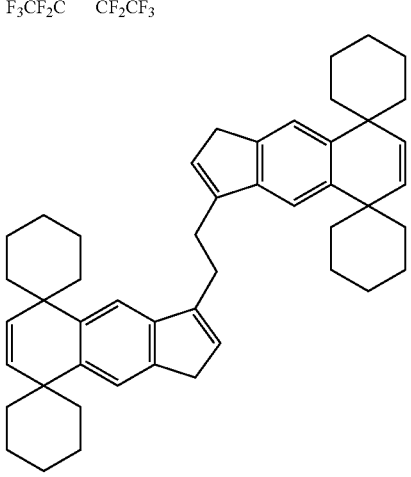

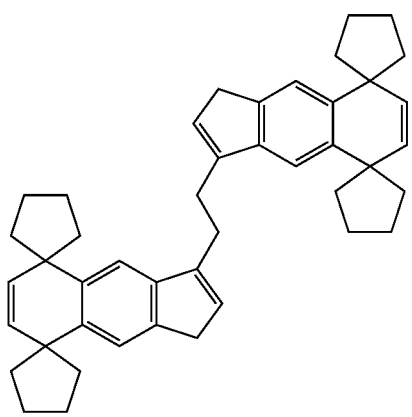
Examples of the compound represented by the formula (2-2) may include the following compounds.
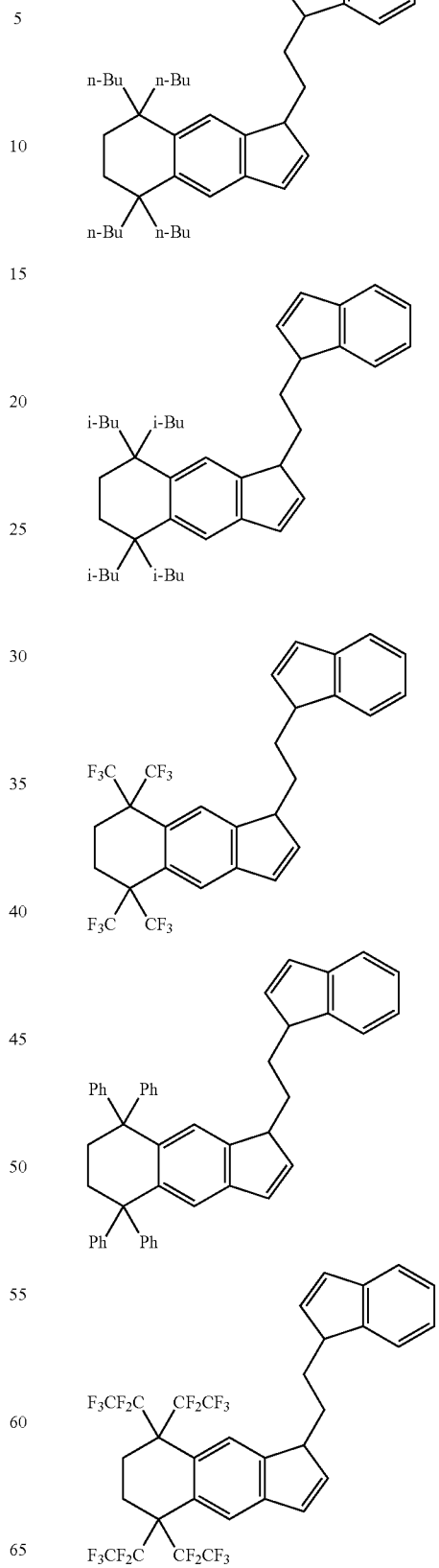

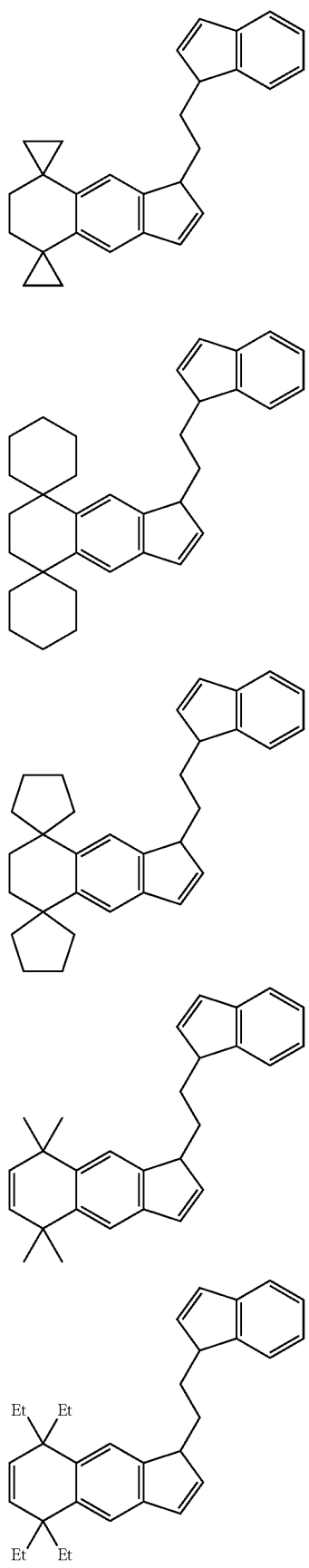
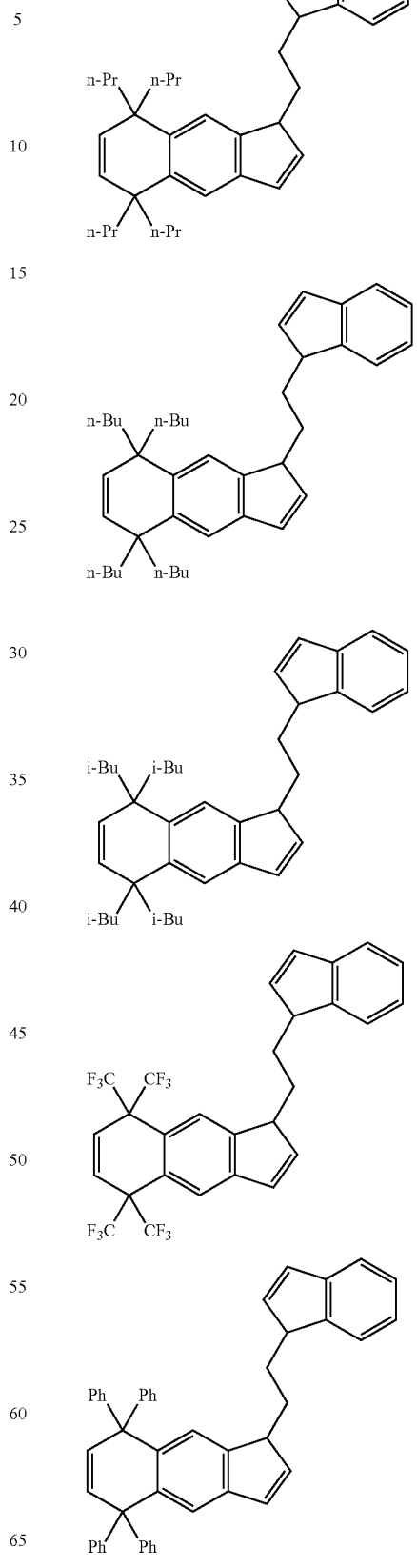

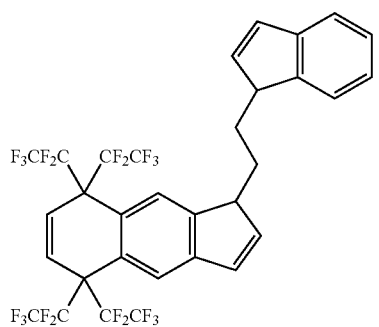
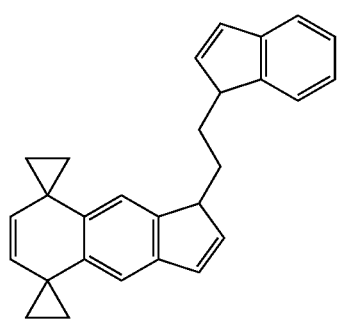
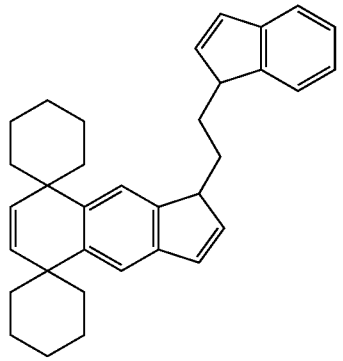
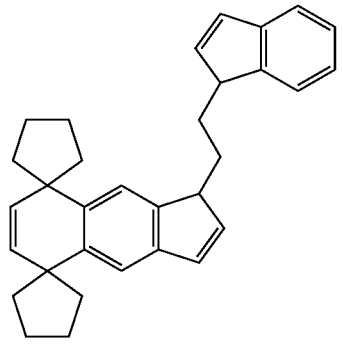
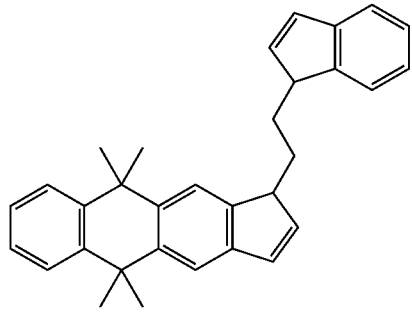
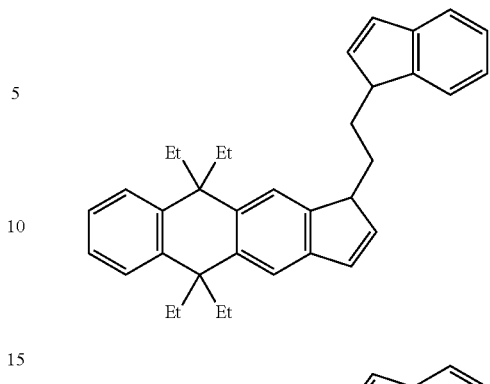
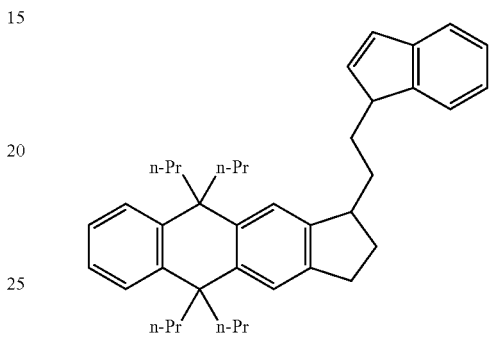
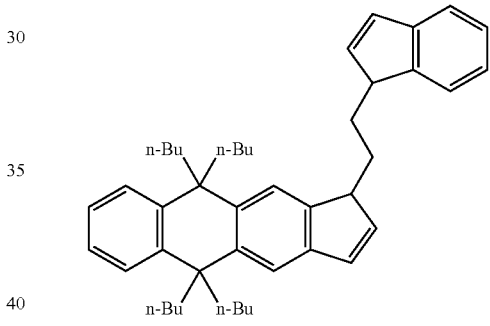
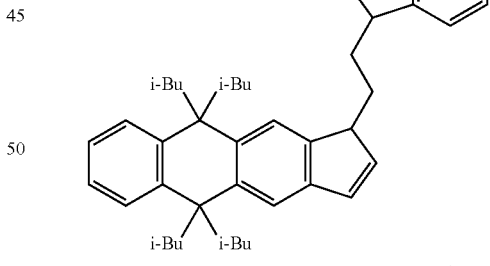
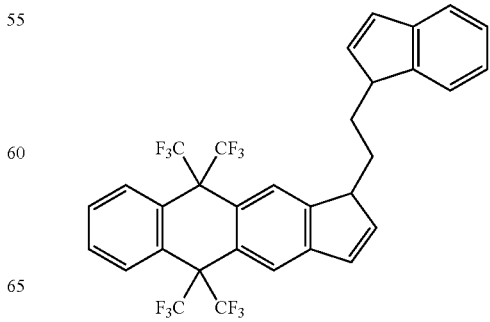

-continued

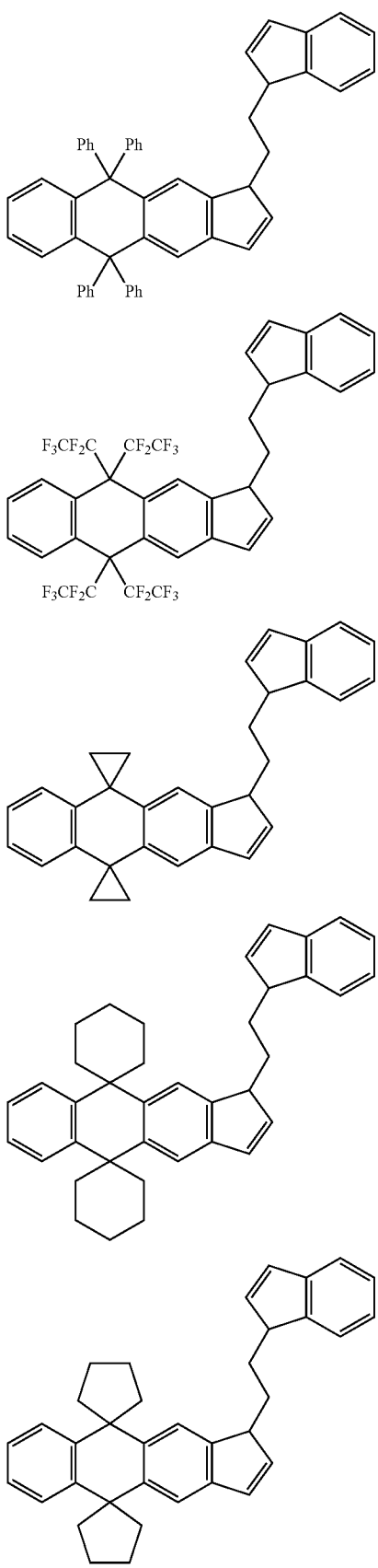

Among the compounds represented by the formulas (2-1) and (2-2), the compound represented by the formula (2-2) is preferable.

The compound represented by the formula (1-1) can be produced by the following steps using the compounds represented by the following formulas (3) and (4) as starting raw materials.

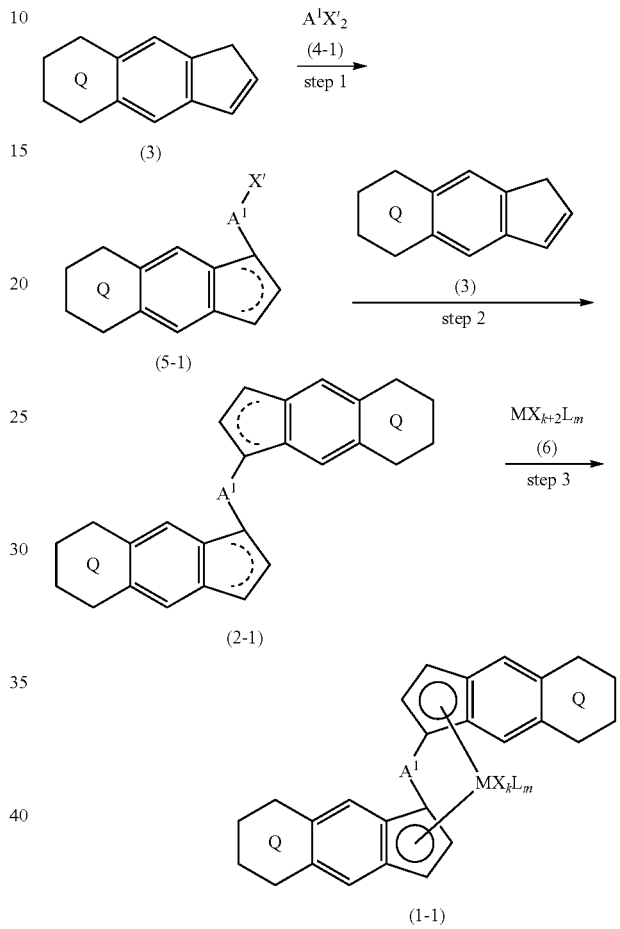

Step 1
In the formula (3),

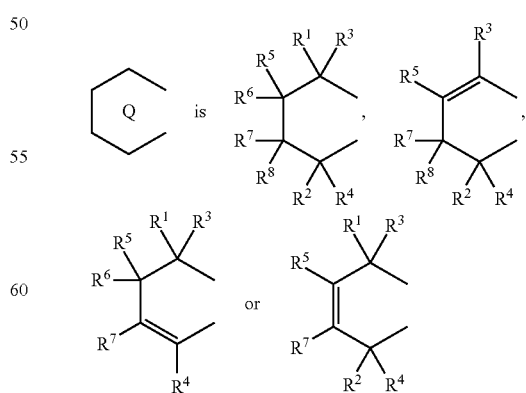

and all symbols in these formulas have the same meanings as those of symbols in the formula (1-1).

$A^1$ in the formula (4-1) has the same meaning as that described above; X' represents a halogen atom, anionic leaving groups such as an acetate group, a trifluoroacetate group, a benzoate group, a $CF_3SO_3$ group, a $CH_3SO_3$ group, a 4-$MeC_6H_4SO_3$ group and a $PhSO_3$ group, and two X's are the same as, or different from each other.

One part by mol of the compound represented by the formula (3) is reacted with preferably 1.00 to 5.00 parts by mol, more preferably 1.00 to 2.00 parts by mol, particularly preferably 1.00 to 1.20 parts by mol of a base such as n-butyllithium, sec-butyllithium, tert-butyllithium, lithium diisopropylamine, lithium hexamethyldisilazane, potassium hexamethyldisilazane, sodium hydride or potassium hydride at −100° C. to 100° C., preferably −80° C. to 50° C. for 5 minutes to 24 hours, although this is not shown in the above formula. Then, usually 1.0 to 10.0 equivalents, from the viewpoint of yield, preferably 1.0 to 6.0 equivalents, particularly preferably 1.0 to 4.0 equivalents of the compound represented by the formula (4-1) is reacted per 1 mol of the compound represented by the formula (3) at −100° C. to 150° C., preferably −80° C. to 50° C. for 5 minutes to 48 hours to produce a compound represented by the formula (5-1).

A solvent used in the step 1 is not particularly limited as far as it is a solvent which is generally used in a similar reaction. Examples of the solvent may include a hydrocarbyl solvent and an ether series. Among them, preferable is toluene, benzene, o-xylene, m-xylene, p-xylene, hexane, pentane, heptane, cyclohexane, diethyl ether or tetrahydrofuran, and more preferable is toluene, hexane, pentane, heptane, cyclohexane, diethyl ether or tetrahydrofuran.

The solvent is used such an amount that the concentration of the compound represented by the formula (3) is preferably 0.001 to 4.0 mol/L, more preferably 0.01 to 2.0 mol/L, further preferably 0.1 to 0.5 mol/L.

The present reaction is performed under a stream of air, helium, argon or nitrogen, preferably under a stream of helium, argon or nitrogen, and more preferably under a stream of nitrogen or argon. Since the influence of pressure can be neglected in the reaction of the step 1, it is general that the reaction is performed under atmospheric pressure.

After completion of the reaction, the compound represented by the formula (5-1) can be purified. Examples of the purification method may include a method of adding an ammonium chloride aqueous solution, a hydrogen chloride aqueous solution or a sodium chloride aqueous solution to the reaction solution, then, adding ethyl acetate or diethyl ether, and performing extraction operation to remove an excessive base or salt. The purity of the compound represented by the formula (5-1) can be increased by operations such as distillation, recrystallization and silica gel chromatography.

Step 2

The compound represented by the formula (3) is reacted with a base in the same manner as in the step 1, although this is not shown in the above formula. Then, a reaction with the compound represented by the formula (5-1) at −100° C. to 150° C., preferably −80° C. to 50° C. for 5 minutes to 48 hours produces the compound represented by the formula (2-1). The amount of the compound represented by the formula (3) to be used is usually 1.0 to 5.0 equivalents, from the viewpoint of yield, preferably 1.0 to 2.0 equivalents, particularly preferably 1.0 to 1.5 equivalents, per 1 mol of the compound represented by the formula (5-1).

A solvent used in the step 2 is the same as the solvent used in the step 1 and the amount thereof to be used is such an amount that the concentration of the compound represented by the formula (5-1) is 0.001 to 4.0 mol/L, more preferably 0.01 to 2.0 mol/L, and further preferably 0.1 to 0.8 mol/L. The reaction of the step 2 is performed under the same atmosphere and pressure as those of the step 1.

Purification and improvement in purity of the compound represented by the formula (2) can be performed by the same method as that of the step 1.

The compound represented by the formula (2-1) can also be produced by a process corresponding to an aspect in which the step 1 and the step 2 are simultaneously performed, comprising a step of reacting the base and 2.00 to 4.00 parts by mol of the compound represented by the formula (3) at −100° C. to 100° C., preferably −80° C. to 50° C. for 5 minutes to 24 hours and then, a step of further reacting with 1 part by mol of the compound represented by the formula (4-1) at −100° C. to 150° C., preferably −80° C. to 50° C. for 5 minutes to 48 hours.

Step 3

The transition metal compound represented by the formula (1-1) can be produced with reference to documents such as JP-A-2003-231693, Japanese Patent 3290218, and JP-A-2003-12682.

For example, when X is a fluorine atom, a chlorine atom, a bromine atom, an iodine atom, an alkoxy group having 1 to 20 carbon atoms and optionally having a halogen atom as a substituent, an aralkyloxy group having 7 to 20 carbon atoms and optionally having a halogen atom as a substituent, an aryloxy group having 6 to 20 carbon atoms and optionally having a halogen atom as a substituent, a silyl group optionally having, as a substituent, a hydrocarbyl group or halogenated hydrocarbyl group having 1 to 20 carbon atoms, a thiolate group optionally having, as a substituent, a hydrocarbyl group or a halogenated hydrocarbyl group having 1 to 20 carbon atoms, an amino group optionally having, as a substituent, a hydrocarbyl group or a halogenated hydrocarbyl group having 1 to 20 carbon atoms, or a carboxylate group optionally having, as a substituent, a hydrocarbyl group or a halogenated hydrocarbyl group having 1 to 20 carbon atoms, the compound represented by the formula (2-1) can be reacted with a base such as n-butyllithium, sec-butyllithium, tert-butyllithium, lithium diisopropylamine, lithium hexamethyldisilazane, potassium hexamethyldisilazane, sodium hydride or potassium hydride, preferably a base such as n-butyllithium, sec-butyllithium, or tert-butyllithium In the step 3, the temperature at which the compound represented by the formula (2-1) and the base are reacted is in a temperature range of −100° C. to 100° C., preferably −80° C. to 50° C., and the reaction time is 5 minutes to 24 hours, preferably 10 minutes to 12 hours, more preferably 30 minutes to 3 hours. The temperature at which the reaction product of the reaction and a compound represented by the formula (6) are reacted is −100° C. to 150° C., preferably −80° C. to 50° C., and the reaction time is 5 minutes to 48 hours, preferably 10 minutes to 24 hours.

A solvent used in the step 3 is not particularly limited as far as it is a solvent which is generally used in a similar reaction. Examples of the solvent may include a hydrocarbyl solvent and an ether series. Among them, preferable is toluene, benzene, o-xylene, m-xylene, p-xylene, hexane, pentane, heptane, cyclohexane, diethyl ether or tetrahydrofuran, more preferable is diethyl ether, toluene, tetrahydrofuran, hexane, pentane, heptane, or cyclohexane.

The reaction of the step 3 is performed under a stream of air, helium, argon or nitrogen, preferably under a stream of helium, argon or nitrogen, more preferably under a stream of nitrogen or argon. Since in the reaction, the influence of pressure can be neglected, the reaction is generally performed under atmospheric pressure.

The reaction temperature at which the compound represented by the formula (2-1) and the compound represented by the formula (6) are reacted in the step (3) is −100° C. to 150° C., preferably −80° C. to 50° C., and the reaction time is 5 minutes to 48 hours, preferably 10 minutes to 24 hours. The solvent in the present reaction is the same as that of the step 1. The reaction is performed under a stream of air, helium, argon or nitrogen, preferably helium, argon or nitrogen, more preferably nitrogen or argon.

The step 3 may be performed in the presence of an ionic compound, and examples of the ionic compound may include an ammonium fluoride, an ammonium chloride, an ammonium bromide, and an ammonium iodide. Among them, preferable is an ammonium chloride such as tetra-n-butylammonium chloride, tetra-n-propylammonium chloride, dimethyldistearylammonium chloride, dodecyltrimethylammonium chloride, hexadecyltrimethylammonium chloride, trimethylstearylammonium chloride, or trimethyltetradecylammonium chloride, and more preferable is tetra-n-butylammonium chloride.

The ionic additive is used usually at 0.001 to 1.0 equivalent, from the viewpoint of yield, preferably 0.01 to 0.5 equivalents, particularly preferably 0.05 to 0.2 equivalents per 1 mol of the compound represented by the formula (2-1).

The reaction of the step 3 is generally performed under atmospheric pressure.

After completion of the reaction, the compound represented by the formula (1-1) can be purified. Examples of the purification method may include a method of recrystallizing the compound, and a method of washing a solid obtained by concentrating the reaction solution with a suitable washing solvent. Examples of the washing solvent may include a hydrocarbyl solvent and an ether solvent. Among them, preferable is toluene, benzene, o-xylene, m-xylene, p-xylene, hexane, pentane, heptane, cyclohexane, diethyl ether or tetrahydrofuran, and more preferable is diethyl ether, toluene, tetrahydrofuran, hexane, pentane, heptane, or cyclohexane.

The compound represented by the formula (1-2) can be produced under the same conditions as those of the aforementioned production process, by changing the compound represented by the formula (3) in the production step 2 with a compound represented by the following formula (7), the compound represented by the formula (4-1) with a compound represented by the following formula (4-2), the compound represented by the formula (5-1) with a compound represented by the following formula (5-2), and the compound represented by the formula (2-1) with the compound represented by the formula (2-2), respectively.

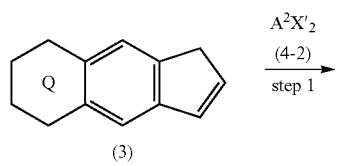

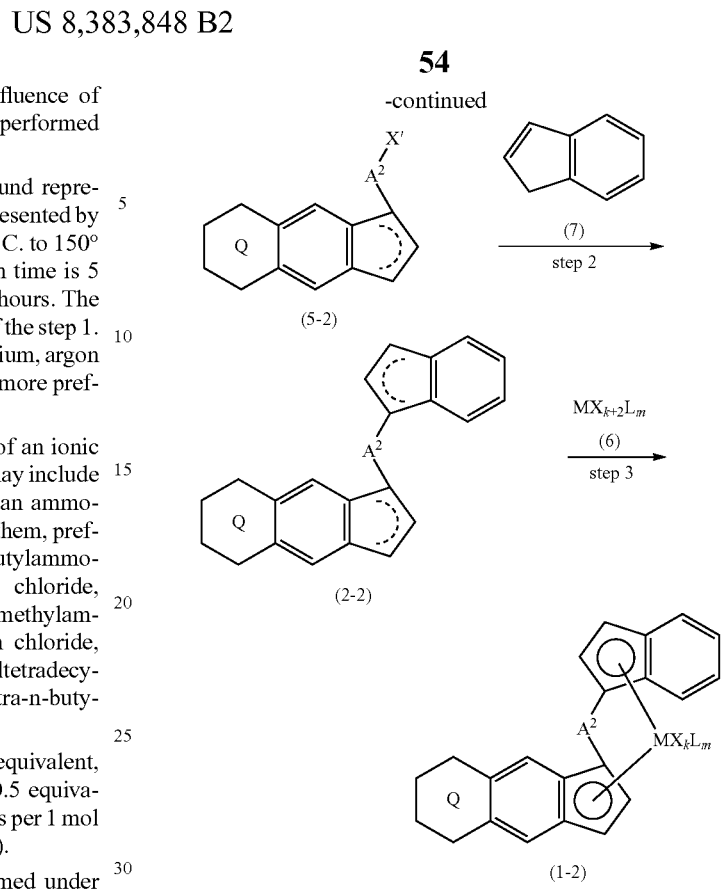

A co-catalytic component for activation used in the process for producing an olefin polymerization catalyst of the present invention is not particularly limited as far as it is a compound which activates the transition metal compound represented by the formula (1) as a polymerization catalyst component. Examples of the co-catalytic component for activation may include an organoaluminum compound (hereinafter, referred to as "organoaluminum compound A-1"), a boron compound and a combination thereof.

The organoaluminum compound A-1 may be a known compound, preferably compounds represented by the following formula, or a mixture thereof (1) a compound represented by the formula, $E^1{}_a AlY^1{}_{3-a}$;

(2) a cyclic alumoxane represented by the formula, $\{-Al(E^2)-O-\}_b$; and (3) a linear alumoxane represented by the formula, $E^3\{-Al(E^3)-O-\}_c AlE^3{}_2$;

wherein $E^1$, $E^2$ and $E^3$ are a hydrocarbyl group having 1 to 8 carbon atoms, all $E^1$s, all $E^2$s and all $E^3$s are the same as, or different from one another, $Y^1$ represents a hydrogen atom or a halogen atom, all $Y^1$s are the same as, or different from each other, a is a number satisfying $0<a\leq 3$, b is an integer of 2 or more, and c is an integer of 1 or more.

Examples of the organoaluminum compound A-1 represented by the formula $E^1{}_a AlY^1{}_{3-a}$ may include trialkylaluminums such as trimethylaluminum, triethylaluminum, tripropylaluminum, triisobutylaluminum, and trihexylaluminum; dialkylaluminum chlorides such as dimethylaluminum chloride, diethylaluminum chloride, dipropylaluminum chloride, diisobutylaluminum chloride, and dihexylaluminum chloride; alkylaluminum dichlorides such as methylaluminum dichloride, ethylaluminum dichloride, propylaluminum dichloride, isobutylaluminum dichloride, and hexylaluminum dichloride; as well as dialkylaluminum hydrides such as dimethylaluminum hydride, diethylaluminum hydride, dipropylaluminum hydride, diisobutylaluminum hydride, and dihexylaluminum hydride. Among them, preferable is a trialkylaluminum, and more preferable is triethylaluminum or triisob utylaluminum.

Examples of $E^2$ and $E^3$ in the above formula may include alkyl groups such as a methyl group, an ethyl group, a n-propyl group, an isopropyl group, a n-butyl group, an isobutyl group, a n-pentyl group, and a neopentyl group. Among them, preferable is a methyl group or an isobutyl group. Further, b is an integer of 2 or more, preferably an integer of 2 to 40, and c is an integer of 1 or more, preferably an integer of 1 to 40.

A process for producing the alumoxane is not particularly limited, and may be a known method. Examples of the production method may include a method of bringing a solution in which trialkylaluminum (e.g. trimethylaluminum) is dissolved in a suitable organic solvent (e.g. benzene or aliphatic hydrocarbyl) into contact with water, and a method of bringing trialkylaluminum (e.g. trimethylaluminum) into contact with a metal salt comprising crystal water (e.g. copper sulfate hydrate).

Examples of the boron compound may include the following compounds:

(1) a boron compound represented by the formula, $BR^{13}R^{14}R^{15}$;

(2) a boron compound represented by the formula, $M^{1+}(BR^{13}R^{14}R^{15}R^{16})^-$; and (3) a boron compound represented by the formula, $(M^{2-}H)^+(BR^{13}R^{14}R^{15}R^{16})^-$;

wherein $R^{13}$ to $R^{16}$ are a halogen atom, a hydrocarbyl group having 1 to 20 carbon atoms, a halogenated hydrocarbyl group having 1 to 20 carbon atoms, a substituted silyl group having 1 to 20 carbon atoms, an alkoxy group having 1 to 20 carbon atoms or a disubstituted amino group having 2 to 20 carbon atoms, they may be the same as, or different from one another, preferably a halogen atom, a hydrocarbyl group having 1 to 20 carbon atoms, or a halogenated hydrocarbyl group having 1 to 20 carbon atoms, $M^{1+}$ is an inorganic or organic cation, $M^2$ is a neutral Lewis base, and $(M^{2-}H)^+$ is a Broensted acid.

Examples of the compound represented by the formula (1) may include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, and phenylbis(pentafluorophenyl)borane. Among them, most preferable is tris(pentafluorophenyl)borane.

Examples of $M^{1+}$ in the formula (2) may include a ferrocenium cation, an alkyl-substituted ferrocenium cation, a silver cation and a triphenylmethyl cation. Examples of $(BR^{13}R^{14}R^{15}R^{16})^-$ in the formula (2) may include tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,2,4-trifluorophenyl)borate, phenylbis(pentafluorophenyl)borate, and tetrakis(3,5-bistrifluoromethylphenyl)borate. Examples of the compound of the formula (2) may include ferrocenium tetrakis(pentafluorophenyl)borate, 1,1'-dimethylferrocenium tetrakis(pentafluorophenyl)borate, silver tetrakis(pentafluorophenyl)borate, triphenylmethyltetrakis(pentafluorophenyl)borate, triphenylmethyltetrakis(3,5-bistrifluoromethylphenyl)borate. Among them, most preferable is triphenylmethyltetrakis(pentafluorophenyl)borate.

Examples of $(M^{2-}H)^+$ in the formula (3) may include trialkyl-substituted ammonium, N,N-dialkylanilinium, dialkylammonium, and triarylphosphonium. Examples of $(BR^{13}R^{14}R^{15}R^{16})^-$ may include the same as those mentioned above. Examples of the compound of the formula (3) may include triethylammonium tetrakis(pentafluorophenyl)borate, tripropylammonium tetrakis(pentafluorophenyl)borate, tri(n-butyl)ammonium tetrakis(pentafluorophenyl)borate, tri(n-butyl)ammonium tetrakis(3,5-bistrifluoromethylphenyl) borate, N,N-dimethylanilinium tetrakis(pentafluorophenyl) borate, N,N-diethylanilinium tetrakis(pentafluorophenyl) borate, N,N-2,4,6-pentamethylanilinium tetrakis (pentafluorophenyl)borate, N,N-dimethylanilinium tetrakis (3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri (methylphenyl)phosphonium tetrakis(pentafluorophenyl)borate, and tri(dimethylphenyl)phosphonium tetrakis(pentafluorophenyl)borate. Among them, most preferable is tri(n-butyl)ammonium tetrakis(pentafluorophenyl)borate, or N,N-dimethylanilinium tetrakis(pentafluorophenyl)borate.

The co-catalytic component for activation is preferably the cyclic alumoxane and/or the linear alumoxane, or a combination of the organic aluminum compound A-1 represented by $E^1aA^1Y1_{3-a}$ and a boron compound.

When a catalyst for polymerization according to the present invention is applied to polymerization accompanied with formation of a polymer particle such as slurry polymerization, vapor phase polymerization and bulk polymerization, a modified particle of the following (I) or (II) as the co-catalytic component for activation is suitably used.

(I) Modified particle obtained by bringing compound (a) represented by the following formula [1], compound (b) represented by the following formula [2], compound (c) represented by the following formula [3], and a particle (d) into contact with each other $$M^3L^1_d \qquad [1]$$

$$R^{17}_{t-1}TH \qquad [2]$$

$$R^{18}_{t-2}TH_2 \qquad [3]$$

wherein $M^3$ represents a typical metal atom of the Group 1, 2, 12, 14 or 15 of the periodic table, d represents a valence of $M^3$, $L^1$ represents a hydrogen atom, a halogen atom or a hydrocarbyl group, and when plural $L^1$s exist, they are the same as, or different from each other, $R^{17}$ represents an electron-withdrawing group or a group containing an electron-withdrawing group, and when plural $R^{17}$s exist, they are the same as, or different from each other, $R^{18}$ represents a hydrocarbyl group or a halogenated hydrocarbyl group, T in each compound independently represents of each other an atom of the Group 15 or 16 of the periodic table, and t represents a valence of T in each compound;

(II) Modified particle obtained by bringing alumoxane (e) into contact with a particle (d)

$M^3$ in the formula [1] represents a typical metal atom of the Group 1, 2, 12, 14 or 15 of the periodic table of elements (Revised edition of IUPAC Inorganic Chemistry Nomenclature 1989). Examples of $M^3$ may include a lithium atom, a sodium atom, a potassium atom, a rubidium atom, a cesium atom, a beryllium atom, a magnesium atom, a calcium atom, a strontium atom, a barium atom, a zinc atom, a cadmium atom, a mercury atom, a germanium atom, a tin atom, a lead atom, an antimony atom, and a bismuth atom. Among them, particularly preferable is an atom of the Group 12, most preferable is a zinc atom.

d in the formula [1] represents a valence of $M^3$ and, when $M^3$ is for example a zinc atom, d is 2.

$L^1$ in the formula [1] represents a hydrogen atom, a halogen atom or a hydrocarbyl group, and when plural $L^1$s exist, they are the same as, or different from each other.

Examples of the halogen atom may include a fluorine atom, a chlorine atom, a bromine atom and an iodide atom. As the hydrocarbyl group, an alkyl group, an aryl group or an aralkyl group is preferable.

The alkyl group is preferably an alkyl group having 1 to 20 carbon atoms. Examples of the alkyl group may include a methyl group, an ethyl group, a n-propyl group, an isopropyl group, a n-butyl group, a sec-butyl group, a tert-butyl group, an isobutyl group, a n-pentyl group, a neopentyl group, a n-hexyl group, a n-octyl group, a n-decyl group, a n-dodecyl group, a n-pentadecyl group, and a n-eicosyl group. Among them, preferable is a methyl group, an ethyl group, an isopropyl group, a tert-butyl group or an isobutyl group.

These alkyl groups may be substituted with a halogen atom such as a fluorine atom, a chlorine atom, a bromine atom or an iodine atom. Examples of the alkyl group having 1 to 20 carbon atoms and substituted with a halogen atom may include a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a diiodomethyl group, a triiodomethyl group, a fluoroethyl group, a difluoroethyl group, a trifluoroethyl group, a tetrafluoroethyl group, a pentafluoroethyl group, a chloroethyl group, a dichloroethyl group, a trichloroethyl group, a tetrachloroethyl group, a pentachloroethyl group, a bromoethyl group, a dibromoethyl group, a tribromoethyl group, a tetrabromoethyl group, a pentabromoethyl group, a perfluoropropyl group, a perfluorobutyl group, a perfluoropentyl group, a perfluorohexyl group, a perfluorooctyl group, a perfluorododecyl group, a perfluoropentadecyl group, a perfluoroeicosyl group, a perchloropropyl group, a perchlorobutyl group, a perchloropentyl group, a perchlorohexyl group, a perchlorooctyl group, a perchlorododecyl group, a perchloropentadecyl group, a perchloroeicosyl group, a perbromopropyl group, a perbromobutyl group, a perbromopentyl group, a perbromohexyl group, a perbromooctyl group, a perbromododecyl group, a perbromopentadecyl group, and a perbromoeicosyl group.

Further, these alkyl groups may be partially substituted with an alkoxy group such as a methoxy group or an ethoxy group, an aryloxy group such as a phenoxy group, or an aralkyloxy group such as a benzyloxy group.

As the aryl group, an aryl group having 6 to 20 carbon atoms is preferable. Examples of the aryl group may include a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group, and an anthracenyl group. These aryl groups may be partially substituted with a halogen atom such as a fluorine atom, a chlorine atom, a bromine atom or an iodine atom, an alkoxy group such as a methoxy group or an ethoxy group, an aryloxy group such as a phenoxy group, or an aralkyloxy group such as a benzyloxy group.

As the aralkyl group, an aralkyl group having 7 to 20 carbon atoms is preferable. Examples of the aralkyl group may include a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (3,5-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl)methyl group, a (tert-butylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, a (n-tetradecylphenyl)methyl group, a naphthylmethyl group, and an anthracetylmethyl group. Among them, preferable is a benzyl group. These aralkyl groups may be partially substituted with a halogen atom such as a fluorine atom, a chlorine atom, a bromine atom or an iodine atom, an alkoxy group such as a methoxy group or an ethoxy group, an aryloxy group such as a phenoxy group, or an aralkyloxy group such as a benzyloxy group.

The $L^1$ is preferably a hydrogen atom, an alkyl group or an aryl group, further preferably a hydrogen atom or an alkyl group, particularly preferably an alkyl group.

Each T in the formulas [2] and [3] independently represents of each other an atom of the Group 15 or 16 of the periodic table of elements (Revised edition of IUPAC Inorganic Chemistry Nomenclature 1989). T in the formula [2] and T in the formula [3] are the same as, or different from each other. Examples of the atom of the Group 15 may include a nitrogen atom and a phosphorus atom, and examples of the atom of the Group 16 may include an oxygen atom and a sulfur atom. Among them, T in each formula is preferably independently of each other a nitrogen atom or an oxygen atom, particularly preferably, T is an oxygen atom. Each t in the formulas [2] and [3] represents a valence of each T and, when T is an atom of the Group 15, t is 3, and when T is an atom of the Group 16, t is 2.

$R^{15}$ in the formula [2] represents an electron-withdrawing group or a group containing an electron-withdrawing group, and when plural $R^1$s exist, they are the same as, or different from each other. As an index of the electron-withdrawing property, there is known a substituent constant σ of the Hammet's rule and the like, and a functional group having positive σ is an electron-withdrawing group in the present invention.

Examples of the electron-withdrawing group may include a fluorine atom, a chlorine atom, a bromine atom, an iodine group, a cyano group, a nitro group, a carbonyl group, a sulfone group and a phenyl group. Examples of the group containing an electron-withdrawing group may include a halogenated alkyl group, a halogenated aryl group, a (halogenated alkyl)aryl group, a cyanated aryl group, a nitrated aryl group, and an ester group (e.g. alkoxycarbonyl group, aralkyloxycarbonyl group and aryloxycarbonyl group).

Examples of the halogenated alkyl group may include a fluoromethyl group, a chloromethyl group, a bromomethyl group, an iodomethyl group, a difluoromethyl group, a dichloromethyl group, a dibromomethyl group, a diiodomethyl group, a trifluoromethyl group, a trichloromethyl group, a tribromomethyl group, a triiodomethyl group, a 2,2,2-trifluoroethyl group, a 2,2,2-trichloroethyl group, a 2,2,2-tribromoethyl group, a 2,2,2-triiodoethyl group, a 2,2,3,3,3-pentafluoropropyl group, a 2,2,3,3,3-pentachloropropyl group, a 2,2,3,3,3-pentabromopropyl group, a 2,2,3,3,3-pentaiodopropyl group, a 2,2,2-trifluoro-1-trifluoromethylethyl group, a 2,2,2-trichloro-1-trichloromethylethyl group, a 2,2,2-tribromo-1-tribromomethylethyl group, a 2,2,2-triiodo-1-triiodomethylethyl group, a 1,1-bis(trifluoromethyl)-2,2,2-trifluoroethyl group, a 1,1-bis(trichloromethyl)-2,2,2-trichloroethyl group, a 1,1-bis(tribromomethyl)-2,2,2-tribromoethyl group, and a 1,1-bis(triiodomethyl)-2,2,2-triiodoethyl group.

Examples of the halogenated aryl group may include a 2-fluorophenyl group, a 3-fluorophenyl group, a 4-fluorophenyl group, a 2,4-difluorophenyl group, a 2,6-difluorophenyl group, a 3,4-difluorophenyl group, a 3,5-difluorophenyl group, a 2,4,6-trifluorophenyl group, a 3,4,5-trifluorophenyl group, a 2,3,5,6-tetrafluorophenyl group, a pentafluorophenyl group, a 2,3,5,6-tetrafluoro-4-trifluoromethylphenyl group, a 2,3,5,6-tetrafluoro-4-pentafluorophenylphenyl group, a perfluoro-1-naphtyl group, a perfluoro-2-naphthyl group, a 2-chlorophenyl group, a 3-chlorophenyl group, a 4-chlorophenyl group, a 2,4-dichlorophenyl group, a 2,6-dichlorophenyl group, a 3,4-dichlorophenyl group, a 3,5-dichlorophenyl group, a 2,4,6-trichlorophenyl group, a 3,4,5-trichlorophenyl group, a 2,3,5,6-tetrachlorophenyl group, a pentachlorophenyl group, a 2,3,5,6-tetrachloro-4-trichloromethylphenyl group, a 2,3,5,6-tetrachloro-4-pentachlorophenylphenyl group, a perchloro-1-naphthyl group, a perchloro-2-naphthyl group, a 2-bromophenyl group, a 3-bromophenyl group, a 4-bromophenyl group, a 2,4-dibromophenyl group, a 2,6-dibromophenyl group, a 3,4-dibromophenyl group, a 3,5-dibromophenyl group, a 2,4,6-tribromophenyl group, a 3,4,5-tribromophenyl group, a 2,3,5,6-tetrabromophenyl group, a pentabromophenyl group, a 2,3,5,6-tetrabromo-4-tribromomethylphenyl group, a 2,3,5,6-tetrabromo-4-pentabromophenylphenyl group, a perbromo-1-naphtyl group, a perbromo-2-naphthyl group, a 2-iodophenyl group, a 3-iodophenyl group, a 4-iodophenyl group, a 2,4-diiodophenyl group, a 2,6-diiodophenyl group, a 3,4-diiodophenyl group, a 3,5-diiodophenyl group, a 2,4,6-triiodophenyl group, a 3,4,5-triiodophenyl group, a 2,3,5,6-tetraiodophenyl group, a pentaiodophenyl group, a 2,3,5,6-tetraiodo-4-triiodomethylphenyl group, a 2,3,5,6-tetraiodo-4-pentaiodophenylphenyl group, a periodo-1-naphthyl group, and a periodo-2-naphthyl group.

Examples of the (halogenated alkyl)aryl group may include a 2-(trifluoromethyl)phenyl group, a 3-(trifluoromethyl)phenyl group, a 4-(trifluoromethyl)phenyl group, a 2,6-bis(trifluoromethyl)phenyl group, a 3,5-bis(trifluoromethyl)phenyl group, a 2,4,6-tris(trifluoromethyl)phenyl group, and a 3,4,5-tris(trifluoromethyl)phenyl group.

Examples of the cyanated aryl group may include a 2-cyanophenyl group, a 3-cyanophenyl group, and a 4-cyanophenyl group.

Examples of the nitrated aryl group may include a 2-nitrophenyl group, a 3-nitrophenyl group, and a 4-nitrophenyl group.

Examples of the ester group may include a methoxycarbonyl group, an ethoxycarbonyl group, a n-propoxycarbonyl group, an isopropoxycarbonyl group, a phenoxycarbonyl group, a trifluoromethoxycarbonyl group, and a pentafluorophenoxycarbonyl group.

The $R^{15}$ is preferably a halogenated hydrocarbyl group, more preferably a halogenated alkyl group or a halogenated aryl group, further preferably a fluoromethyl group, a difluoromethyl group, a trifluoromethyl group, a 2,2,2-trifluoroethyl group, a 2,2,3,3,3-pentafluoropropyl group, a 2,2,2-trifluoro-1-trifluoromethylethyl group, a 1,1-bis(trifluoromethyl)-2,2,2-trifluoroethyl group, a 2-fluorophenyl group, a 3-fluorophenyl group, a 4-fluorophenyl group, a 2,4-difluorophenyl group, a 2,6-difluorophenyl group, a 3,4-difluorophenyl group, a 3,5-difluorophenyl group, a 2,4,6-trifluorophenyl group, a 3,4,5-trifluorophenyl group, a 2,3,5,6-tetrafluorophenyl group, a pentafluorophenyl group, a 2,3,5,6-tetrafluoro-4-trifluoromethylphenyl group, a 2,3,5,6-tetrafluoro-4-pentafluorophenylphenyl group, a perfluoro-1-naphthyl group, a perfluoro-2-naphthyl group, a chloromethyl group, a dichloromethyl group, a trichloromethyl group, a 2,2,2-trichloroethyl group, a 2,2,3,3,3-pentachloropropyl group, a 2,2,2-trichloro-1-trichloromethylethyl group, a 1,1-bis(trichloromethyl)-2,2,2-trichloroethyl group, a 4-chlorophenyl group, a 2,6-dichlorophenyl group, a 3,5-dichlorophenyl group, a 2,4,6-trichlorophenyl group, a 3,4,5-trichlorophenyl group, or a pentachlorophenyl group, particularly preferably a fluoroalkyl group or a fluoroaryl group, most preferably a trifluoromethyl group, a 2,2,2-trifluoro-1-trifluoromethylethyl group, a 1,1-bis(trifluoromethyl)-2,2,2-trifluoroethyl group, a 3,5-difluorophenyl group, a 3,4,5-trifluorophenyl group or a pentafluorophenyl group.

$R^{18}$ as the hydrocarbyl group is preferably an alkyl group, an aryl group or an aralkyl group. Examples of $R^{18}$ may include the hydrocarbyl group exemplified as $L^1$. Examples of $R^{18}$, as halogenated hydrocarbyl groups, may include a halogenated alkyl group, a halogenated aryl group, and a (halogenated alkyl)aryl group. Examples of $R^{16}$ may include the halogenated alkyl group, the halogenated aryl group and the (halogenated alkyl)aryl group, exemplified as the electron-withdrawing group of $R^{17}$. $R^{18}$ is preferably a halogenated hydrocarbyl group, further preferably a fluorinated hydrocarbyl group.

Examples of the compound (a), when $M^3$ is a zinc atom, may include dialkylzincs such as dimethylzinc, diethylzinc, dipropylzinc, di-n-butylzinc, diisobutylzinc and di-n-hexylzinc; diarylzincs such as diphenylzinc, dinaphthylzinc, and bis(pentafluorophenyl)zinc; dialkenylzincs such as diallylzinc; bis(cyclopentadienyl)zinc; alkylzinc halides such as methylzinc chloride, ethylzinc chloride, propylzinc chloride, n-butylzinc chloride, isobutylzinc chloride, n-hexylzinc chloride, methylzinc bromide, ethylzinc bromide, propylzinc bromide, n-butylzinc bromide, isobutylzinc bromide, n-hexylzinc bromide, methylzinc iodide, ethylzinc iodide, propylzinc iodide, n-butylzinc iodide, isobutylzinc iodide, and n-hexylzinc iodide; as well as zinc halides such as zinc fluoride, zinc chloride, zinc bromide, and zinc iodide.

The compound (a) is preferably dialkylzinc, further preferably dimethylzinc, diethylzinc, dipropylzinc, di-n-butylzinc, diisobutylzinc, or di-n-hexylzinc, particularly preferably dimethylzinc or diethylzinc.

Examples of amines of the compound (b) may include di(fluoromethyl)amine, di(chloromethyl)amine, di(bromomethyl)amine, di(iodomethyl)amine, bis(difluoromethyl)amine, bis(dichloromethyl)amine, bis(dibromomethyl)amine, bis(diiodomethyl)amine, bis(trifluoromethyl)amine, bis(trichloromethyl)amine, bis(tribromomethyl)amine, bis(triiodomethyl)amine, bis(2,2,2-trifluoroethyl)amine, bis(2,2,2-trichloroethyl)amine, bis(2,2,2-tribromoethyl)amine, bis(2,2,2-triiodoethyl)amine, bis(2,2,3,3,3-pentafluoropropyl)amine, bis(2,2,3,3,3-pentachloropropyl)amine, bis(2,2,3,3,3-pentabromopropyl)amine, bis(2,2,3,3,3-pentaiodopropyl)amine, bis(2,2,2-trifluoro-1-trifluoromethylethyl)amine, bis(2,2,2-trichloro-1-trichloromethylethyl)amine, bis(2,2,2-tribromo-1-tribromomethylethyl)amine, bis(2,2,2-triiodo-1- triiodomethylethyl)amine, bis(1,1-bis(trifluoromethyl)-2,2,2-trifluoroethyl)amine, bis(1,1-bis(trichloromethyl)-2,2,2-trichloroethyl)amine, bis(1,1-bis(tribromomethyl)-2,2,2-tribromoethyl)amine, bis(1,1-bis(triiodomethyl)-2,2,2-triiodoethyl)amine, bis(2-fluorophenyl)amine, bis(3-fluorophenyl)amine, bis(4-fluorophenyl)amine, bis(2-chlorophenyl)amine, bis(3-chlorophenyl)amine, bis(4-chlorophenyl)amine, bis(2-bromophenyl)amine, bis(3-bromophenyl)amine, bis(4-bromophenyl)amine, bis(2-iodophenyl)amine, bis(3-iodophenyl)amine, bis(4-iodophenyl)amine, bis(2,6-difluorophenyl)amine, bis(3,5-difluorophenyl)amine, bis(2,6-dichlorophenyl)amine, bis(3,5-dichlorophenyl)amine, bis(2,6-dibromophenyl)amine, bis(3,5-dibromophenyl)amine, bis(2,6-diiodophenyl)amine, bis(3,5-diiodophenyl)amine, bis(2,4,6-trifluorophenyl)amine, bis(2,4,6-trichlorophenynamine, bis(2,4,6-tribromophenyl)amine, bis(2,4,6-triiodophenyl)amine, bis(3,4,5-trifluorophenyl)amine, bis(3,4,5-trichlorophenyl)amine, bis(3,4,5-tribromophenyl)amine, bis(3,4,5-triiodophenyl)amine, bis(pentafluorophenyl)amine, bis(pentachlorophenyl)amine, bis(pentabromophenyl)amine, bis(pentaiodophenyl)amine, bis(2-(trifluoromethyl)phenyl)amine, bis(3-(trifluoromethyl)phenyl)amine, bis(4-(trifluoromethyl)phenyl)amine, bis(2,6-di(trifluoromethyl)phenyl)amine, bis(3,5-di(trifluoromethyl)phenyl)amine, bis(2,4,6-tri(trifluoromethyl)phenyl)amine, bis(3,4,5-tri(trifluoromethyl)phenyl)amine, bis(2-cyanophenyl)amine, (3-cyanophenyl)amine, bis(4-cyanophenyl)amine, bis(2-nitrophenyl)amine, bis(3-nitrophenyl)amine, and bis(4-nitrophenyl)amine, as well as phosphine compounds having a phosphorus atom in place of the nitrogen atom. The phosphine compounds are those expressed by rewriting the above term amine with the term phosphine.

Examples of the compound (b), as alcohols, may include fluoromethanol, chloromethanol, bromomethanol, iodomethanol, difluoromethanol, dichloromethanol, dibromomethanol, diiodomethanol, trifluoromethanol, trichloromethanol, tribromomethanol, triiodomethanol, 2,2,2-trifluoroethanol, 2,2,2-trichloroethanol, 2,2,2-tribromoethanol, 2,2,2-triiodoethanol, 2,2,3,3,3-pentafluoropropanol, 2,2,3,3,3-pentachloropropanol, 2,2,3,3,3-pentabromopropanol, 2,2,3,3,3-pentaiodopropanol, 2,2,2-trifluoro-1-trifluoromethylethanol, 2,2,2-trichloro-1-trichloromethylethanol, 2,2,2-tribromo-1-tribromomethylethanol, 2,2,2-triiodo-1-triiodomethylethanol, 1,1-bis(trifluoromethyl)-2,2,2-trifluoroethanol, 1,1-bis(trichloromethyl)-2,2,2-trichloroethanol, 1,1-bigtribromomethyl)-2,2,2-tribromoethanol, and 1,1-bis(triiodomethyl)-2,2,2-triiodoethanol, and thiol compounds having a sulfur atom in place of the oxygen atom of these compounds. The thiol compounds are those expressed by rewriting the above terms methanol, ethanol and propanol with the terms methanethiol, ethanethiol and propanethiol, respectively.

Examples of the compound (b), as phenols, may include 2-fluorophenol, 3-fluorophenol, 4-fluorophenol, 2,4-difluorophenol, 2,6-difluorophenol, 3,4-difluorophenol, 3,5-difluorophenol, 2,4,6-trifluorophenol, 3,4,5-trifluorophenol, 2,3,5,6-tetrafluorophenol, pentafluorophenol, 2,3,5,6-tetrafluoro-4-trifluoromethylphenol, 2,3,5,6-tetrafluoro-4-pentafluorophenylphenol, perfluoro-1-naphthol, perfluoro-2-naphthol, 2-chlorophenol, 3-chlorophenol, 4-chlorophenol, 2,4-dichlorophenol, 2,6-dichlorophenol, 3,4-dichlorophenol, 3,5-dichlorophenol, 2,4,6-trichlorophenol, 3,4,5-trichlorophenol, 2,3,5,6-tetrachlorophenol, pentachlorophenol, 2,3,5,6-tetrachloro-4-trichloromethylphenol, 2,3,5,6-tetrachloro-4-pentachlorophenylphenol, perchloro-1-naphthol, perchloro-2-naphthol, 2-bromophenol, 3-bromophenol, 4-bromophenol, 2,4-dibromophenol, 2,6-dibromophenol, 3,4-dibromophenol, 3,5-dibromophenol, 2,4,6-tribromophenol, 3,4,5-tribromophenol, 2,3,5,6-tetrabromophenol, pentabromophenol, 2,3,5,6-tetrabromo-4-tribromomethylphenol, 2,3,5,6-tetrabromo-4-pentabromophenylphenol, perbromo-1-naphthol, perbromo-2-naphthol, 2-iodophenol, 3-iodophenol, 4-iodophenol, 2,4-diiodophenol, 2,6-diiodophenol, 3,4-diiodophenol, 3,5-diiodophenol, 2,4,6-triiodophenol, 3,4,5-triiodophenol, 2,3,5,6-tetraiodophenol, pentaiodophenol, 2,3,5,6-tetraiodo-4-triiodomethylphenol, 2,3,5,6-tetraiodo-4-pentaiodophenylphenol, periodo-1-naphthol, periodo-2-naphthol, 2-(trifluoromethyl)phenol, 3-(trifluoromethyl)phenol, 4-(trifluoromethyl)phenol, 2,6-bis(trifluoromethyl)phenol, 3,5-bis(trifluoromethyl)phenol, 2,4,6-tris(trifluoromethyl)phenol, 3,4,5-tris(trifluoromethyl)phenol, 2-cyanophenol, 3-cyanophenol, 4-cyanophenol, 2-nitrophenol, 3-nitrophenol, and 4-nitrophenol, and thiophenol compounds having a sulfur atom in place of the oxygen atom. The thiophenol compounds are those expressed by rewriting the term phenol of the above compounds with the term thiophenol.

The compound (b) is preferably, as amines, bis(trifluoromethyl)amine, bis(2,2,2-trifluoroethyl)amine, bis(2,2,3,3,3-pentafluoropropyl)amine, bis(2,2,2-trifluoro-1-trifluoromethylethyl)amine, bis(1,1-bis(trifluoromethyl)-2,2,2-trifluoroethyl)amine, or bis(pentafluorophenyl)amine, as alcohols, trifluoromethanol, 2,2,2-trifluoroethanol, 2,2,3,3,3-pentafluoropropanol, 2,2,2-trifluoro-1-trifluoromethylethanol, or 1,1-bis(trifluoromethyl)-2,2,2-trifluoroethanol, as phenols, 2-fluorophenol, 3-fluorophenol, 4-fluorophenol, 2,6-difluorophenol, 3,5-difluorophenol, 2,4,6-trifluorophenol, 3,4,5-trifluorophenol, pentafluorophenol, 2-(trifluoromethyl)phenol, 3-(trifluoromethyl)phenol, 4-(trifluoromethyl)phenol, 2,6-bis(trifluoromethyl)phenol, 3,5-bis(trifluoromethyl)phenol, 2,4,6-tris(trifluoromethyl)phenol, or 3,4,5-tris(trifluoromethyl)phenol.

The compound (b) is more preferably bis(trifluoromethyl)amine, bis(pentafluorophenyl)amine, trifluoromethanol, 2,2,2-trifluoro-1-trifluoromethylethanol, 1,1-bis(trifluoromethyl)-2,2,2-trifluoroethanol, 2-fluorophenol, 3-fluorophenol, 4-fluorophenol, 2,6-difluorophenol, 3,5-difluorophenol, 2,4,6-trifluorophenol, 3,4,5-trifluorophenol, pentafluorophenol, 4-(trifluoromethyl)phenol, 2,6-bis(trifluoromethyl)phenol, or 2,4,6-tris(trifluoromethyl)phenol, further preferably 3,5-difluorophenol, 3,4,5-trifluorophenol, pentafluorophenol, or 1,1-bis(trifluoromethyl)-2,2,2-trifluoroethanol.

The compound (c) is preferably water, hydrogen sulfide, alkylamine, arylamine, aralkylamine, halogenated alkylamine, halogenated arylamine, or (halogenated alkyl)arylamine, further preferably water, hydrogen sulfide, methylamine, ethylamine, n-propylamine, isopropylamine, n-butylamine, sec-butylamine, tert-butylamine, isobutylamine, n-pentylamine, neopentylamine, isopentylamine, n-hexylamine, n-octylamine, n-decylamine, n-dodecylamine, n-pentadecylamine, n-eicosylamine, allylamine, cyclopentadienylamine, aniline, 2-tolylamine, 3-tolylamine, 4-tolylamine, 2,3-xylylamine, 2,4-xylylamine, 2,5-xylylamine, 2,6-xylylamine, 3,4-xylylamine, 3,5-xylylamine, 2,3,4-trimethylaniline, 2,3,5-trimethylaniline, 2,3,6-trimethylaniline, 2,4,6-trimethylaniline, 3,4,5-trimethylaniline, 2,3,4,5-tetramethylaniline, 2,3,4,6-tetramethylaniline, 2,3,5,6-tetramethylaniline, pentamethylaniline, ethylaniline, n-propylaniline, isopropylaniline, n-butylaniline, sec-butylaniline, tert-butylaniline, n-pentylaniline, neopentylaniline, n-hexylaniline, n-octylaniline, n-decylanfline, n-dodecylaniline, n-tetradecylaniline, naphthylamine, anthracenylamine, benzylamine, (2-methylphenyl)methylamine, (3-methylphenyl)methylamine, (4-methylphenyl)methylamine, (2,3-dimethylphenyl)methylamine, (2,4-dimethylphenyl)methylamine, (2,5-dimethylphenyl)methylamine, (2,6-dimethylphenyl)methylamine, (3,4-dimethylphenyl)methylamine, (3,5-dimethylphenyl)methylamine, (2,3,4-trimethylphenyl)methylamine, (2,3,5-trimethylphenyl)methylamine, (2,3,6-trimethylphenyl)methylamine, (3,4,5-trimethylphenyl)methylamine, (2,4,6-trimethylphenyl)methylamine, (2,3,4,5-tetramethylphenyl)methylamine, (2,3,4,6-tetramethylphenyl)methylamine, (2,3,5,6-tetramethylphenyl)methylamine, (pentamethylphenyl)methylamine, (ethylphenyl)methylamine, (n-propylphenyl)methylamine, (isopropylphenyl)methylamine, (n-butylphenyl)methylamine, (sec-butylphenyl)methylamine, (tert-butylphenyl)methylamine, (n-pentylphenyl)methylamine, (neopentylphenyl)methylamine, (n-hexylphenyl)methylamine, (n-octylphenyl)methylamine, (n-decylphenyl)methylamine, (n-tetradecylphenyl)methylamine, naphthylmethylamine, anthracenylmethylamine, fluoromethylamine, chloromethylamine, bromomethylamine, iodomethylamine, difluoromethylamine, dichloromethylamine, dibromomethylamine, diiodomethylamine, trifluoromethylamine, trichloromethylamine, tribromomethylamine, triiodomethylamine, 2,2,2-trifluoroethylamine, 2,2,2-trichloroethylamine, 2,2,2-tribromoethylamine, 2,2,2-triiodoethylamine, 2,2,3,3,3-pentafluoropropylamine, 2,2,3,3,3-pentachloropropylamine, 2,2,3,3,3-pentabromopropylamine, 2,2,3,3,3-pentaiodopropylamine, 2,2,2-trifluoro-1-trifluoromethylethylamine, 2,2,2-trichloro-1-trichloromethylethylamine, 2,2,2-tribromo-1-tribromomethylethylamine, 2,2,2-triiodo-1-triiodomethylethylamine, 1,1-bis(trifluoromethyl)-2,2,2-trifluoroethylamine, 1,1-bis(trichloromethyl)-2,2,2-trichloroethylamine, 1,1-bis(tribromomethyl)-2,2,2-tribromoethylamine, 1,1-bis(triiodomethyl)-2,2,2-triiodoethylamine, 2-fluoroaniline, 3-fluoroaniline, 4-fluoroaniline, 2-chloroaniline, 3-chloroaniline, 4-chloroaniline, 2-bromoaniline, 3-bromoaniline, 4-bromoaniline, 2-iodoaniline, 3-iodoaniline, 4-iodoaniline, 2,6-difluoroaniline, 3,5-difluoroaniline, 2,6-dichloroaniline, 3,5-dichloroaniline, 2,6-dibromoaniline, 3,5-dibromoaniline, 2,6-diiodoaniline, 3,5-diiodoaniline, 2,4,6-trifluoroaniline, 2,4,6-trichloroaniline, 2,4,6-tribromoaniline, 2,4,6-triiodoaniline, 3,4,5-trifluoroaniline, 3,4,5-trichloroaniline, 3,4,5-tribromoaniline, 3,4,5-triiodoaniline, pentafluoroaniline, pentachloroaniline, pentabromoaniline, pentaiodoaniline, 2-(trifluoromethyl)aniline, 3-(trifluoromethyl)aniline, 4-(trifluoromethyl)aniline, 2,6-di(trifluoromethyl)aniline, 3,5-di(trifluoromethyl)aniline, 2,4,6-tri(trifluoromethyl)aniline, or 3,4,5-tri(trifluoromethyl)aniline.

The compound (c) is more preferably water, hydrogen sulfide, methylamine, ethylamine, n-propylamine, isopropylamine, n-butylamine, sec-butylamine, tert-butylamine, isobutylamine, n-octylamine, aniline, 2,6-xylylamine, 2,4,6-trimethylaniline, naphthylamine, anthracenylamine, benzylamine, trifluoromethylamine, pentafluoroethylamine, perfluoropropylamine, perfluorobutylamine, perfluoropentylamine, perfluorohexylamine, perfluorooctylamine, perfluorododecylamine, perfluoropentadecylamine, perfluoroeicosylamine, 2-fluoroaniline, 3-fluoroaniline, 4-fluoroaniline, 2,6-difluoroaniline, 3,5-difluoroaniline, 2,4,6-trifluoroaniline, 3,4,5-trifluoroaniline, pentafluoroaniline, 2-(trifluoromethyl)aniline, 3-(trifluoromethyl)aniline, 4-(trifluoromethyl)aniline, 2,6-bis(trifluoromethyl)aniline, 3,5-bis(trifluoromethyl)aniline, 2,4,6-tris(trifluoromethyl)aniline, or 3,4,5-tris(trifluoromethyl)aniline, particularly preferably water, trifluoromethylamine, perfluorobutylamine, perfluorooctylamine, perfluoropentadecylamine, 2-fluoroaniline, 3-fluoroaniline, 4-fluoroaniline, 2,6-difluoroaniline, 3,5-difluoroaniline, 2,4,6-trifluoroaniline, 3,4,5-trifluoroaniline, pentafluoroaniline, 2-(trifluoromethyl)aniline, 3-(trifluoromethyl)aniline, 4-(trifluoromethyl)aniline, 2,6-bis(trifluoromethyl)aniline, 3,5-bis(trifluoromethyl)aniline, 2,4,6-tris(trifluoromethyl)aniline, or 3,4,5-tris(trifluoromethyl)aniline, most preferably water or pentafluoroaniline.

As the particle (d), particles which are generally used as a carrier are preferable. Among them, a porous substance having a uniform particle diameter is preferable, an inorganic substance or an organic polymer is suitable, and an inorganic substance is more preferable.

The geometric standard deviation based on a volume of a particle diameter of the particle (d), from the viewpoint of particle diameter distribution of the obtained polymer, is preferably not more than 2.5, more preferably not more than 2.0, and further preferably not more than 1.7.

Examples of the inorganic substance may include inorganic oxides, magnesium compounds, clay, clay mineral and a combination thereof. Among them, inorganic oxides are suitable.

Examples of the inorganic oxide may include $SiO_2$, $Al_2O_3$, MgO, $ZrO_2$, $TiO_2$, $B_2O_3$, CaO, ZnO, BaO, $ThO_2$, and a mixture thereof (e.g. $SiO_2$—MgO, $SiO_2$—$Al_2O_3$, $SiO_2$—$TiO_2$, $SiO_2$—$V_2O_5$, $SiO_2$—$Cr_2O_3$, and $SiO_2$—$TiO_2$—MgO). Among them, $SiO_2$ and/or $Al_2O_3$ are/is preferable, silica is particularly preferable. The inorganic oxide may contain a small amount of carbonates, sulfates, nitrates, and oxides such as $Na_2CO_3$, $K_2CO_3$, $CaCO_3$, $MgCO_3$, $Na_2SO_4$, $Al_2(SO_4)_3$, $BaSO_4$, $KNO_3$, $Mg(NO_3)_2$, $Al(NO_3)_3$, $Na_2O$, $K_2O$, and $Li_2O$.

Examples of the magnesium compound may include magnesium halides such as magnesium chloride, magnesium bromide, magnesium iodide, and magnesium fluoride; alkoxy magnesium halides such as methoxy magnesium chloride, ethoxy magnesium chloride, isopropoxy magnesium chloride, butoxy magnesium chloride, and octoxy magnesium chloride; aryloxy magnesium halides such as phenoxy magnesium chloride, and methylphenoxy magnesium chloride; alkoxy magnesiums such as ethoxy magnesium, isopropoxy magnesium, butoxy magnesium, n-octoxy magnesium, and 2-ethylhexoxy magnesium; aryloxy magnesiums such as phenoxy magnesium and dimethylphenoxy magnesium; as well as carboxylates of magnesium such as magnesium laurate and magnesium stearate. Among them, preferable is magnesium halide or alkoxy magnesium, further preferable is magnesium chloride or butoxy magnesium.

Examples of the clay or clay mineral may include kaolin, bentonite, kibushi clay, gaerome clay, allophane, hisingerite, pyrophyllite, talc, a mica group, a montmorillonite group, vermiculite, a chlorite group, palygorskite, kaolinite, nacrite, dickite, and halloysite. Among them, preferable is smectite, montmorillonite, hectorite, laponite, or saponite, and further preferably montmorillonite or hectorite.

It is preferable that the inorganic substance has been dried to substantially remove moisture, and an inorganic substance which has been dried by heat treatment is preferable. The heat treatment, regarding an inorganic substance in which moisture cannot be confirmed visually, is usually performed at a temperature of 100 to 1,500° C., preferably 100 to 1,000° C., further preferably 200 to 800° C. The heating time is not particularly limited, but is preferably 10 minutes to 50 hours, more preferably 1 hour to 30 hours. Examples of a drying method may include a method of flowing a dried inert gas (e.g. nitrogen or argon) under heating at a constant flow rate, and a method of reducing pressure under heating.

The average particle diameter of the inorganic substance is preferably 5 to 1000 μm, more preferably 10 to 500 μm, and further preferably 10 to 100 μm, the pore volume is preferably 0.1 ml/g or more, and further preferably 0.3 to 10 ml/g, and the specific surface area is preferably 10 to 1000 m$^2$/g, and more preferably 100 to 500 m$^2$/g.

As the organic polymer in the particle (d), a polymer having a functional group having active hydrogen or a Lewis basic functional group with non-proton donating property is preferable.

Examples of the functional group having active hydrogen may include a primary amino group, a secondary amino group, an imino group, an amido group, a hydrazido group, an amidino group, a hydroxy group, a hydroperoxy group, a carboxyl group, a formyl group, a carbamoyl group, a sulfonic acid group, a sulfinic acid group, a sulfenic acid group, a thiol group, a thioformyl group, a pyrrolyl group, an imidazolyl group, a piperidyl group, an indazolyl group, and a carbazolyl group. Among them, preferable is a primary amino group, a secondary amino group, an imino group, an amido group, an imido group, a hydroxy group, a formyl group, a carboxyl group, a sulfonic acid group or a thiol group, and particularly preferable is a primary amino group, a secondary amino group, an amido group or a hydroxy group. These groups may be substituted with a halogen atom, or a hydrocarbyl group having 1 to 20 carbon atoms.

Examples of the Lewis basic functional group with non-proton donating property may include a pyridyl group, an N-substituted imidazolyl group, an N-substituted indazolyl group, a nitrile group, an azido group, an N-substituted imino group, an N,N-substituted amino group, an N,N-substituted aminooxy group, an N,N,N-substituted hydrazino group, a nitroso group, a nitro group, a nitrooxy group, a furyl group, a carbonyl group, a thiocarbonyl group, an alkoxy group, an alkyloxycarbonyl group, an N,N-substituted carbamoyl group, a thioalkoxy group, a substituted sulfinyl group, a substituted sulfonyl group, and a substituted sulfonic acid group. Among them, preferable is a heterocyclic group, further preferable is an aromatic heterocyclic group having an oxygen atom and/or a nitrogen atom in a ring, particularly preferable is a pyridyl group, an N-substituted imidazolyl group, or an N-substituted indazolyl group, most preferable is a pyridyl group. These groups may be substituted with a halogen atom, or a hydrocarbyl group having 1 to 20 carbon atoms.

The amount of the functional group having active hydrogen or the Lewis basic functional group with non-proton donating property is preferably 0.01 to 50 mmol/g, more preferably 0.1 to 20 mmol/g as a molar amount of a functional group per gram of a polymer unit.

Examples of a process for producing a polymer having the functional group may include a method of mono-polymerizing a monomer having a functional group having active hydrogen or a Lewis basic functional group with non-proton donating property, and one or more polymerizable unsaturated groups, and a method of copolymerizing the monomer and other monomers having a polymerizable unsaturated group. It is preferable that the monomer is combined with a crosslinking polymerizable monomer having two or more polymerizable unsaturated groups. Examples of the monomer having a functional group having active hydrogen or a Lewis basic functional group which is non-proton donating property, and one or more polymerizable unsaturated groups may include (1) a monomer having a functional group having active hydrogen and one or more polymerizable unsaturated groups, and (2) a monomer having a Lewis basic functional group with non-proton donating property and one or more polymerizable unsaturated groups.

Examples of the monomer having a functional group having active hydrogen and one or more polymerizable unsaturated groups may include a vinyl group-containing primary amine, a vinyl group-containing secondary amine, a vinyl group-containing amide compound, and a vinyl group-containing hydroxy compound. Specific examples thereof may include N-(1-ethenyl)amine, N-(2-propenyl)amine, N-(1-ethenyl)-N-methylamine, N-(2-propenyl)-N-methylamine, 1-ethenylamide, 2-propenylamide, N-methyl-(1-ethenyl)amide, N-methyl-(2-propenyl)amide, vinyl alcohol, 2-propene-1-ol, and 3-butene-1-ol. Examples of the monomer having a Lewis basic functional group with non-proton donating property and one or more polymerizable unsaturated groups may include vinylpyridine, vinyl(N-substituted)imidazole, and vinyl(N-substituted)indazole.

Examples of the other monomers having a polymerizable unsaturated group may include ethylene, α-olefin, and an aromatic vinyl compound, and specific examples thereof may include ethylene, propylene, 1-butene, 1-hexene, 4-methyl-1-pentene, styrene, and a combination of two or more of them. Among them, preferable is ethylene or styrene. Examples of the crosslinking polymerizable monomer having two or more polymerizable unsaturated groups may include divinylbenzene.

The average particle diameter of the organic polymer is preferably 5 to 1000 μm, and more preferably 10 to 500 μm, the pore volume is preferably 0.1 ml/g or more, and more preferably 0.3 to 10 ml/g, and the specific surface area is preferably 10 to 1000 m$^2$/g, and more preferably 50 to 500 m$^2$/g.

It is preferable that the organic polymer has been dried to substantially remove moisture, and an organic polymer which has been dried by heat treatment is preferable. The heat treatment, regarding an organic polymer in which moisture cannot be confirmed visually, is usually performed at a temperature of 30 to 400° C., preferably 50 to 200° C., further preferably 70 to 150° C. The heating time is not particularly limited, but is preferably 30 minutes to 50 hours, more preferably 1 hour to 30 hours. Examples of a drying method may include a method of flowing a dried inert gas (e.g. nitrogen or argon) under heating at a constant flow rate, and a method of decreasing pressure under heating.

The order of bringing the compound (a), the compound (b), the compound (c) and the particle (d) into contact with each other is not particularly limited, and the following orders can be exemplified:

(1) A contacted substance obtained by bringing a contacted substance of (a) and (b) into contact with (c) brings into contact with (d);
(2) A contacted substance obtained by bringing a contacted substance of (a) and (b) into contact with (d) brings into contact with (c);
(3) A contacted substance obtained by bringing a contacted substance of (a) and (c) into contact with (b) brings into contact with (d);
(4) A contacted substance obtained by bringing a contacted substance of (a) and (c) into contact with (d) brings into contact with (b);
(5) A contacted substance obtained by bringing a contacted substance of (a) and (d) into contact with (b) brings into contact with (c);
(6) A contacted substance obtained by bringing a contacted substance of (a) and (d) into contact with (c) brings into contact with (b);

(7) A contacted substance obtained by bringing a contacted substance of (b) and (c) into contact with (a) brings into contact with (d);
(8) A contacted substance obtained by bringing a contacted substance of (b) and (c) into contact with (d) brings into contact with (a);
(9) A contacted substance obtained by bringing a contacted substance of (b) and (d) into contact with (a) brings into contact with (c);
(10) A contacted substance obtained by bringing a contacted substance of (b) and (d) into contact with (c) brings into contact with (a);
(11) A contacted substance obtained by bringing a contacted substance of (c) and (d) into contact with (a) brings into contact with (b); and
(12) A contacted substance obtained by bringing a contacted substance of (c) and (d) into contact with (b) brings into contact with (a).

Among them, preferable is order (1), (2), (11) or (12).

It is preferable that the contact is performed under an inert gas atmosphere. The temperature for contact is usually −100 to 300° C., preferably −80 to 200° C., and the time is usually 1 minute to 200 hours, preferably 10 minutes to 100 hours. The contact is performed using a solvent or without using a solvent.

As the solvent, usually, a solvent which does not react with the compounds (a) to (c), the particle (d), or the contacted substances in each contact step among the orders (1) to (12) (e.g. in the case of the order (1), the step of bringing (a) into contact with (b), the step of bringing the contacted substance into contact with (c), and the step of bringing the contacted substance into contact with (d)) is used.

Examples of the solvent may include non-polar solvents such as an aliphatic hydrocarbyl solvent and an aromatic hydrocarbyl solvent, as well as polar solvents such as a halide solvent, an ether-based solvent, an alcohol-based solvent, a phenol-based solvent, a carbonyl-based solvent, a phosphoric acid derivative, a nitrile-based solvent, a nitro compound, an amine-based solvent, and a sulfur compound. Specific examples thereof may include aliphatic hydrocarbyl solvents such as butane, pentane, hexane, heptane, octane, 2,2,4-trimethylpentane, and cyclohexane; aromatic hydrocarbyl solvents such as benzene, toluene and xylene; halide solvents such as dichloromethane, dichlorodifluoromethanechloroform, 1,2-dichloroethane, 1,2-dibromoethane, 1,1,2-trichloro-1,2,2-trifluoroethane, tetrachloroethylene, chlorobenzene, bromobenzene, and o-dichlorobenzene; ether-based solvents such as dimethyl ether, diethyl ether, diisopropyl ether, di-n-butyl-ether, methyl-tert-butyl-ether, anisole, 1,4-dioxane, 1,2-dimethoxyethane, bis(2-methoxyethyl)ether, tetrahydrofuran, and tetrahydropyran; alcohol-based solvents such as methanol, ethanol, 1-propanol, 2-propanol, 1-butanol, 2-butanol, 2-methyl-1-propanol, 3-methyl-1-butanol, cyclohexanol, benzyl alcohol, ethylene glycol, propylene glycol, 2-methoxyethanol, 2-ethoxyethanol, diethylene glycol, triethylene glycol, and glycerin; phenol-based solvents such as phenol and p-cresol; carbonyl-based solvents such as acetone, ethyl methyl ketone, cyclohexanone, acetic anhydride, ethyl acetate, butyl acetate, ethylene carbonate, propylene carbonate, N,N-dimethylformamide, N,N-dimethylacetamide, and N-methyl-2-pyrrolidone; phosphoric acid derivatives such as hexamethylphosphoric triamide and triethyl phosphate; nitrile-based solvents such as acetonitrile, propionitrile, succinonitrile, and benzonitrile; nitro compounds such as nitromethane and nitrobenzene; amine-based solvents such as pyridine, piperidine and morpholine; as well as sulfur compounds such as dimethyl sulfoxide and sulfolane.

In the case of the orders (1), (3) and (7), a solvent for producing a contacted substance of (a), (b) and (c), that is, a contacted substance used for bringing into contact with the particle (d) is preferably an aliphatic hydrocarbyl solvent, an aromatic hydrocarbyl solvent or an ether-based solvent.

On the other hand, a solvent upon contact between the contacted substance and the particle (d) is preferably a polar solvent. As an index for expressing the polarity of the solvent, an $E_T^N$ value (C. Reichardt, "Solvents and Solvents Effects in Organic Chemistry", $2^{nd}$ ed., VCH Verlag (1988).) is known, and as the polar solvent, a solvent satisfying $0.8 \geqq E_T^N \geqq 0.1$ is particularly preferable. Examples of the polar solvent may include dichloromethane, dichlorodifluoromethanechloroform, 1,2-dichloroethane, 1,2-dibromoethane, 1,1,2-trichloro-1,2,2-trifluoroethane, tetrachloroethylene, chlorobenzene, bromobenzene, o-dichlorobenzene, dimethyl ether, diethyl ether, diisopropyl ether, di-n-butyl ether, methyl-tert-butyl ether, anisole, 1,4-dioxane, 1,2-dimethoxyethane, bis(2-methoxyethyl)ether, tetrahydrofuran, tetrahydropyran, methanol, ethanol, 1-propanol, 2-propanol, 1-butanol, 2-butanol, 2-methyl-1-propanol, 3-methyl-1-butanol, cyclohexanol, benzyl alcohol, ethylene glycol, propylene glycol, 2-methoxyethanol, 2-ethoxyethanol, diethylene glycol, triethylene glycol, acetone, ethyl methyl ketone, cyclohexanone, acetic anhydride, ethyl acetate, butyl acetate, ethylene carbonate, propylene carbonate, N,N-dimethylformamide, N,N-dimethylacetamide, N-methyl-2-pyrrolidone, hexamethylphosphoric triamide, triethyl phosphate, acetonitrile, propionitrile, succinonitrile, benzonitrile, nitromethane, nitrobenzene, ethylenediamine, pyridine, piperidine, morpholine, dimethyl sulfoxide, and sulfolane. Among them, preferable is dimethyl ether, diethyl ether, diisopropyl ether, di-n-butyl ether, methyl-tert-butyl ether, anisole, 1,4-dioxane, 1,2-dimethoxyethane, bis(2-methoxyethyl)ether, tetrahydrofuran, tetrahydropyran, methanol, ethanol, 1-propanol, 2-propanol, 1-butanol, 2-butanol, 2-methyl-1-propanol, 3-methyl-1-butanol, cyclohexanol, benzyl alcohol, ethylene glycol, propylene glycol, 2-methoxyethanol, 2-ethoxyethanol, diethylene glycol or triethylene glycol, particularly preferable is di-n-butyl ether, methyl-tert-butyl ether, 1,4-dioxane, tetrahydrofuran, methanol, ethanol, 1-propanol, 2-propanol, 1-butanol, 2-butanol, 2-methyl-1-propanol, 3-methyl-1-butanol or cyclohexanol, most preferable is tetrahydrofruan, methanol, ethanol, 1-propanol or 2-propanol.

In addition, the solvent upon contact between the contacted substance and the particle (d) may be a mixed solvent of a polar solvent and a hydrocarbyl solvent. Examples of the hydrocarbyl solvent may include the aliphatic hydrocarbyl solvent and the aromatic hydrocarbyl solvent. Examples of the mixed solvent of a polar solvent and a hydrocarbyl solvent may include a hexane/methanol mixed solvent, a hexane/ethanol mixed solvent, a hexane/1-propanol mixed solvent, a hexane/2-propanol mixed solvent, a heptane/methanol mixed solvent, a heptane/ethanol mixed solvent, a heptane/1-propanol mixed solvent, a heptane/2-propanol mixed solvent, a toluene/methanol mixed solvent, a toluene/ethanol mixed solvent, a toluene/1-propanol mixed solvent, a toluene/2-propanol mixed solvent, a xylene/methanol mixed solvent, a xylene/ethanol mixed solvent, a xylene/1-propanol mixed solvent and a xylene/2-propanol mixed solvent. Among them, preferable is a hexane/methanol mixed solvent, a hexane/ethanol mixed solvent, a heptane/methanol mixed solvent, a heptane/ethanol mixed solvent, a toluene/methanol mixed solvent, a toluene/ethanol mixed solvent, a xylene/methanol mixed solvent, or a xylene/ethanol mixed solvent, further preferable is a hexane/methanol mixed solvent, a hexane/ethanol mixed solvent, a toluene/methanol mixed solvent or a toluene/ethanol mixed solvent, most preferable is a mixed solvent of preferably 50 to 90% by volume, further preferably 70 to 85% by volume of toluene, and preferably 10 to 50% by volume, further preferably 15 to 30% by volume of ethanol (the total of both solvents is adjusted to 100% by volume).

In all contact steps of the orders (1), (3) and (7), only a hydrocarbyl solvent may be used. In this case, a time interval from the time point of production of the contacted substance of (a), (b) and (c) to the time point of contact between the contacted substance and the particle (d) is preferably shorter. The time interval is preferably 0 to 5 hours, further preferably 0 to 3 hours, most preferably 0 to 1 hour. The temperature upon contact between the contacted substance and the particle (d) is usually −100° C. to 40° C., preferably −20° C. to 200° C., most preferably −10° C. to 10° C.

The orders (2), (5), (6) and (8) to (12) can use any of a non-polar solvent and a polar solvent. Among them, a non-polar solvent is preferable, because a contacted substance of (a) and (c), or a contacted substance obtained by bringing a contacted substance of (a) and (b) into contact with (c) is generally low in solubility in a non-polar solvent and, therefore, it is easily precipitated on the surface of the particle (d). That is, in the case where the contacted substance is immobilized on the surface of the particle (d), when a polar solvent is used, since the contacted substance has high solubility in polar solvent, it is difficult to immobilize the contacted substance on the surface of the particle (d).

The amounts of the compounds (a), (b) and (c) to be used are not particularly limited, but when the amount of the compound (b) to be used per 1 mol of the compound (a) is y mol, and the amount of the compound (c) to be used per 1 mol of the compound (a) is z mol, it is preferable that y and z substantially satisfy the following formula (x):

$$|d-y-2z| \leq 1 \quad (X)$$

wherein d represents a valence of W.

y is preferably 0.01 to 1.99, more preferably 0.10 to 1.80, further preferably 0.20 to 1.50, most preferably 0.30 to 1.00. z is determined by d, y and the formula (X).

The phrase "substantially satisfies the formula (X)" means that it is intended to use each compound so as to satisfy the formula (X) even when this formula is not completely satisfied. This is because even when each compound is used so as to completely satisfy the formula (X), the amount to be used subtly varies in some cases and, usually, in view of the amount of a compound which is unreacted and remains, the amount to be used is appropriately increased or decreased.

The particle (d) is used such an amount that 1 gram of a modified particle (I) contains 0.1 mmol or more, preferably 0.5 to 20 mmol of a typical metal atom derived from the compound (a).

A final contacted substance (reaction product) obtained in the orders (1) to (12) is preferably heated in order to further proceed the reaction. Examples of an aspect of the heating may include a method of substituting a solvent used in the contact step with a solvent having a higher boiling point in order to heat at a higher temperature.

In order to remove unreacted compounds (a) to (c) and an unreacted particle (d) contained in the obtained modified particle (I), it is preferable to wash the modified particle (I) with a solvent which is the same as, or different from the solvent at the contact.

It is preferable that the washed modified particle (I) is dried at 25° C. or higher for 1 hour to 24 hours, preferably at 40° C. to 200° C. for 1 hour to 24 hours, more preferably at 60° C. to 200° C. for 1 hour to 24 hours, further preferably at 60° C. to 160° C. for 2 hours to 18 hours, most preferably at 80° C. to 160° C. for 4 hours to 18 hours, under reduced pressure.

(II) Modified particle obtained by bringing alumoxane into contact with particle (d)

The alumoxane is preferably alumoxane represented by the following formula:

Cyclic alumoxane of $\{-Al(E^2)-O-\}_b$

Linear alumoxane of $E^3\{-Al(E^3)-O-\}_c AlE^3_2$ wherein $E^2$ and $E^3$ are each a hydrocarbyl group, preferably a hydrocarbyl group having 1 to 8 carbon atoms, more preferably an alkyl group, all $E^2$s and all $E^3$s are the same as, or different from one another; Y represents a hydrogen atom or a halogen atom, and all Ys are the same as, or different from each other; a presents a number satisfying $0<a\leq3$; b represents an integer of 2 or more, preferably 2 to 40; c represents an integer of 1 or more, preferably an integer of 1 to 40.

Examples of $E^2$ and $E^3$ may include alkyl groups such as a methyl group, an ethyl group, a n-propyl group, an isopropyl group, a n-butyl group, an isobutyl group, a n-pentyl group, and a neopentyl group. Among them, preferable is a methyl group or an isobutyl group.

The alumoxane may be known alumoxane, and examples of a process for producing thereof may include a method of bringing a solution of trialkylaluminum (e.g. trimethylaluminum) in an organic solvent (e.g. benzene, toluene or aliphatic hydrocarbyl) into contact with water, and a method of bringing trialkylaluminum (e.g. trimethylaluminum) into contact with a metal salt containing crystal water (e.g. copper sulfate hydrate). It is supposed that the alumoxane obtained by these methods is usually a mixture of cyclic alumoxane and linear alumoxane.

A method of bringing alumoxane into contact with the particle (d) is not particularly limited, and examples of the method may include a method of adding alumoxane to a solvent in which the particle (d) has been dispersed. Examples of the solvent may include the above-descried solvents, a solvent which does not react with alumoxane is preferable, and a solvent which dissolves alumoxane is more preferable. The solvent is preferably an aromatic hydrocarbyl solvent such as benzene, toluene or xylene, or an aliphatic hydrocarbyl solvent such as hexane, heptane or octane, further preferably toluene or xylene.

The temperature and the time for bringing alumoxane into contact with the particle (d) are not particularly limited, and the temperature is usually −100° C. to 200° C., preferably −50° C. to 150° C., further preferably −20° C. to 120° C. Particularly at the initial stage of the contact, contact at a low temperature is preferable in order to suppress heat production due to the reaction. The amounts of alumoxane and the particle (d) to be used are not particularly limited. Alumoxane is usually 0.01 to 100 mmol, preferably 0.1 to 20 mmol, further preferably 1 to 10 mmol per unit gram of the particle (d), in terms of an aluminum atom in the alumoxane to be used.

In the process for producing a polymerization catalyst of the present invention, a method of bringing the transition metal compound into contact with the co-catalytic component for activation is not particularly limited. Examples of the contacting method may include a method of supplying a mixture of both to a polymerization tank, and a method of supplying both to a polymerization tank separately. In these methods, a part of the co-catalytic component for activation and the transition metal compound are supplied to a polymerization tank and, then, the remaining part may be supplied. The contact is performed using a solvent or without using a solvent.

The temperature for bringing the transition metal compound into contact with the co-catalytic component for activation is not particularly limited, and is in a range of usually −100° C. to 150° C., preferably −50° C. to 100° C., more preferably −10° C. to 80° C., particularly preferably 0° C. to 50° C. The time for bringing the transition metal compound into contact with the co-catalytic component for activation is not particularly limited, and is in a range of usually 0 to 24 hours, preferably 0 to 6 hours, more preferably 0 to 3 hours, particularly preferably 0 to 1 hour.

The organoaluminum compound A-1 is used in an amount of 0.1 to 10,000 mol, preferably 5 to 2,000 mol per 1 mol of the transition metal compound. The boron compound is used in an amount of 0.01 to 100 mol, preferably 0.5 to 10 mol per 1 mol of the transition metal compound.

When a solvent is used, the concentration of the transition metal compound is usually 0.0001 to 1000 mmol/L, more preferably 0.05 to 200 mmol/L, further preferably 0.01 to 50 mmol/L, the concentration of the organoaluminum compound A-1 is usually 0.01 to 5000 mmol/L, more preferably 0.1 to 2500 mmol/L, further preferably 0.1 to 2000 mmol/L in terms of an aluminum atom, and the concentration of the boron compound is usually 0.001 to 500 mmol/L, more preferably 0.01 to 250 mmol/L, further preferably 0.05 to 100 mmol/L.

A polymerization method in the process for producing an olefin polymer of the present invention is not particularly limited. Examples of the polymerization method may include solvent polymerization or slurry polymerization using, as a solvent, aliphatic hydrocarbyls such as butane, pentane, hexane, heptane, and octane, aromatic hydrocarbyls such as benzene and toluene, or halogenated hydrocarbyls such as methylene dichloride, as well as vapor phase polymerization in a gaseous monomer, and continuous polymerization or batch polymerization is performed.

The polymerization temperature is usually −50° C. to 200° C., particularly preferably −20° C. to 100° C., and the polymerization pressure is preferably normal pressure to 6 MPa. The polymerization time is generally appropriately determined depending on the kind of an objective polymer and a reaction apparatus, and is usually 1 minute to 20 hours. In order to adjust the molecular weight of a polymer, a chain transfer agent such as hydrogen may be added.

It is preferable that the modified particle (I) or (II) is used in combination with the following organoaluminum compound (hereinafter, referred to as "organoaluminum compound A-2"). A preferable catalyst for olefin polymerization in the present invention is a catalyst for polymerization obtained by bringing a catalyst component comprising the transition metal compound represented by the formula (1), a co-catalytic component for activation comprising the modified particle (I) or (II), and the organoaluminum compound A-2 into contact with each other.

The organoaluminum compound A-2 may be a known compound, and is preferably a compound represented by the following formula [7]:

$$R^{17}{}_c AlY^2{}_{3-c} \quad [7]$$

wherein $R^{17}$ represents a hydrocarbyl group, all $R^{17}$s are the same as, or different from each other, $Y^2$ represents a hydrogen atom, a halogen atom, an alkoxy group, an aralkyloxy group or an aryloxy group, all $Y^2$s are the same as, or different from each other, and c represents a number satisfying $0 < c \leq 3$.

$R^{17}$ is preferably a hydrocarbyl group having 1 to 24 carbon atoms, more preferably an alkyl group having 1 to 24 carbon atoms. Examples of $R^{17}$ may include a methyl group, an ethyl group, a n-propyl group, a n-butyl group, an isobutyl group, a n-hexyl group, a 2-methylhexyl group, and a n-octyl group. Among them, preferable is an ethyl group, a n-butyl group, an isobutyl group, a n-hexyl group or a n-octyl group.

Examples of the halogen atom of $Y^2$ may include a fluorine atom, a chlorine atom, a bromine atom and an iodide atom, preferable is a chlorine atom.

The alkoxy group of $Y^2$ is preferably an alkoxy group having 1 to 24 carbon atoms. Examples of the alkoxy group may include a methoxy group, an ethoxy group, a n-propoxy group, an isopropoxy group, a n-butoxy group, a sec-butoxy group, a t-butoxy group, a n-pentoxy group, a neopentoxy group, a n-hexoxy group, a n-octoxy group, a n-dodesoxy group, a n-pentadesoxy group, and a n-icosoxy group. Among them, preferable is a methoxy group, an ethoxy group or a t-butoxy group.

The aryloxy group of $Y^2$ is preferably an aryloxy group having 6 to 24 carbon atoms. Examples of the aryloxy group may include a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexylphenoxy group, a n-octylphenoxy group, a n-decylphenoxy group, a n-tetradecylphenoxy group, a naphthoxy group, and an anthracenoxy group.

The aralkyloxy group of $Y^2$ is preferably an aralkyloxy group having 7 to 24 carbon atoms. Examples of the aralkyloxy group may include a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl)methoxy group, a (2,6-dimethylphenyl)methoxy group, a (3,4-dimethylphenyl)methoxy group, a (3,5-dimethylphenyl)methoxy group, a (2,3,4-trimethylphenyl)methoxy group, a (2,3,5-trimethylphenyl)methoxy group, a (2,3,6-trimethylphenyl)methoxy group, a (2,4,5-trimethylphenyl)methoxy group, a (2,4,6-trimethylphenyl)methoxy group, a (3,4,5-trimethylphenyl)methoxy group, a (2,3,4,5-tetramethylphenyl)methoxy group, a (2,3,5,6-tetramethylphenyl)methoxy group, a (pentamethylphenyl)methoxy group, an (ethylphenyl)methoxy group, a (n-propylphenyl)methoxy group, an (isopropylphenyl)methoxy group, a (n-butylphenyl)methoxy group, a (sec-butylphenyl)methoxy group, a (tert-butylphenyl)methoxy group, a (n-hexylphenyl)methoxy group, a (n-octylphenyl)methoxy group, a (n-decylphenyl)methoxy group, a (n-tetradecylphenyl)methoxy group, a naphthylmethoxy group, and an anthracenylmethoxy group. Among them, preferable is a benzyloxy group.

Examples of the organoaluminum compound A-2 represented by the formula [7] may include trialkylaluminums such as trimethylaluminum, triethylaluminum, tri-n-propylaluminum, tri-n-butylaluminum, triisobutylaluminum, tri-n-hexylaluminum, and tri-n-octylaluminum; dialkylaluminum chlorides such as dimethylaluminum chloride, diethylaluminum chloride, di-n-propylaluminum chloride, di-n-butylaluminum chloride, diisobutylaluminum chloride, and di-n-hexylaluminum chloride; alkylaluminum dichlorides such as methylaluminum dichloride, ethylaluminum dichloride, n-propylaluminum dichloride, n-butylaluminum dichloride, isobutylaluminum dichloride, and n-hexylaluminum dichloride; dialkylaluminum hydrides such as dimethylaluminum hydride, diethylaluminum hydride, di-n-propylaluminum hydride, di-n-butylaluminum hydride, diisobutylaluminum hydride, and di-n-hexylaluminum hydride; trialkoxyaluminums such as trimethoxyaluminum, triethoxyaluminum, and tri(t-butoxy)aluminum; alkyl(dialkoxy)aluminums such as methyl(dimethoxy)aluminum, methyl(diethoxy)aluminum, and methyl(di-t-butoxy)aluminum; dialkyl(alkoxy)aluminums such as dimethyl(methoxy)aluminum, dimethyl(ethoxy)aluminum, and dimethyl(t-butoxy)aluminum; triaryloxyaluminums such as trip henoxyaluminum, tris(2,6-diisopropylphenoxy)aluminum, and tris(2,6-diphenylphenoxy)aluminum; alkyl(diaryloxy)aluminums such as methyl(diphenoxy)aluminum, methylbis(2,6-diisopropylphenoxy)aluminum, and methylbis(2,6-diphenylphenoxy)aluminum; as well as dialkyl(aryloxy)aluminums such as dimethyl(phenoxy)aluminum, dimethyl(2,6-diisopropylphenoxy)aluminum, and dimethyl(2,6-diphenylphenoxy) aluminum, and a combination of two or more of these compounds. Among them, preferable is trialkylaluminum, further preferable is trimethylaluminum, triethylaluminum, tri-n-butylaluminum, triisobutylaluminum, tri-n-hexylaluminum or tri-n-octylaluminum, particularly preferable is triisobutylaluminum or tri-n-octylaluminum.

The amount of the transition metal compound represented by the formula (1) to be used is usually $1\times10^{-6}$ to $1\times10^{-3}$ mol, preferably $5\times10^{-6}$ to $5\times10^{-4}$ mol per 1 g of the modified particle (I) or (II).

The amount of the organoaluminum compound A-2 to be used is preferably 0.01 to 10,000 mol, more preferably 0.1 to 5,000 mol, most preferably 1 to 2,000 mol per 1 mol of a transition metal atom in the transition metal compound to be used, in terms of mol of an aluminum atom in the organoaluminum compound A-2 to be used.

In the process for producing a catalyst for polymerization of the present invention, examples of a method of supplying the transition metal compound, the modified particle and the organoaluminum compound to a polymerization reaction apparatus may include (1) a method of supplying a contacted substance of these components to a polymerization reaction apparatus, (2) a method of supplying these components to a polymerization reaction apparatus separately, and (3) a method of supplying a contacted substance of arbitrary two components of these components, and the remaining component to a polymerization reaction apparatus separately.

These components are supplied in the solid state, or the solution state, the suspension state or the slurry state using a hydrocarbyl solvent from which a component inactivating a catalyst component such as moisture and oxygen has been sufficiently removed. The concentration of the transition metal compound in a solution, a suspension and a slurry is usually 0.0001 to 1000 mmol/L, preferably 0.01 to 50 mmol/L in terms of a transition metal compound in the compound, the concentration of the modified particle is usually 0.01 to 1000 g/L, preferably 0.1 to 500 g/L, and the concentration of the organoaluminum compound is usually 0.0001 to 100 mol/L, preferably 0.01 to 10 mon in terms of an Al atom in the compound.

In a process for producing a catalyst for polymerization comprising a step of bringing the transition metal compound represented by the formula (1), the organoaluminum compound A-1 and/or the boron compound into contact with each other, or in a process for producing a catalyst for polymerization comprising a step of bringing the transition metal compound, the modified particle and the organoaluminum compound A-2 into contact with each other, a compound having active hydrogen described in JP-A-2005-126628, or an electron donating compound described in JP-A-2005-126627 may be further contacted. The compound having active hydrogen or the electron donating compound is preferably tertiary amine or secondary amine, more preferably tertiary amines such as triethylamine and tri-n-octyl amine. In the latter process for producing a catalyst for polymerization, the lower limit amount of the compound having active hydrogen or the electron donating compound to be used is preferably 0.1 mol % or more, more preferably 1 mol % or more per 1 mol of an aluminum atom of the organoaluminum compound A-2, and the upper limit amount is preferably 30 mol % or less, more preferably 20 mol % or less, from the viewpoint of enhancing polymerization activity.

Examples of the process for producing an olefin polymer of the present invention may include vapor phase polymerization in a gaseous monomer, as well as solution polymerization and slurry polymerization using a solvent. Examples of the solvent may include aliphatic hydrocarbyl solvents such as butane, pentane, hexane, heptane and octane; aromatic hydrocarbyl solvents such as benzene and toluene; as well as halogenated hydrocarbyl solvents such as methylene chloride. In bulk polymerization, an olefin to be polymerized can be used as a solvent. Polymerization is batch polymerization or continuous polymerization, and the polymerization may be performed by dividing into two or more stages having different reaction conditions.

In the slurry polymerization, a known polymerization method and polymerization conditions can be utilized. Examples of the preferable slurry polymerization method may include a continuous reactor for continuously adding a supply substance such as a monomer (and a comonomer) or a diluent as necessary, and taking out the produced polymer continuously or at least periodically. Examples of the reactor may include a loop reactor, and a reactor in which a plurality of stirring reactors having different structures and conditions are arranged in series, in parallel or in combination thereof. Examples of the diluent may include inert diluents (media) such as paraffin, cycloparaffin and aromatic hydrocarbyl.

The temperature of a polymerization reactor or a reaction zone is usually about 0° C. to about 150° C., preferably 30° C. to 100° C. The polymerization time is appropriately determined depending on the kind of an objective olefin polymer and a reaction apparatus, and is generally 1 minute to 20 hours. The polymerization pressure is usually about 0.1 MPa to about 10 MPa, preferably 0.5 MPa to 5 MPa. It can be utilized such pressure that a monomer and a comonomer are brought into contact with each other in the state where a catalyst is maintained in the suspension state, and where a medium and at least a part of a monomer and comonomer are retained in the liquid phase. Therefore, a medium, a temperature and pressure may be selected such that the polymer is produced as a solid particle, and is recovered in that form.

The molecular weight of the polymer can be controlled by a known means, such as regulation of the temperature of a reaction zone and introduction of hydrogen.

Each catalyst component or a monomer (and a comonomer) can be added to a reactor or a reaction zone in any order, by an arbitrary known method. Examples of a method of addition may include a method of adding each catalyst component and a monomer (and a comonomer) to a reaction zone simultaneously, and a method of adding them sequentially. Each catalyst component may be pre-contacted in an inert atmosphere, before bringing into contact with a monomer (and a comonomer).

Vapor phase polymerization can be performed according to a known polymerization method and known polymerization conditions. Examples of the reaction apparatus may include a fluidized bed-type reaction tank. Preferable is a fluidized bed-type reaction tank having an extension part. A stirring wing may be provided in the reaction tank. Examples of a method of supplying each component to a polymerization tank may include a method of supplying each component using an inert gas such as nitrogen or argon, hydrogen or ethylene, in the state where there is no moisture, and a method of supplying each component in the solution or slurry state, by dissolving or diluting each component in a solvent. Each catalyst component may be supplied separately, or arbitrary components may be pre-contacted in an arbitrary order to be supplied.

The polymerization temperature is lower than the temperature at which a polymer is melted, preferably 0° C. to 150° C., particularly preferably 30° C. to 100° C. For the purpose of regulating the melt flowability of a final product, hydrogen as a molecular weight regulating agent may be added. Upon polymerization, an inert gas may be co-present in a mixed gas.

In the present invention, pre-polymerization described below may be performed before performing such polymerization (main polymerization). It is preferable that, in the pre-polymerization, a small amount of an olefin may be subjected to slurry polymerization in the presence of the transition metal compound represented by the formula (1), the modified particle, and the organoaluminum compound A-2. Examples of a solvent for slurry polymerization may include inert hydrocarbyls such as propane, butane, isobutane, pentane, isopentane, hexane, heptane, octane, cyclehexane, benzene, and toluene. A part or all of the solvent may be changed to a liquid olefin.

The amount of the organoaluminum compound A-2 to be used in pre-polymerization is 0.5 to 700 mol, preferably 0.8 to 500 mol, particularly preferably 1 to 200 mol per 1 mol of the transition metal compound.

The amount of an olefin to be pre-polymerized is usually 0.01 to 1000 g, preferably 0.05 to 500 g, particularly preferably 0.1 to 200 g per 1 g of the modified particle.

The slurry concentration of pre-polymerization is preferably 0.1 to 50 g-modified particle/L-solvent, particularly preferably 0.5 to 20 g-modified particle/L-solvent. The pre-polymerization temperature is preferably −20° C. to 100° C., particularly preferably 0° C. to 80° C. The partial pressure of an olefin at a vapor phase part of pre-polymerization is preferably 0.001 MPa to 2 MPa, particularly preferably 0.01 MPa to 1 MPa, but this is not applied to an olefin which is liquid at the pressure and temperature of pre-polymerization. The pre-polymerization time is not particularly limited, and is usually suitably 2 minute to 15 hours.

Examples of a method of supplying the transition metal compound, the modified particle, the organoaluminum compound A-2, and the olefin in the conduct of pre-polymerization may include a method of supplying the olefin after the transition metal compound, the modified particle and optionally the organoaluminum compound A-2 have been brought into contact with each other; a method of supplying the organoaluminum compound A-2 after the transition metal compound, the modified particle and the olefin have been brought into contact with each other; a method of supplying the modified particle after the organoaluminum compound A-2 and the transition metal compound have been brought into contact with each other in the presence of the olefin. It is preferable that, upon contact between the modified particle and the organoaluminum compound A-2, the olefin is present in advance.

Examples of a method of supplying the olefin may include a method of supplying an olefin successively while maintaining so that a polymerization tank has predetermined pressure; a method of supplying all of the predetermined amount of olefin first. In order to regulate the molecular weight of the resulting polymer, a chain transfer agent such as hydrogen may be added.

A material obtained in the pre-polymerization is used as a catalyst component or a catalyst. The pre-polymerized catalyst component is a pre-polymerized catalyst component obtained by pre-polymerizing the olefin in the presence of a primary catalyst obtained by bringing the transition metal compound, the modified particle, and the organoaluminum compound A-2 into contact with each other. The catalyst for olefin polymerization according to the present invention is obtained by bringing the pre-polymerized catalyst component into contact with the organoaluminum compound A-1.

Examples of the olefin used in the process for producing an olefin polymer of the present invention may include an olefin having 2 to 20 carbon atoms; diolefin; cyclic olefin; alkenyl aromatic hydrocarbyl; polar monomer; and a combination of two or more of them.

Examples of the olefin may include olefins such as ethylene, propylene, 1-butene, 1-pentene, 4-methyl-1-pentene, 5-methyl-1-hexene, 1-hexene, 1-heptene, 1-octene, 1-nonene, and 1-decene; diolefins such as 1,5-hexadiene, 1,4-hexadiene, 1,4-pentadiene, 1,7-octadiene, 1,8-nonadiene, 1,9-decadiene, 4-methyl-1,4-hexadiene, 5-methyl-1,4-hexadiene, 7-methyl-1,6-octadiene, 5-ethylidene-2-norbornene, dicyclopentadiene, 5-vinyl-2-norbornene, 5-methyl-2-norbornene, norbornadiene, 5-methylene-2-norbornene, 1,5-cyclooctadiene, 5,8-endomethylenehexahydronaphthalene, 1,3-butadiene, isoprene, 1,3-hexadiene, 1,3-octadiene, 1,3-cyclooctadiene, and 1,3-cyclohexadiene; cyclic olefins such as norbornene, 5-methylnorbornene, 5-ethylnorbornene, 5-butylnorbornene, 5-phenylnorbornene, 5-benzylnorbornene, tetracyclododecene, tricyclodecene, tricycloundecene, pentacyclopentadecene, pentacyclohexadecene, 8-methyltetracyclododecene, 8-ethyltetracyclododecene, 5-acetylnorbornene, 5-acetyloxynorbornene, 5-methoxycarbonylnorbornene, 5-ethoxycarbonylnorbornene, 5-methyl-5-methoxycarbonylnorbornene, 5-cyanonorbornene, 8-methoxycarbonyltetracyclododecene, 8-methyl-8-tetracyclododecene, and 8-cyanotetracyclododecene; alkenyl aromatic hydrocarbyls such as alkenylbenzene including styrene, 2-phenylpropylene, 2-phenylbutene, and 3-phenylpropylene, alkylstyrenes including p-methylstyrene, m-methylstyrene, o-methylstyrene, p-ethylstyrene, m-ethylstyrene, o-ethylstyrene, 2,4-dimethylstyrene, 2,5-dimethylstyrene, 3,4-dimethylstyrene, 3,5-dimethylstyrene, 3-methyl-5-ethylstyrene, p-tertiarybutylstyrene, and p-secondarybutylstyrene, bisalkenylbenzene including divinylbenzene, and alkenylnaphthalene including 1-vinylnaphthalene; polar monomers such as α,β-unsaturated carboxylic acids including acrylic acid, methacrylic acid, fumaric acid, maleic anhydride, itaconic acid, itaconic acid anhydride, and bicyclo(2,2,1)-5-heptene-2,3-dicarboxylic acid, and their salts of metals including sodium, potassium, lithium, zinc, magnesium and calcium, α,β-unsaturated carboxylic acid esters including methyl acrylate, ethyl acrylate, n-propyl acrylate, isopropyl acrylate, t-butyl acrylate, 2-ethylhexyl acrylate, methyl methacrylate, ethyl methacrylate, n-propyl methacrylate, isopropyl methacrylate, n-butyl methacrylate, and isobutyl methacrylate, unsaturated dicarboxylic acids including maleic acid and itaconic acid, vinyl esters including vinyl acetate, vinyl propionate, vinyl caproate, vinyl caprate, vinyl laurate, vinyl stearate, and vinyl trifluoroacetate, and unsaturated carboxylic acid glycidyl esters including glycidyl acrylate, glycidyl methacrylate, and itaconic acid monoglycidyl ester.

The polymer produced by the process for producing an olefin polymer of the present invention is a homopolymer or a copolymer, and examples of the copolymer may include an ethylene-propylene copolymer, an ethylene-1-butene-copolymer, an ethylene-1-hexene copolymer, an ethylene-1-octene copolymer, and a propylene-1-butene-copolymer. Among them, preferable is a copolymer of ethylene and α-olefin, and particularly preferable is a copolymer of ethylene having a polyethylene crystal structure and α-olefin. The α-olefin is preferably an α-olefin having 3 to 8 carbon atoms such as propylene, 1-butene, 1-hexene, and 1-octene.

EXAMPLES

The present invention will be described in more detail below by way of Examples, but the present invention is not limited thereto. The amount of each catalyst component to be used in Examples and Comparative Examples, and the polymerization conditions such as the hydrogen concentration of an ethylene/hydrogen mixed gas were set so that on the assumption that the obtained olefin polymer is used as a film requiring adequate strength and density, the density of the olefin polymer approximates an assumed density. Measured values of each item in Examples were measured by the following methods.

Reference Example 1

Synthesis of 1-bromo-2-(5,6,7,8-tetrahydro-5,5,8,8-tetramethylbenz-f-indenyl)ethane A 1000 mL three-neck flask replaced with nitrogen was charged with 23.0 g (purity 100%, 102 mmol) of 5,6,7,8-tetrahydro-5,5,8,8-tetramethyl-1H-benz-f-indene and 600 mL of tetrahydrofuran, and was cooled in an ice bath, and then 67.1 mL (1.59 M, 107 mmol) of a hexane solution of n-butyllithium was added dropwise. The color of the solution turned from colorless to yellow. The temperature of this solution was gradually raised to room temperature, and the solution was stirred for further 1 hour to prepare a tetrahydrofuran solution of lithium (5,6,7,8-tetrahydro-5,5,5,8-tetramethyl-1H-benz-f-indenide).

Separately, a 2000 mL three-neck flask replaced with nitrogen was charged with 35.5 mL (406 mmol) of dibromoethane and 200 mL of tetrahydrofuran, and was cooled to −78° C. The tetrahydrofuran solution of lithium (5,6,7,8-tetrahydro-5,5,5,8-tetramethyl-1H-benz-f-indenide) which had been previously prepared was gradually added dropwise thereto. The color of the solution turned to pale orange. After completion of dropwise addition, the temperature of the reaction solution was raised to room temperature, and the solution was stirred for further 2 hours. While this solution was cooled in a water bath, 200 mL of distilled water was added dropwise. After the organic layer was separated, the aqueous layer was extracted with ethyl acetate.

The separated organic layer and the extract were combined, washed with an aqueous saturated sodium chloride solution two times, and then dried with sodium sulfate. Volatile components were distilled off under reduced pressure.

Based on the following $^1$H NMR (400 MHz, CDCl$_3$) data, the resulting yellow oily product was identified to be an isomer mixture (94:6) of 1-bromo-2-(5,6,7,8-tetrahydro-5,5,8,8-tetramethylbenz-f-inden-1-yl)ethane and 1-bromo-2-(5,6,7,8-tetrahydro-5,5,8,8-tetramethylbenz-f-inden-3-yl)ethane.

Yield amount 29.9 g (purity 89%, 80 mmol, yield 79%). Due to a minor component, assignments of other peaks were impossible.

1-bromo-2-(5,6,7,8-tetrahydro-5,5,8,8-tetramethylbenz-f-inden-1-yl)ethane: δ 7.35 (s, 1H), 7.30 (s, 1H), 6.79 (dd, 1H, J=5.6, 2.0 Hz), 6.43 (dd, 1H, J=5.6, 2.0 Hz), 3.66 (t, 1H), 3.50 (t, 2H, J=8.0 Hz), 2.42-2.33 (m, 1H), 2.13-2.04 (m, 1H), 1.74 (s, 4H), 1.31 (s, 12H).

1-bromo-2-(5,6,7,8-tetrahydro-5,5,8,8-tetramethylbenz-f-inden-3-yl)ethane: δ 6.24 (s, 1H) 3.63 (m, 2H), 3.31 (s, 2H), 3.12 (t, 2H, J=8.6 Hz).

Example 1

Synthesis of 1,2-bis(5,6,7,8-tetrahydro-5,5,8,8-tetramethylbenz-f-indenyl)ethane A 200 mL two-neck flask replaced with nitrogen was charged with 2.20 g (purity 95%, 10.3 mmol) of 5,6,7,8-tetrahydro-5,5,8,8-tetramethylbenz-f-indene and 48 mL of tetrahydrofuran, and cooled in an ice bath, and then 6.7 mL (1.6 M, 10.8 mmol) of a hexane solution of n-butyllithium was added dropwise. The color of the solution turned from colorless to brown. The temperature of this solution was gradually raised to room temperature, and the solution was stirred for further two hours to prepare a tetrahydrofuran solution of lithium (5,6,7,8-tetrahydro-5,5,8,8-tetramethylbenz-f-indenide). After this solution was cooled to −78° C., a tetrahydrofuran (16 mL) solution of 3.94 g (purity 88%, 10.3 mmol) of 1-bromo-2-(5,6,7,8-tetrahydro-5,5,8,8-tetramethylbenz-f-indenyl)ethane synthesized in Reference Example 1 was added dropwise. After completion of dropwise addition, the temperature of the reaction solution was raised to room temperature, and the solution was stirred for 4 hours. To the reaction solution was added water, and the organic substance was extracted with ethyl acetate. After the separation, the aqueous layer was further extracted with ethyl acetate. All extracts were combined, washed successively with an aqueous saturated ammonium chloride solution and an aqueous saturated sodium chloride solution, and dried with sodium sulfate. Volatile components were distilled off under reduced pressure, and the resulting brownish yellow solid was purified by silica gel column chromatography using a heptane/ethyl acetate (v/v=30/1) mixed solvent as a developing solvent. The resulting yellow solid was washed with ethanol, and dried under reduced pressure. Based on the following NMR data, the resulting pale yellow solid was identified to be bis(5,6,7,8-tetrahydro-5,5,8,8-tetramethylbenz-f-indenyl)ethane.

Yield amount was 1.22 g (purity 93%, 2.37 mmol), and yield was 23%.

$^1$H NMR (CDCl$_3$):

δ 1.29 (s, 4H), 1.31 (s, 24H), 1.62-1.69 (m, 2H), 1.70 (s, 4H), 1.91-1.99 (m, 2H), 3.42 (br, 2H), 6.46 (d, 2H, J=8 Hz), 6.75 (d, 2H, J=8 Hz), 7.29 (s, 2H), 7.36 (s, 2H).

$^{13}$C {$^1$H} NMR (CDCl$_3$):

δ 32.07, 32.09, 32.26, 32.31, 34.40, 34.46, 35.29, 35.33, 50.05, 118.74, 120.85, 130.89, 138.48, 141.37, 141.97, 143.03, 144.77.

Example 2

Synthesis of ethylenebis(5,6,7,8-tetrahydro-5,5,8,8-tetramethylbenz-f-indenyl)zirconium bis(dimethylamide)

A 50 mL Schlenk tube replaced with nitrogen was charged with 1,2-bis(5,6,7,8-tetrahydro-5,5,8,8-tetramethylbenz-f-indenyl)ethane (1.1 g, 2.3 mmol)synthesized in Example 1, tetrakisdimethylaminozirconium (0.65 g, 2.45 mmol), tetra-n-butylammonium chloride (0.06 g, 0.23 mmol), and toluene (25 mL). The temperature of this solution was raised to 100° C., and the solution was stirred for 2 hours. After cooled to room temperature, toluene was distilled off under reduced pressure to obtain a red solid. The red solid was washed with hexane, and extracted with a toluene/hexane (v/v=1/1) mixed solvent, and the extract was filtered with a glass filter on which Celite had been placed. The solvent was distilled off from the filtrate under reduced pressure. Based on the following $^1$H NMR (CDCl$_3$) data, the resulting orange solid was identified to be ethylenebis(5,6,7,8-tetrahydro-5,5,8,8-tetramethylbenz-f-indenyl)zirconium bis(dimethylamide). Yield amount was 0.32 g (0.49 mmol), and yield was 21%.

δ 7.66 (s, 2H), 7.41 (s, 2H), 6.23 (d, 2H, J=4 Hz), 5.92 (d, 2H, J=4 Hz), 3.69-3.66 (m, 2H), 3.44-3.42 (m, 2H), 2.45 (s, 12H), 1.74-1.66 (m, 8H), 1.44 (s, 12H), 1.38 (s, 6H), 1.21 (s, 6H).

Example 3

Synthesis of ethylenebis(5,6,7,8-tetrahydro-5,5,8,8-tetramethylbenz-f-indenyl)zirconium diphenoxide A 50 mL Schlenk tube replaced with nitrogen was charged with ethylenebis(5,6,7,8-tetrahydro-5,5,8,8-tetramethylbenz-f-indenyl)zirconium bis(dimethylamide) (0.67 g, 1.02 mmol) synthesized in Example 2 and toluene (10 ml). After the temperature of this solution was raised to 100° C., a toluene (5 mL) solution of 0.19 g (2.0 mmol) of phenol was added dropwise, and the mixture was stirred for 1 hour. After cooled to room temperature, volatile components were distilled off under reduced pressure, and the resulting solid was extracted with a toluene/heptane (v/v=1/1) mixed solvent. After the extract was filtered with a glass filter on which Celite had been placed, the solvent was distilled off from the filtrate under reduced pressure. The resulting solid was stirred in heptane (18 mL) at 60° C. for 1 hour. After cooled to room temperature, the solid was filtered, and washed with diethyl ether (10 mL) two times. This was dried under reduced pressure. Based on the following $^1$H NMR (CDCl$_3$) data, the resulting pale yellow solid was identified to be ethylenebis(5,6,7,8-tetrahydro-5,5,8,8-tetramethylbenz-f-indenyl)zirconium diphenoxide. Yield amount was 0.37 g (0.49 mmol), and yield was 48%.

δ 7.83 (s, 2H), 7.18 (s, 2H), 7.09 (t, 4H, J=8 Hz), 6.72 (t, 2H, J=8 Hz), 6.30 (d, 4H, J=8 Hz), 6.15 (d, 2H, J=4 Hz), 5.87 (d, 2H, J=4 Hz), 3.96-3.90 (m, 2H), 3.77-3.71 (m, 2H), 1.69-1.64 (m, 4H), 1.57-1.54 (m, 4H), 1.56 (s, 6H), 1.40 (s, 6H), 1.14 (s, 6H), 0.78 (s, 6H).

Reference Example 2

Preparation of Modified Particle (C)

A reactor equipped with a stirrer replaced with nitrogen was charged with 2.8 kg of silica (Sylopol 948 manufactured by Davison; 50% volume average particle diameter=55 μm; pore volume=1.67 ml/g; specific surface area=325 m$^2$/g) which had been heat-treated at 300° C. under a nitrogen stream, and 24 kg of toluene, and the mixture was stirred. Thereafter, after cooled to 5° C., a mixed solution of 0.9 kg of 1,1,1,3,3,3-hexamethyldisilazane and 1.4 kg of toluene was added dropwise for 30 minutes while the temperature of the reactor was maintained at 5° C. After completion of dropwise addition, the mixture was stirred at 5° C. for 1 hour, then, the temperature was raised to 95° C., and the mixture was stirred at 95° C. for 3 hours, and filtered. The resulting solid product was washed with 20.8 kg of toluene six times. Thereafter, 7.1 kg of toluene was added to obtain a slurry, and this was allowed to stand overnight.

Into the resulting slurry were charged 1.73 kg of a hexane solution of diethylzinc (diethylzinc concentration: 50% by weight) and 1.02 kg of hexane, and the mixture was stirred. Thereafter, after cooled to 5° C., a mixed solution of 0.78 kg of 3,4,5-trifluorophenol and 1.44 kg of toluene was added dropwise for 60 minutes while the temperature of the reactor was maintained at 5° C. After completion of dropwise addition, the mixture was stirred at 5° C. for 1 hour, then, the temperature was raised to 40° C., and the mixture was stirred at 40° C. for 1 hour. Thereafter, the mixture was cooled to 22° C., and 0.11 kg of H$_2$O was added dropwise for 1.5 hours while the temperature of the reactor was maintained at 22° C. After completion of dropwise addition, the mixture was stirred at 22° C. for 1.5 hours, then, the temperature was raised to 40° C., the mixture was stirred at 40° C. for 2 hours, the temperature was further raised to 80° C., and the mixture was stirred at 80° C. for 2 hours. After stirring, the supernatant was extracted to a remaining amount of 16 L at room temperature, 11.6 kg of toluene was charged thereinto, then, the temperature was raised to 95° C., and the mixture was stirred for 4 hours.

After stirring, the supernatant was extracted at room temperature to obtain a solid product. The resulting solid product was washed with 20.8 kg of toluene four times, and with 24 L of hexane three times. Thereafter, this was dried to obtain a modified particle (C).

Reference Example 3

Preparation of Modified Particle (D)

A 50 L reactor equipped with a stirrer replaced with nitrogen was charged with 9.68 kg of silica (Sylopol 948 manufactured by Davison; average particle diameter=55 μm; pore volume=1.67 ml/g; specific surface area=325 m$^2$/g) which had been heat-treated at 300° C. under a nitrogen stream, as a solid carrier. After 100 L of toluene was added, the mixture was cooled to 2° C. To this was added dropwise 26.3 L of a toluene solution of methylalumoxane (manufactured by Tosoh Finechem Corporation) (2.9 M) over 1 hour. After stirred at 5° C. for 30 minutes, the mixture was heated to 95° C. over 90 minutes, and stirred for 4 hours. Thereafter, after cooled to 40° C., this was allowed to stand for 40 minutes to settle a solid component, and the slurry part of the upper layer was removed. As washing operation, to this was added 100 L of toluene, the mixture was stirred for 10 minutes, and then stirring was stopped, this was allowed to stand to settle a solid component, and the slurry part of the upper layer was similarly removed. The above washing operation was repeated three times totally. Further, 100 L of toluene was added, the mixture was stirred, and then stirring was stopped and, at the same time, this was filtered. After this operation was repeated one more time, 110 L of hexane was added, and this was filtered by a similar method. This operation was repeated one more time. Thereafter, this was dried at 70° C. for 7 hours under a nitrogen stream to obtain 12.6 kg of a modified particle (D). As a result of elementary analysis, Al=4.4 mmol/g.

Example 4

After drying under reduced pressure, the interior of an autoclave equipped with a stirrer having an internal volume of 3 L, replaced with argon, was made to be vacuum, hydrogen was added so as to have its partial pressure of 0.017 MPa, 71 g of 1-butene as a comonomer, and 679 g of butane as a polymerization solvent were charged thereinto, and the temperature was raised to 70° C. Thereafter, ethylene as a monomer was added so as to have its partial pressure of 1.6 MPa, to stabilize the interior of the system. As a result of gas chromatography analysis, a gas composition in the system was as follows: hydrogen=1.10%, 1-butene=4.24 mol %. Into this was charged 0.9 ml of a hexane solution of triisobutylaluminum, the concentration of which had been adjusted to 1 ml/l, as the organoaluminum compound A-2. Then, as the transition metal compound, 0.25 ml of a toluene solution of ethylenebis(5,6,7,8-tetrahydro-5,5,8,8-tetramethylbenz-f-indenyl)zirconium diphenoxide synthesized in Example 3, the concentration of which had been adjusted to 2 µmol/ml, was charged and, subsequently, 6.3 mg of the modified particle (C) obtained in Reference Example 2 and, as an electron donating compound, a toluene solution (0.9 ml) of triethylamine, the concentration of which had been adjusted to 0.1 mmol/ml, were charged together. Polymerization was performed at 70° C. for 3 hours while an ethylene/hydrogen mixed gas (hydrogen 0.29 mol %) was fed so as to maintain the total pressure constant. As a result, 164 g of an olefin polymer (ethylene-1-butene copolymer) was obtained. Polymerization activity per zirconium atom was $3.3\times10^8$ g/m, and the olefin polymer had a density of 0.919 g/cm$^3$, and a long chain branch number $N_{LCB}$ of 0.21. The results are shown in Table 1.

The density (unit: Kg/m$^3$) was measured using an annealing-treated sample described in JIS K6760-1995, and according to the method defined in the A method of JIS K7112-1980.

The long chain branch number ($N_{LCB}$, unit: 1/1000 C) influences the molding processability of a polymer, and the larger the long chain branch number is, the more excellent the polymer has molding processability. Carbon nuclear magnetic resonance spectrum ($^{13}$C-NMR) was measured under the following conditions, and the long chain branch number was obtained by the following calculation method.

Measurement Conditions

Apparatus: AVANCE$^{600}$ manufactured by Bruker
Measurement solvent: Mixed solution of 1,2-dichlorobenzene/1,2-dichlorobenzene-d4=75/25 (volume ratio)
Measurement temperature: 130° C.
Measurement method: Proton decoupling method
Pulse width: 45°
Pulse repetition time: 4 seconds
Measurement standard: Trimethylsilane
Window function: Negative exponential function Calculation Method Assuming that the sum of all peaks measured at 5 to 50 ppm is 1000, a peak area of a peak having a peak top around 38.22 to 38.27 ppm was obtained. The peak area was an area of a signal in a range of from a chemical shift of a valley with an adjacent peak at a high magnetic field side to a chemical shift of a valley with an adjacent peak at a low magnetic field side. In the measurement of an ethylene-α-olefin copolymer under the measurement conditions, a position of a peak top of a peak derived from methine carbon to which a branch having 5 carbon atoms had been bound, was 38.21 ppm.

Comparative Example 1

Polymerization was performed according to the same manner as in Example 4 except that (1) hydrogen was added so as to have its partial pressure of 0.035 MPa, (2) the transition metal compound was changed to racemic-ethylenebis(1-indenyl)zirconium diphenoxide, (3) the amount of the modified particle (C) was changed to 5.1 mg, and (4) the hydrogen concentration in the ethylene/hydrogen mixed gas was 0.56 mol %. A gas composition in the system before polymerization initiation by gas chromatography analysis was as follows: hydrogen=1.89 mol %, 1-butene=3.31 mol %.

As a result of polymerization, 120 g of an olefin polymer (ethylene-1-butene copolymer) was obtained. Polymerization activity per zirconium atom was $2.4\times10^8$ g/mol Zr, and the olefin polymer had an $N_{LCB}$ of 0.19. The results are shown in Table 1.

Comparative Example 2

Polymerization was performed according to the same manner as in Example 4 except that (1) the transition metal compound was changed to ethylenebis(5,6-dimethylindenyl)zirconium diphenoxide not satisfying the formula (1-1), (2) 93 g of 1-butene was used, (3) 657 g of butane as a polymerization solvent was used, (4) the amount of the modified particle (C) was changed to 6.0 mg, and (5) the hydrogen concentration in the ethylene/hydrogen mixed gas was 0.26 mol %. A gas composition in the system before polymerization initiation by gas chromatography analysis was as follows: hydrogen=0.93 mol %, 1-butene=4.58 mol %. As a result, 178 g of an olefin polymer (ethylene-1-butene copolymer) was obtained. Polymerization activity per zirconium atom was $3.6\times10^8$ g/mol Zr, and the olefin polymer had a density of 0.918 g/cm$^3$, and an $N_{LCB}$ of 0.08. The results are shown in Table 1.

Comparative Example 3

Polymerization was performed according to the same manner as in Example 4 except that (1) the transition metal compound was changed to ethylenebis(1,2,3,5-tetrahydro-s-indacenyl)zirconium diphenoxide not satisfying the formula (1-1), (2) 77 g of 1-butene was used, (3) 673 g of butane as a polymerization solvent was used, and (4) the amount of the modified particle (C) was changed to 4.6 mg. A gas composition in the system before polymerization initiation by gas chromatography analysis was as follows: hydrogen=1.01 mol %. As a result, 74 g of an olefin polymer (ethylene-1-butene copolymer) was obtained. Polymerization activity per zirconium atom was $1.5\times10^8$ g/mol Zr. The olefin polymer had a density of 0.922 g/cm$^3$, and an $N_{LCB}$ of 0.05. The results are shown in Table 1.

TABLE 1

|  | Activity g/mol Zr | Density g/cm$^3$ | $N_{LCB}$ |
| --- | --- | --- | --- |
| Example 4 | 3.3E+08 | 0.919 | 0.21 |
| Comparative Example 1 | 2.4E+08 | — | 0.19 |
| Comparative Example 2 | 3.6E+08 | 0.918 | 0.08 |
| Comparative Example 3 | 1.5E+08 | 0.922 | 0.05 |

Example 5

After drying under reduced pressure, the interior of an autoclave equipped with a stirrer having an internal volume of 3 L, replaced with argon, was made to be vacuum, hydrogen was added so as to have its partial pressure of 0.017 MPa, 7.1 g of 1-butene as a comonomer, and 679 g of butane as a polymerization solvent were charged thereinto, and the temperature was raised to 70° C. Thereafter, ethylene as a monomer was added so as to have its partial pressure of 1.6 MPa, to stabilize the interior of the system. As a result of gas chromatography analysis, a gas composition in the system was as follows: hydrogen=0.89 mol %, 1-butene=4.54 mol %. Into this was charged 0.9 ml of a hexane solution of triisobutylaluminum, the concentration of which had been adjusted to 1 mol/l, as the organoaluminum compound A-2. Then, as the transition metal compound, 0.25 ml of a toluene solution of ethylenebis(5,6,7,8-tetrahydro-5,5,8,8-tetramethylbenz-f-indenyl)zirconium diphenoxide synthesized in Example 3, the concentration of which had been adjusted to 2 μmol/ml, was charged thereinto and, subsequently, 5.0 mg of the modified particle (D) and, as an electron donating compound, a toluene solution (0.9 ml) of triethylamine, the concentration of which had been adjusted to 0.1 mmol/ml, were charged together. Polymerization was performed at 70° C. for 2 hours while an ethylene/hydrogen mixed gas (hydrogen 0.28 mol %) was fed so as to maintain the total pressure constant. As a result, 21.7 g of an olefin polymer (ethylene-1-butene copolymer) was obtained. Polymerization activity per zirconium atom was $4.3 \times 10^7$ g/mol Zr, and the olefin polymer had an $N_{LCB}$ of 0.13. The results are shown in Table 2.

Comparative Example 4

Polymerization was performed according to the same manner as in Example 5 except that (1) the transition metal compound was changed to racemic-ethylenebis(1-indenyl)zirconium diphenoxide not satisfying the formula (1-1), (2) the amount of the modified particle (D) was changed to 5.2 mg, and (3) the hydrogen concentration in the ethylene/hydrogen mixed gas was 0.25 mol %. A gas composition in the system before polymerization initiation by gas chromatography analysis was as follows: hydrogen=0.94 mol %, 1-butene=3.55 mol %. As a result, 36 g of an olefin polymer (ethylene-1-butene copolymer) was obtained. Polymerization activity per zirconium atom was $7.3 \times 10^7$ g/mol Zr, and the olefin polymer had a density of 0.921 g/cm$^3$, and an $N_{LCB}$ of 0.07. The results are shown in Table 2.

Comparative Example 5

Polymerization was performed according to the same manner as in Example 5 except that (1) the transition metal compound was changed to ethylenebis(5,6-dimethylindenyl)zirconium diphenoxide not satisfying the formula (1-1), (2) 93 g of 1-butene was used, (3) 657 g of butane as a polymerization solvent was used, (4) the amount of the modified particle (D) was changed to 5.9 mg, and (5) the hydrogen concentration in the ethylene/hydrogen mixed gas was 0.26 mol %. A gas composition in the system before polymerization initiation by gas chromatography analysis was as follows: hydrogen=0.81 mol %, 1-butene=5.47 mol %. As a result, 51 g of an olefin polymer (ethylene-1-butene copolymer) was obtained. Polymerization activity per zirconium atom was $1.01 \times 10^8$ g/mol Zr, and the olefin polymer had a density of 0.919 g/cm$^3$, and an $N_{LCB}$ of 0.05. The results are shown in Table 2.

Comparative Example 6

Polymerization was performed according to the same manner as in Example 5 except that (1) the transition metal compound was changed to ethylenebis(1,2,3,5-tetrahydro-s-indacenyl)zirconium diphenoxide not satisfying the formula (1-1), (2) 77 g of 1-butene was used, (3) 673 g of butane as a polymerization solvent was used, (4) the amount of the modified particle (D) was changed to 4.6 mg, and (5) the hydrogen concentration in the ethylene/hydrogen mixed gas was 0.29 mol %. A gas composition in the system before polymerization initiation by gas chromatography analysis was as follows: hydrogen=1.01 mol %. As a result, 74 g of an olefin polymer (ethylene-1-butene copolymer) was obtained. Polymerization activity per zirconium atom was $2.7 \times 10^7$ g/mol Zr, and the olefin polymer had an $N_{LCB}$ of 0.02. The results are shown in Table 2.

TABLE 2

|  | Activity g/mol Zr | Density g/cm$^3$ | $N_{LCB}$ |
| --- | --- | --- | --- |
| Example 5 | 4.3E+07 | — | 0.13 |
| Comparative Example 4 | 7.3E+07 | 0.921 | 0.07 |
| Comparative Example 5 | 1.0E+08 | 0.919 | 0.05 |
| Comparative Example 6 | 2.7E+07 | — | 0.02 |

Example 6

After drying under reduced pressure, the interior of an autoclave equipped with a stirrer having an internal volume of 3 L, replaced with argon, was made to be vacuum, hydrogen was added so as to have its partial pressure of 0.017 MPa, 122 g of 1-butene as a comonomer, and 628 g of butane as a polymerization solvent were charged thereinto, and the temperature was raised to 70° C. Thereafter, ethylene as a monomer was added so as to have its partial pressure of 1.6 MPa, to stabilize the interior of the system. As a result of gas chromatography analysis, a gas composition in the system was as follows: hydrogen=0.95%, 1-butene=9.53 mol %. Into this was charged 0.75 ml of a toluene solution of PMAO (manufactured by Tosoh Finechem Corporation), the concentration of which had been adjusted to 1.2 mol/l, as the organoaluminum compound A-1. Then, as the transition metal compound, 0.25 ml of a toluene solution of ethylenebis(5,6,7,8-tetrahydro-5,5,8,8-tetramemethylbenz-f-indenyl) zirconium diphenoxide synthesized in Example 3, the concentration of which had been adjusted to 2 μmol/ml, was charged. Polymerization was performed at 70° C. for 15 minutes while an ethylene/hydrogen mixed gas (hydrogen 0.25 mol %) was fed so as to maintain the total pressure constant. The resulting olefin polymer (ethylene-1-butene copolymer) had a density of 0.918 g/cm$^3$, and an $N_{LCB}$ of 0.15. Results are shown in Table 3.

Comparative Example 7

Polymerization was performed according to the same manner as in Example 6 except that (1) the transition metal compound was changed to racemic-ethylenebis (1-indenyl)zirconium diphenoxile not satisfying the formula (1-1), (2) 110 g of 1-butene was used, (3) 640 g of butane as a polymerization solvent was used, and (4) the hydrogen concentration in the ethylene/hydrogen mixed gas was 0.24 mol %. A gas composition in the system before polymerization initiation by gas chromatography analysis was as follows: hydrogen=0.91 mol %, 1-butene=7.31 mol %. As a result, 143 g of an olefin polymer (ethylene-1-butene copolymer) was obtained. Polymerization activity per zirconium atom was $2.85 \times 10^8$ g/mol Zr, and the olefin polymer had a density of 0.912 g/cm$^3$, and an $N_{LCB}$ of 0.10. The results are shown in Table 3.

Comparative Example 8

Polymerization was performed according to the same manner as in Example 6 except that (1) the transition metal compound was changed to ethylenebis(5,6-dimethylindenyl)zirconium diphenoxide not satisfying the formula (1-1), (2) 160 g of 1-butene was used, (3) 590 g of butane as a polymerization solvent was used, and (4) the hydrogen concentration in the ethylene/hydrogen mixed gas was 0.24 mol %. A gas composition in the system before polymerization initiation by gas chromatography analysis was as follows: hydrogen=0.74 mol %, 1-butene=12.2 mol %. As a result, 53 g of an olefin polymer (ethylene-1-butene copolymer) was obtained. Polymerization activity per zirconium atom was $1.06 \times 10^8$ g/mol Zr, and the olefin polymer had a density of 0.918 g/cm$^3$. As a result of the measurement, an $N_{LCB}$ could not be detected. The results are shown in Table 3.

Comparative Example 9

Polymerization was performed according to the same manner as in Example 6 except that (1) the transition metal compound was changed to ethylenebis(1,2,3,5-tetrahydro-s-indacenyl) zirconium diphenoxide not satisfying the formula (1-1), (2) 132 g of 1-butene was used, (3) 618 g of butane as a polymerization solvent was used, and (4) the hydrogen concentration in the ethylene/hydrogen mixed gas was 0.24 mol %. As a result, 28 g of an olefin polymer (ethylene-1-butene copolymer) was obtained. Polymerization activity per zirconium atom was $5.54 \times 10^7$ g/mol Zr, and the olefin polymer had a density of 0.928 g/cm$^3$, and an $N_{LCB}$ of 0.04. The results are shown in Table 3.

TABLE 3

|  | Activity g/mol Zr | Density g/cm$^3$ | $N_{LCB}$ |
|---|---|---|---|
| Example 6 | — | 0.918 | 0.15 |
| Comparative Example 7 | 2.9E+08 | 0.912 | 0.10 |
| Comparative Example 8 | 1.1E+08 | 0.918 | nd |
| Comparative Example 9 | 5.5E+07 | 0.928 | 0.04 | nd: not detected.

Example 7

Synthesis of (5,6,7,8-tetrahydro-5,5,8,8-tetramethyl-benz-f-indenyl) (indenyl)ethane A 1000 mL three-neck flask replaced with nitrogen was charged with 12.5 g (purity 98%, 108 mmol) of indene and 324 mL of tetrahydrofuran, and cooled in an ice bath, and then 67.7 mL (1.59 M, 108 mmol) of a hexane solution of n-butyllithium was added dropwise. The color of the solution turned from colorless to yellow. The temperature of this solution was gradually raised to room temperature, and the solution was stirred for further 1 hour to prepare a tetrahydrofuran solution of lithium indenide.

Separately, a 1000 mL three-neck flask replaced with nitrogen was charged with 29.9 g (purity 89%, 80 mmol) of a mixture (94:6) of 1-bromo-2-(5,5,8,8-tetramethyl-5,6,7,8-tetrahydrobenz-f-inden-1-yl)ethane and 1-bromo-2-(5,5,8,8-tetramethyl-5,6,7,8-tetrahydrobenz-f-inden-3-yl)ethane synthesized in Reference Example 1, and 108 mL of tetrahydrofuran, and cooled to −78° C. The tetrahydrofuran solution of lithium indenide prepared as described above was gradually added dropwise thereto. The color of the solution turned to red. After completion of dropwise addition, the temperature of the reaction solution was raised to room temperature, and then the solution was further stirred overnight. While this solution was cooled in a water bath, 200 mL of distilled water was added dropwise. After the organic layer was separated, the aqueous layer was extracted with ethyl acetate. The separated organic layer and the extract were combined, washed with an aqueous saturated sodium chloride solution two times, and dried with sodium sulfate. Volatile components were distilled off under reduced pressure to obtain a yellow oily product. Yield amount 21.6 g (purity 72%, 42 mmol, yield 72%).

A 500 mL three-neck flask replaced with nitrogen was charged with 21.6 g (purity 72%, 42 mmol) of the yellow oily product and 274 mL of tetrahydrofuran, and cooled in an ice bath, and then 88.5 mL (1.59 M, 141 mmol) of a hexane solution of n-butyllithium was added dropwise. The color of the solution was turned from colorless to yellow. The temperature of this solution was gradually raised to room temperature, and the solution was further stirred for 1 hour. While this solution was cooled in a water bath, 137 mL of distilled water was added dropwise. After the organic layer was separated, the aqueous layer was extracted with ethyl acetate. The separated organic layer and the extract were combined, washed with an aqueous saturated sodium chloride solution two times, and dried with sodium sulfate. Volatile components were distilled off under reduced pressure, and the resulting yellow oily product was purified by column chromatography (developing solvent: heptane/methylene chloride v/v=9/1), and recrystallized with ethanol/methylene chloride. Based on the following $^1$H NMR (400 MHz, CDCl$_3$) data, the resulting pale yellow solid was identified to be (5,6,7,8-tetrahydro-5,5,8,8-tetramethylbenz-f-inden-3-yl)(inden-3-yl)ethane. Yield amount 9.1 g (purity>98%, 24 mmol, yield 57%).

δ 7.49-7.20 (m, 4H), 7.44 (s, 1H), 7.34 (s, 1H), 6.33 (s, 1H), 6.23 (s, 1H), 3.37 (s, 2H), 3.31 (s, 2H), 2.94 (s, 4H), 1.71 (s, 4H), 1.32 (s, 12H). GCMS m/z: 368 (M$^+$).

Example 8

Synthesis of ethylene(5,5,8,8-tetramethyl-5,6,7,8-tetrahydrobenz-f-indenyl) (indenyl)zirconium bis (dimethylamide)

Into a 100 mL four-neck Schlenk were charged (5,6,7,8-tetrahydro-5,5,8,8-tetramethylbenz-f-inden-3-yl)(inden-3-yl)ethane (1.5 g, 4.07 mmol) synthesized in Example 7, tetrakisdimethylaminozirconium (1.20 g, 4.48 mmol), tetra-n-butylammonium chloride (0.11 g, 0.41 mmol), and toluene (25 mL) under a nitrogen stream. This solution was stirred at room temperature for 10 minutes. After the temperature of the reaction solution was raised to 100° C., the solution was stirred for 1 hour. After cooled to room temperature, the toluene was distilled off under reduced pressure to obtain a red solid. To the red solid was added hexane (5 mL), and the temperature of the reaction solution was raised to 60° C., and the solution was stirred for 1 hour. After cooled to room temperature, filtration/washing were performed with a toluene/hexane (v/v=1/2) mixed solvent using Celite to remove tetra-n-butylammonium chloride which is an insoluble component. The solvent of the filtrate was distilled off under reduced pressure, hexane (5 ml) was added, the temperature was raised to 60° C., the solution was stirred for 1 hour, and cooled to room temperature and then a red precipitated crystal was precipitated. The crystal was washed with a small amount of hexane, filtered and dried to obtain a red precipitated crystal (0.45 g, 0.92 mmol, yield 23%).

Based on the following $^1$H NMR (400 MHz, CDCl$_3$) data, the red precipitated crystal was identified to be ethylene(5,5,8,8-tetramethyl-5,6,7,8-tetrahydrobenz-f-indenyl)(indenyl)zirconium bis(dimethylamide).

δ 7.67 (d, 1H, J=7.8 Hz), 7.66 (s, 1H), 7.44 (d, 1H, J=8.6 Hz), 7.40 (s, 1H), 7.05 (t, 1H, J=7.6 Hz), 6.79 (t, 1H, J=7.6 Hz), 6.40 (d, 1H, J=3.1 Hz), 6.22 (d, 1H, J=3.1 Hz), 5.99 (dd, 2H, J=3.1, 6.3 Hz), 3.64-3.70 (m, 2H), 3.41-3.49 (m, 2H), 2.45 (s, 6H), 2.43 (s, 6H), 1.63-1.74 (m, 4H), 1.45 (s, 3H), 1.44 (s, 3H), 1.39 (s, 3H), 1.21 (s, 3H).

Example 9

Synthesis of ethylene(5,5,8,8-tetramethyl-5,6,7,8-tetrahydrobenz-f-indenyl) (indenyl)zirconium dichloride Into a 100 mL four-neck Schlenk were charged (5,6,7,8-tetrahydro-5,5,8,8-tetramethylbenz-f-inden-3-yl) (inden-3-yl)ethane (1.0 g, 2.72 mmol) synthesized in Example 7, tetrakisdimethylaminozirconium (0.87 g, 3.26 mmol), tetra-n-butylammonium chloride (0.08 g, 0.27 mmol), and hexane (23 ml) under a nitrogen stream. This solution was stirred at room temperature for 10 minutes. The temperature of the reaction solution was raised, and the solution was stirred for 1 hour under refluxing. After cooled to room temperature, filtration/washing were performed with hexane using Celite to remove tetra-n-butylammonium chloride which is an insoluble component. The solvent of the filtrate was distilled off under reduced pressure to obtain a red solid (1.45 g).

Into a 100 mL four-neck Schlenk were charged the resulting red solid (1.0 g) and toluene (10 mL) under a nitrogen stream. To the solution was added chlorotrimethylsilane (0.94 ml, 7.35 mmol), and the mixture was stirred at room temperature for 1 hour. Filtration/washing were performed with toluene using Celite, and the solvent of the filtrate was distilled off under reduced pressure to obtain a reddish brown solid. The solid was washed with hexane and, thereafter, dried to obtain a colorless solid (0.86 g, 1.63 mmol, yield 89%). Based on the following $^1$H NMR (400 MHz, CDCl$_3$) data, the colorless solid was identified to be ethylene(5,5,8,8-tetramethyl-5,6,7,8-tetrahydrobenz-f-indenyl) (indenyl)zirconium dichloride.

δ 7.66 (d, 1H, J=8.6 Hz), 7.57 (s, 1H), 7.47 (d, 1H, J=8.6 Hz), 7.45 (s, 1H), 7.31 (m, 1H), 7.17 (m, 1H), 6.51 (d, 1H, J=3.3 Hz), 6.43 (d, 1H, J=3.3 Hz), 6.10 (m, 2H), 3.75 (m, 4H), 1.73 (m, 4H), 1.41 (s, 3H), 1.38 (s, 3H), 1.37 (s, 3H), 1.31 (s, 3H).

Example 10

Synthesis of ethylene(5,5,8,8-tetramethyl-5,6,7,8-tetrahydrobenz-f-indenyl) (indenyl)zirconium diphenoxide Into a 100 mL four-neck Schlenk were charged ethylene (5,5,8,8-tetramethyl-5,6,7,8-tetrahydrobenz-f-indenyl) (indenyl)zirconium bis(dimethylamide) (0.44 g, 0.80 mmol) synthesized in Examples 8, and toluene (7 ml) under a nitrogen stream. This solution was stirred at room temperature for 10 minutes, the temperature of the solution was raised to 100° C., and to the solution was added a toluene solution (3 ml) of phenol (0.15 g, 1.60 mmol) at a rate of 1.0 ml/minute. The reaction solution was stirred at 100° C. for 1 hour. After cooled to room temperature, toluene was distilled off under reduced pressure to obtain a yellow solid. To the yellow solid was added hexane (5 ml), the temperature of the reaction solution was raised to 60° C., and the solution was stirred for 1 hour. After cooled to room temperature, filtration/washing were performed with hexane (10 ml) and diethyl ether (15 ml), and a yellow solid (0.30 g, 0.47 mmol, yield 59%) was filtered, and dried. Based on the following $^1$H NMR (400 MHz, CDCl$_3$) data, the yellow solid was identified to be ethylene(5,5,8,8-tetramethyl-5,6,7,8-tetrahydrobenz-f-indenyl) (indenyl)zirconium diphenoxide.

δ 7.17 (d, 1H, J=7.9 Hz), 7.83 (s, 1H), 7.21-7.26 (m, 2H), 7.06-7.17 (m, 5H), 6.97 (m, 1H), 6.70-6.76 (m, 2H), 6.33 (d, 2H, J=7.8 Hz), 6.27 (d, 2H, J=7.8 Hz), 6.24 (d, 1H, J=3.3 Hz), 6.14 (d, 2H, J=3.3 Hz), 6.03 (d, 1H, J=3.3 Hz), 5.95 (d, 1H, J=3.3 Hz), 3.84-3.94 (m, 2H), 3.72-3.81 (m, 2H), 1.65-1.71 (m, 2H), 1.56 (s, 3H), 1.41 (s, 3H), 1.19-1.38 (m, 2H), 1.16 (s, 3H), 0.81 (s, 3H).

Example 11

Synthesis of ethylene(5,5,8,8-tetramethyl-5,6,7,8-tetrahydrobenz-f-indenyl) (indenyl)zirconium diphenoxide Into a 100 mL four-neck Schlenk were charged phenol (0.16 g, 1.71 mmol) and toluene (5 ml) under a nitrogen stream. The solution was cooled to 5° C., a n-butyllithium solution (1.65 M) (1.04 ml, 1.71 mmol) was added, and the mixture was stirred for 30 minutes. To the reaction solution was added a toluene solution (5 ml) of ethylene(5,5,8,8-tetramethyl-5,6,7,8-tetrahydrobenz-f-indenyl)(indenyl)zirconium dichloride (0.41 g, 0.78 mmol) synthesized in Example 9 at a rate of 1.0 ml/minute. The temperature of the reaction solution was raised, and the solution was stirred for 3 hours under refluxing. After cooled to room temperature, filtration/washing were performed with toluene using Celite, to remove lithium chloride which is an insoluble component. The toluene in the filtrate was removed under reduced pressure to obtain a yellow solid. To the yellow solid was added hexane (5 ml), filtration/washing were performed with hexane (10 ml) and diethyl ether (15 ml), and the yellow solid (0.28 g, 0.44 mmol, yield 56%) was filtered, and dried.

δ 7.17 (d, 1H, J=7.9 Hz), 7.83 (s, 1H), 7.21-7.26 (m, 2H), 7.06-7.17 (m, 5H), 6.97 (m, 1H), 6.70-6.76 (m, 2H), 6.33 (d, 2H, J=7.8 Hz), 6.27 (d, 2H, J=7.8 Hz), 6.24 (d, 1H, J=3.3 Hz), 6.14 (d, 2H, J=3.3 Hz), 6.03 (d, 1H, J=3.3 Hz), 5.95 (d, 1H, J=3.3 Hz), 3.84-3.94 (m, 2H), 3.72-3.81 (m, 2H), 1.65-1.71 (m, 2H), 1.56 (s, 3H), 1.41 (s, 3H), 1.19-1.38 (m, 2H), 1.16 (s, 3H), 0.81 (s, 3H).

Example 12

After drying under reduced pressure, the interior of an autoclave equipped with a stirrer having an internal volume of 3 L, replaced with argon, was made to be vacuum, hydrogen was added so as to have its partial pressure of 0.017 MPa, 55 g of 1-butene as a comonomer, and 695 g of butane as a polymerization solvent were charged thereinto, and the temperature was raised to 70° C. Thereafter, ethylene as a monomer was added so as to have its partial pressure of 1.6 Mpa, to stabilize the interior of the system. As a result of gas chromatography analysis, a gas composition in the system was as follows: hydrogen=1.14%, 1-butene=3.61 mol %. Into this was charged 0.9 ml of a hexane solution of triisobutylaluminum, the concentration of which had been adjusted to 1 mol/l, as the organoaluminum compound A-2. Then, as the transition metal compound, 0.25 ml of a toluene solution of ethylene(5,5,8,8-tetramethyl-5,6,7,8-tetrahydrobenz-f-indenyl)(indenyl)zirconium diphenoxide synthesized in Example 11, the concentration of which had been adjusted to 2 μmol/ml, was charged and, subsequently, 5.2 mg of the modified particle (C) obtained in Reference Example 2 and, as an electron donating compound, a toluene solution (0.9 ml) of triethylamine, the concentration of which had been adjusted to 0.1 mmol/ml, were charged together. Polymerization was performed at 70° C. for 3 hours while an ethylene/hydrogen mixed gas (hydrogen 0.26 mol %) was fed so as to maintain the total pressure constant. As a result, 175 g of an olefin polymer (ethylene-1-butene copolymer) was obtained. Polymerization activity per zirconium atom was $3.5 \times 10^8$ g/mol Zr, and the olefin polymer had a density of 0.922 g/cm$^3$, and an $N_{LCB}$ of 0.24. The results are shown in Table 4.

Comparative Example 10

Polymerization was performed according to the same manner as in Example 12 except that (1) hydrogen was added so as to have its partial pressure of 0.035 MPa, (2) the transition metal compound was changed to racemic-ethylene bis(1-indenyl)zirconium diphenoxide, (3) the amount of the modified particle (C) was changed to 5.1 mg, and (4) the hydrogen concentration in the ethylene/hydrogen mixed gas was 0.56 mol %. A gas composition in the system before polymerization initiation by gas chromatography analysis was as follows: hydrogen=1.89 mol %, 1-butene=3.31 mol %. As a result, 120 g of an olefin polymer (ethylene-1-butene copolymer) was obtained. Polymerization activity per zirconium atom was $2.4 \times 10^8$ g/mol Zr, and the olefin polymer had an $N_{LCB}$ of 0.19. The results are shown in Table 4.

Comparative Example 11

Polymerization was performed according to the same manner as in Example 12 except that (1) the transition metal compound was changed to ethylene bis(5,6-dimethylindenyl) zirconium diphenoxide, (2) 93 g of 1-butene was used, (3) 657 g of butane as a polymerization solvent was used, (4) the amount of the modified particle (C) was changed to 6.0 mg and (5) the hydrogen concentration in the ethylene/hydrogen mixed gas was 0.26 mol %. A gas composition in the system before polymerization initiation by gas chromatography analysis was as follows: hydrogen=0.93 mol %, 1-butene=4.58 mol %. As a result, 178 g of an olefin polymer (ethylene-1-butene-copolymer) was obtained. Polymerization activity per zirconium atom was $3.6 \times 10^8$ g/mol Zr, and the olefin polymer had a density of 0.918 g/cm$^3$, and an $N_{LCB}$ of 0.08. The results are shown in Table 4.

Comparative Example 12

Polymerization was performed according to the same manner as in Example of 12 except that (1) the transition metal compound was changed to ethylene(1,2,3,5-tetrahydro-s-indacenyl)(indenyl)zirconium diphenoxide, (2) 65 g of 1-butene was used, (3) 685 g of butane as a polymerization solvent was used, (4) the amount of the modified particle (C) was changed to 5.4 mg, and (5) the hydrogen concentration in the ethylene/hydrogen mixed gas was 0.24 mol %. A gas composition in the system before polymerization initiation by gas chromatography analysis was as follows: hydrogen=0.98 mol %, 1-butene=4.42 mol %. As a result, 134 g of an olefin polymer (ethylene 1-butene-copolymer) was obtained. Polymerization activity per zirconium atom was $2.7 \times 10^7$ g/mol Zr, and the olefin polymer had a density of 0.921 g/cm$^3$, and an $N_{LCB}$ of 0.09. The results are shown in Table 4.

TABLE 4

|  | Activity g/mol Zr | Density g/cm$^3$ | $N_{LCB}$ |
| --- | --- | --- | --- |
| Example 12 | 3.5E+08 | 0.922 | 0.24 |
| Comparative Example 10 | 2.4E+08 | — | 0.19 |
| Comparative Example 11 | 3.6E+08 | 0.918 | 0.08 |
| Comparative Example 12 | 2.7E+07 | 0.921 | 0.09 |

Example 13

After drying under reduced pressure, the interior of an autoclave equipped with a stirrer having an internal volume of 3 L, replaced with argon, was made to be vacuum, hydrogen was added so as to have its partial pressure of 0.017 MPa, 55 g of 1-butene as a comonomer, and 695 g of butane as a polymerization solvent were charged, and the temperature was raised to 70° C. Thereafter, ethylene as a monomer was added so as to have its partial pressure of 1.6 MPa, to stabilize the interior of the system. As a result of gas chromatography analysis, a gas composition in the system was as follows: hydrogen=0.80 mol %, 1-butene=4.07 mol %. Into this was charged 0.9 ml of a hexane solution of toriisobutylaluminum, the concentration of which had been adjusted to 1 mol/l, as the organoaluminum compound A-2. Then, as the transition metal compound, 0.25 ml of a toluene solution of ethylene(5,5,8,8-tetramethyl-5,6,7,8-tetrahydrobenz-f-indenyl)(indenyl)zirconium diphenoxide synthesized in Example 11, the concentration of which had been adjusted to 2 μmol/ml, was charged thereinto and, subsequently, 5.2 mg of the modified particle (D) and, as an electron donating compound, a toluene solution (0.9 ml) of triethylamine, the concentration of which had been adjusted to 0.1 mmol/ml, were charged together. Polymerization was performed at 70° C. for 2 hours while an ethylene/hydrogen mixed gas (hydrogen 0.24 mol %) was fed so as to maintain the total pressure constant. As a result, 8.8 g of an olefin polymer (ethylene-1-butene copolymer) was obtained. Polymerization activity per zirconium atom was $1.8 \times 10^7$ g/mol Zr, and the olefin polymer had a density of 0.931 g/cm$^3$, and an $N_{LCB}$ of 0.09. The results are shown in Table 5.

Comparative Example 13

Polymerization was performed according to the same manner as in Example 13 except that (1) the transition metal compound was changed to racemic-ethylenebis(1-indenyl)zirconium diphenoxide, (2) the amount of the modified particle (D) was changed to 5.2 mg, and (3) the hydrogen concentration in the ethylene/hydrogen mixed gas was 0.25 mol %. A gas composition in the system before polymerization initiation by gas chromatography analysis was as follows: hydrogen=0.94 mol %, 1-butene=3.55 mol %. As a result, 36 g of an olefin polymer (ethylene-1-butene copolymer) was obtained. Polymerization activity per zirconium atom was 7.3×10⁷ g/mol Zr, and the olefin polymer had a density of 0.921 g/cm³, and an $N_{LCB}$ of 0.07. The results are shown in Table 5.

Comparative Example 14

Polymerization was performed according to the same manner as in Example 13 except that (1) the transition mental compound was changed to ethylenebis(5,6-dimethylindenyl) zirconium diphenoxide, (2) 93 g of 1-butene was used, (3) 657 g of butane as a polymerization solvent was used, (4) the amount of the modified particle (D) was changed to 5.9 mg, and (5) the hydrogen concentration in the ethylene/hydrogen mixed gas was 0.26 mol %. A gas composition in the system before polymerization initiation by gas chromatography analysis was as follows: hydrogen=0.81 mol %, 1-butene=5.47 mol %. As a result, 51 g of an olefin polymer (ethylene-1-butene copolymer) was obtained. Polymerization activity per zirconium atom was 1.01×10⁸ g/mol Zr, and the olefin polymer had a density of 0.919 g/cm³, and an $N_{LCB}$ of 0.05. The results are shown in Table 5.

Comparative Example 15

Polymerization was performed according to the same manner as in Example 13 except that (1) the transition metal compound was changed to ethylene(1,2,3,5-tetrehydro-s-indacenyl)(indenyl)zirconium diphenoxide, (2) 65 g of 1-butene was used, (3) 685 g of butane as a polymerization solvent was used, (4) the amount of the modified particle (D) was changed to 5.3 mg, and (5) the hydrogen concentration in the ethylene/hydrogen mixed gas was 0.27 mol %. A gas composition in the system before polymerization initiation by gas chromatography analysis was as follows: hydrogen=0.81 mol %, 1-butene=4.39 mol %. As a result, 12 g of an olefin polymer (ethylene-1-butene copolymer) was obtained. Polymerization activity per zirconium atom was 2.40×10⁷ g/mol Zr, and the resulting olefin polymer had a density of 0.918 g/cm³. As a result of the measurement, an $N_{LCB}$ could not be detected. The results are shown in Table 5.

TABLE 5

| | Activity g/mol Zr | Density g/cm³ | $N_{LCB}$ |
|---|---|---|---|
| Example 13 | 1.8E+07 | 0.931 | 0.09 |
| Comparative Example 13 | 7.3E+07 | 0.921 | 0.07 |
| Comparative Example 14 | 1.0E+08 | 0.919 | 0.05 |
| Comparative Example 15 | 2.4E+07 | 0.918 | nd | nd: not detected.

Example 14

After drying under reduced pressure, the interior of an autoclave equipped with a stirrer having an internal volume of 3 L, replaced with argon, was made to be vacuum, hydrogen was added so as to have its partial pressure of 0.017 MPa, 94 g of 1-butene as a comonomer, and 656 g of butane as a polymerization solvent were charged thereinto, and the temperature was raised to 70° C. Thereafter, ethylene as a monomer was added so as to have its partial pressure of 1.6 MPa, to stabilize the interior of the system. As a result of gas chromatography analysis, a gas composition in the system was as follows: hydrogen=0.85%, 1-butene=6.59 mol %. Into this was charged 0.75 ml of a toluene solution of PMAO (manufactured by Tosoh Finechem Corporation), the concentration of which had been adjusted to 1.2 mol/l, as the organoaluminum compound A-1. Then, as the transition metal compound, 0.25 ml of a toluene solution of ethylene(5,5,8,8-tetramethyl-5,6,7,8-tetrahydrobenz-f-indenyl)(indenyl) zirconium diphenoxide synthesized in Example 11, the concentration of which had been adjusted to 2 μmol/ml, was charged thereinto.

Polymerization was performed at 70° C. for 2 hours while an ethylene/hydrogen mixed gas (hydrogen 0.25 mol %) was fed so as to maintain the total pressure constant. As a result, 168 g of an olefin polymer (ethylene-1-butene copolymer) was obtained. Polymerization activity per zirconium atom was 3.4×10⁸ g/mol Zr, and the olefin polymer had a density of 0.920 g/cm³, and an $N_{LCB}$ of 0.13. The results are shown in Table 6.

Comparative Example 16

Polymerization was performed according to the same manner as in Example 14 except that (1) the transition metal compound was changed to racemic-ethylenebis(1-indenyl) zirconium diphenoxide, (2) 110 g of 1-butene was used, (3) 640 g of butane as a polymerization solvent was used, and (4) the hydrogen concentration in the ethylene/hydrogen mixed gas was 0.24 mol %. A gas composition in the system before polymerization initiation by gas chromatography analysis was as follows: hydrogen=0.91 mol %, 1-butene=7.31 mol %. As a result, 143 g of an olefin polymer (ethylene-1-butene copolymer) was obtained. Polymerization activity per zirconium atom was 2.85×10⁸ g/mol Zr, and the olefin polymer had a density of 0.912 g/cm³, and an $N_{LCB}$ of 0.10. The results are shown in Table 6.

Comparative Example 17

Polymerization was performed according to the same manner as in Example 14 except that (1) the transition metal compound was changed to ethylenebis(5,6-dimethylindenyl) zirconium diphenoxide, (2) 160 g of 1-butene was used, (3) 590 g of butane as a polymerization solvent was used, and (4) the hydrogen concentration in the ethylene/hydrogen mixed gas was 0.24 mol %. A gas composition in the system before polymerization initiation by gas chromatography analysis was as follows: hydrogen=0.74 mol %, 1-butene=12.2 mol %. As a result, 53 g of an olefin polymer (ethylene-1-butene copolymer) was obtained. Polymerization activity per zirconium atom was 1.06×10⁸ g/mol Zr, and the olefin polymer had a density of 0.918 g/cm³. As a result of the measurement, an $N_{LCB}$ could not be detected. The results are shown in Table 6.

Comparative Example 18

Polymerization was performed according to the same manner as in Example 14 except that (1) the transition metal compound was changed to ethylene(1,2,3,5-tetrahydro-s-indacenyl)(indenyl)zirconium diphenoxide, (2) 112 g of 1-butene was used, (3) 638 g of butane as a polymerization solvent was used, and (4) the hydrogen concentration in the ethylene/hydrogen mixed gas was 0.24 mol %. As a result, 33 g of an olefin polymer (ethylene-1-butene copolymer) was obtained. Polymerization activity per zirconium atom was 6.64×10⁷ g/mol Zr, and the olefin polymer had a density of 0.925 g/cm³. As a result of the measurement, an $N_{LCB}$ could not be detected. The results are shown in Table 6.

TABLE 6

|  | Activity g/mol Zr | Density g/cm³ | $N_{LCB}$ |
|---|---|---|---|
| Example 14 | 3.4E+08 | 0.920 | 0.13 |
| Comparative Example 16 | 2.9E+08 | 0.912 | 0.10 |
| Comparative Example 17 | 1.1E+08 | 0.918 | nd |
| Comparative Example 18 | 6.6E+07 | 0.925 | nd | nd: not detected.

Example 15

After an autoclave equipped with a stirrer having an internal volume of 400 mL was vacuum-dried, and replaced with argon, 150 mL of toluene as a solvent, and 20 g of propylene as a monomer were charged thereinto, and the temperature of the reactor was raised to 60° C. After the rise in temperature, 1.18 mL (0.50 mmol) of triisobutylaluminum (0.425 mmol/mL, toluene solution) was charged thereinto, subsequently, 0.20 ml of a toluene solution of ethylene(5,5,8,8-tetramethyl-5,6,7,8-tetrahydrobenz-f-indenyl)(indenyl)zirconium diphenoxide synthesized in Example 11, the concentration of which had been adjusted to 0.50 µmol/ml, was charged thereinto. Further, subsequently, 0.30 mL (0.3 µmol) of N,N-dimethylaniliniumtetrakis(pentafluorophenyl) borate (1.0 µmol/mL, toluene solution) was charged thereinto, and polymerization was initiated.

The polymerization was performed for 25 minutes while the temperature was maintained at 60° C.

As a result of the polymerization, 1.5 g of polypropylene was obtained. Polymerization activity=3.6×10⁷ g/mol/h, melting point=137.8° C., $M_w$=27,500, $M_w/M_n$=2.0, isotactic pentad fraction [mmmm]=81.4%.

Example 16

After an autoclave equipped with a stirrer having an internal volume of 400 mL was vacuum-dried, and replaced with argon, 150 mL of hexane as a solvent, and 20 g of propylene as a monomer were charged thereinto, and the temperature of the reactor was raised to 60° C. After the rise in temperature, 1.48 mL (0.50 mmol) of triisobutylaluminum (0.337 mmol/mL, hexane solution) was charged thereinto and, subsequently, 0.20 ml of a toluene solution of ethylene(5,5,8,8-tetramethyl-5,6,7,8-tetrahydrobenz-f-indenyl)(indenyl) zirconium diphenoxide synthesized in Example 11, the concentration of which had been adjusted to 0.50 µmol/ml, was charged thereinto. Further, subsequently, 0.30 mL (0.3 µmol) of N,N-dimethylaniliniumtetrakis(pentafluorophenyl) borate (1.0 µmol/mL, hexane solution) was charged thereinto, and polymerization was initiated. The polymerization was performed for 40 minutes while the temperature was maintained at 60° C.

As a result of the polymerization, 3.8 g of polypropylene was obtained. Polymerization activity=5.7×10⁷ g/mol/h, melting point=132.9° C., $M_w$=26,700, $M_w/M_n$=2.1, isotactic pentad fraction [mmmm]=81.7%.

The isotactic pentad fraction ([mmmm]) is a fraction of a propylene monomer unit present at the center of an isotactic linkage in a pentad unit in a crystalline polypropylene molecular chain, in other words, a linkage in which 5 successive propylene monomer units are meso-bound, measured by the method using ¹³C-NMR, published in "Macromolecules", Vol. 6, 925 (1973) by A. Zambelli et al., and about 200 mg of a polymer was uniformly dissolved in 3 mL of orthodichlorobenzene in a 10 mmφ test tube to prepare a sample, and ¹³C-NMR spectrum of the sample was measured. The value was measured under the following condition, employing a nuclear magnetic resonance apparatus (AVANCE⁶⁰⁰ manufactured by Bruker). The assignments of NMR absorption peaks were determined according to F. A. Bovey et al. "Macromolecules", Vol. 8, 687 (1975).

Measurement temperature: 130° C.
Pulse repetition time: 4 seconds
Pulse width: 45°
Integration times: 700 times
Chemical shift value standard: tetramethylsilane

What is claimed is:

1. A transition metal compound represented by the formula (1-2):

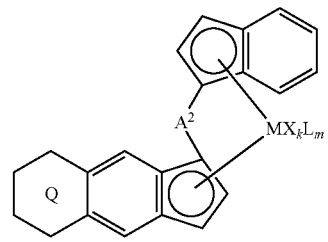

(1-2)

wherein M represents a transition metal atom of the Group 3, 4, 5, Group lanthanide or Group actinide of the periodic table,

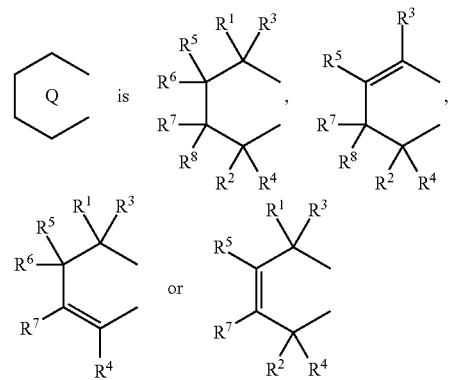

Q is (i) $R^1$ and $R^2$ are the same as, or different from each other, and represent an alkyl group having 1 to 20 carbon atoms and optionally having a halogen atom as a substituent,
a cycloalkyl group having 3 to 10 carbon atoms and optionally having a halogen atom as a substituent,
an alkenyl group having 2 to 20 carbon atoms and optionally having a halogen atom as a substituent,
an alkynyl group having 2 to 20 carbon atoms and optionally having a halogen atom as a substituent,
an aralkyl group having 7 to 20 carbon atoms and optionally having a halogen atom as a substituent, or
an aryl group having 6 to 20 carbon atoms and optionally having a halogen atom as a substituent, (ii) $R^3$ and $R^4$ are the same as, or different from each other, and represent a hydrogen atom,
an alkyl group having 1 to 20 carbon atoms and optionally having a halogen atom as a substituent, a cycloalkyl group having 3 to 10 carbon atoms and optionally having a halogen atom as a substituent,
an alkenyl group having 2 to 20 carbon atoms and optionally having a halogen atom as a substituent,
an alkynyl group having 2 to 20 carbon atoms and optionally having a halogen atom as a substituent,
an aralkyl group having 7 to 20 carbon atoms and optionally having a halogen atom as a substituent, or
an aryl group having 6 to 20 carbon atoms and optionally having a halogen atom as a substituent,
(iii) $R^5$ to $R^8$ are the same as, or different from one another, and represent a hydrogen atom,
an alkyl group having 1 to 20 carbon atoms and optionally having a halogen atom as a substituent,
a cycloalkyl group having 3 to 10 carbon atoms and optionally having a halogen atom as a substituent,
an alkenyl group having 2 to 20 carbon atoms and optionally having a halogen atom as a substituent,
an alkynyl group having 2 to 20 carbon atoms and optionally having a halogen atom as a substituent,
an aralkyl group having 7 to 20 carbon atoms and optionally having a halogen atom as a substituent,
an aryl group having 6 to 20 carbon atoms and optionally having a halogen atom as a substituent,
an alkoxy group having 1 to 20 carbon atoms and optionally having a halogen atom as a substituent,
an aralkyloxy group having 7 to 20 carbon atoms and optionally having a halogen atom as a substituent,
an aryloxy group having 6 to 20 carbon atoms and optionally having a halogen atom as a substituent,
a silyl group optionally having, as a substituent, a hydrocarbyl group or a halogenated hydrocarbyl group having 1 to 20 carbon atoms,
an amino group optionally having, as a substituent, a hydrocarbyl group or a halogenated hydrocarbyl group having 1 to 20 carbon atoms, or
a heterocyclic compound residue,
(iv) $R^1$ and $R^3$, $R^2$ and $R^4$, $R^5$ and $R^6$, $R^5$ and $R^7$, or $R^7$ and $R^8$ may be taken together with each other to form a ring, wherein the ring may have a substituent;
$A^2$ represents a $—[Z(R^{11})(R^{12})]_n$-group, wherein Z represents a silicon atom, a germanium atom, a tin atom or a carbon atom, $R^{11}$ and $R^{12}$ are the same as, or different from each other, and represent a hydrogen atom,
an alkyl group having 1 to 20 carbon atoms and optionally having a halogen atom as a substituent,
a cycloalkyl group having 3 to 10 carbon atoms and optionally having a halogen atom as a substituent,
an aryl group having 6 to 20 carbon atoms and optionally having a halogen atom as a substituent, or
a silyl group optionally having, as a substituent, a hydrocarbyl group or a halogenated hydrocarbyl group having 1 to 20 carbon atoms, and
n represents 1, 2, 3 or 4, and when plural Zs, $R^{11}$s or $R^{12}$s exist, they may be the same as, or different from one another,
X represents a hydrogen atom, a fluorine atom, a chlorine atom, a bromine atom, an iodine atom,
an alkyl group having 1 to 20 carbon atoms and optionally having a halogen atom as a substituent,
a cycloalkyl group having 3 to 10 carbon atoms and optionally having a halogen atom as a substituent,
an aralkyl group having 7 to 20 carbon atoms and optionally having a halogen atom as a substituent,
an aryl group having 6 to 20 carbon atoms and optionally having a halogen atom as a substituent,
an alkoxy group having 1 to 20 carbon atoms and optionally having a halogen atom as a substituent,
an aralkyloxy group having 7 to 20 carbon atoms and optionally having a halogen atom as a substituent,
an aryloxy group having 6 to 20 carbon atoms and optionally having a halogen atom as a substituent,
a silyl group optionally having, as a substituent, a hydrocarbyl group or a halogenated hydrocarbyl group having 1 to 20 carbon atoms,
an amino group optionally having, as a substituent, a hydrocarbyl group or a halogenated hydrocarbyl group having 1 to 20 carbon atoms,
a thiolate group optionally having, as a substituent, a hydrocarbyl group or a halogenated hydrocarbyl group having 1 to 20 carbon atoms, or
a carboxylate group optionally having, as a substituent, a hydrocarbyl group or a halogenated hydrocarbyl group having 1 to 20 carbon atoms, and when plural Xs exist, they are the same as, or different from each other, and adjacent Xs may be taken together with each other to form a ring;
k represents 1, 2 or 3; L represents a neutral Lewis base, and when plural Ls exist, plural Ls are the same as, or different from each other; m represents 0, 1, 2, 3 or 4; the sum of k and m is 2, 3 or 4.

2. The transition metal compound according to claim 1, wherein Z is a silicon atom or a carbon atom.

3. The transition metal compound according to claim 1, wherein $A^2$ is a $—CH_2CH_2—$ group.

4. The transition metal compound according to claim 1, wherein

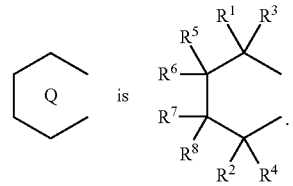

5. The transition metal compound according to claim 1, wherein
X is a fluorine atom, a chlorine atom, a bromine atom, an iodine atom,
an alkyl group having 1 to 20 carbon atoms and optionally having a halogen atom as a substituent,
an aralkyl group having 7 to 20 carbon atoms and optionally having a halogen atom as a substituent,
an alkoxy group having 1 to 20 carbon atoms and optionally having a halogen atom as a substituent,
an aryloxy group having 6 to 20 carbon atoms and optionally having a halogen atom as a substituent, or
an amino group optionally having, as a substituent, a hydrocarbyl group or a halogenated hydrocarbyl group having 1 to 20 carbon atoms, and adjacent Xs may be taken together with each other to form a ring.

6. The transition metal compound according to claim 1, wherein X is an aryloxy group having 6 to 20 carbon atoms and optionally having a halogen atom as a substituent.

7. The transition metal compound according to claim 1, wherein M is a titanium atom, a zirconium atom or a hafnium atom.

8. A process for producing a catalyst for olefin polymerization comprising a step of bringing the transition metal compound according to claim 1 into contact with a co-catalytic component for activation.

9. A process for producing an olefin polymer comprising a step of polymerizing an olefin in the presence of a catalyst for olefin polymerization produced by the production process according to claim 8.

10. The production process according to claim 9, wherein the olefin is a combination of ethylene and α-olefin.

* * * * *